US012584930B2

(12) United States Patent
Abhishek

(10) Patent No.: US 12,584,930 B2
(45) Date of Patent: Mar. 24, 2026

(54) FLUID PROPERTY MEASUREMENT DEVICES AND METHODS

(71) Applicant: Abram Scientific, Inc., South San Francisco, CA (US)

(72) Inventor: Ramkumar Abhishek, Menlo Park, CA (US)

(73) Assignee: Abram Scientific, Inc., South San Francisco, CA (US)

( * ) Notice: Subject to any disclaimer, the term of this patent is extended or adjusted under 35 U.S.C. 154(b) by 873 days.

(21) Appl. No.: 16/779,956

(22) Filed: Feb. 3, 2020

(65) Prior Publication Data

US 2020/0256882 A1 Aug. 13, 2020

Related U.S. Application Data

(60) Provisional application No. 62/800,704, filed on Feb. 4, 2019.

(51) Int. Cl.
*G01N 33/86* (2006.01)

(52) U.S. Cl.
CPC ... *G01N 33/86* (2013.01); *G01N 2333/96444* (2013.01)

(58) Field of Classification Search
CPC ......... G01N 11/16; G01N 2291/02466; G01N 2291/02818; G01N 29/02; G01N 29/022;
(Continued)

(56) References Cited

U.S. PATENT DOCUMENTS 3,766,774 A 10/1973 Clark
4,166,381 A 9/1979 Woo
(Continued)

FOREIGN PATENT DOCUMENTS

EP 0 400 939 A2 5/1990
EP 1 004 882 A2 5/2000
(Continued)

OTHER PUBLICATIONS

Frieder Lucklum, Miniature density-viscosity measurement cell utilizing electrodynamic-acoustic resonator sensors, 2011 (Year: 2011).*
(Continued)

*Primary Examiner* — John E Breene
*Assistant Examiner* — Truong D Phan
(74) *Attorney, Agent, or Firm* — Finnegan, Henderson, Farabow, Garrett & Dunner, LLP

(57) ABSTRACT

Disclosed herein are devices for measuring, at one or more time points, one or more properties or changes in properties of a fluid sample. The devices may comprise a chamber defining an internal volume of the device suitable for receiving and retaining the fluid sample; a plurality of layers, the plurality comprising at least a bottom layer below the chamber and at least a substrate layer above the chamber, wherein: the substrate layer is linked to at least one suspended beam at each end of its length; the suspended beam is located above the chamber, the suspended beam having a face capable of physical contact with the fluid sample; and the suspended beam is configured to oscillate upon application of an actuating signal to at least one electrically conductive path, which runs across the suspended beam. Related methods and uses are also disclosed.

16 Claims, 25 Drawing Sheets

(58) Field of Classification Search
CPC ........... G01N 29/036; G01N 33/48707; G01N
33/4905; G01N 2291/0427; G01N
2015/0065; G01N 15/05; G01N
2015/055; G01N 33/48; G01N 33/86;
G01N 2333/96444; G01N 33/49; G01N
9/002; G01N 2291/014; G01N 2291/022;
G01N 2291/101
USPC ....... 73/862.637–862.639, 862.632–862.634,
73/504.15–504.16, 514.36, 32 A, 54.02,
73/54.41; 435/13
See application file for complete search history.

(56) References Cited

U.S. PATENT DOCUMENTS

| | | | |
|---|---|---|---|
| 4,341,111 A | 7/1982 | Husar |
| 4,429,564 A | 2/1984 | Ikeda et al. |
| 4,862,384 A | 8/1989 | Bujard |
| 4,905,499 A | 3/1990 | Miura et al. |
| 4,920,787 A | 5/1990 | Dual et al. |
| 5,146,787 A | 9/1992 | Thomas et al. |
| 5,201,215 A | 4/1993 | Granstaff et al. |
| 5,211,054 A | 5/1993 | Muramatsu et al. |
| 5,302,878 A | 4/1994 | Soucemarianadin et al. |
| 5,334,303 A | 8/1994 | Muramatsu et al. |
| 5,372,946 A | 12/1994 | Cusak et al. |
| 5,418,141 A | 5/1995 | Zweig et al. |
| 5,494,639 A | 2/1996 | Grzegorzewski |
| 5,526,111 A | 6/1996 | Collins et al. |
| D371,605 S | 7/1996 | Wong et al. |
| 5,533,381 A | 7/1996 | Seale |
| 5,565,620 A | 10/1996 | Bohlin |
| 5,580,744 A | 12/1996 | Zweig |
| 5,628,961 A | 5/1997 | Davis et al. |
| 5,795,993 A | 8/1998 | Pfeifer et al. |
| 5,832,921 A | 11/1998 | Lennert et al. |
| 5,837,885 A | 11/1998 | Goodbread et al. |
| 5,841,023 A | 11/1998 | Parker et al. |
| 5,886,252 A | 3/1999 | Lennert et al. |
| 5,889,351 A | 3/1999 | Okumura et al. |
| 6,023,961 A | 2/2000 | Discenzo et al. |
| D435,020 S | 12/2000 | Zweig et al. |
| 6,171,237 B1 | 1/2001 | Avitall et al. |
| D438,971 S | 3/2001 | Meyer et al. |
| 6,198,950 B1 | 3/2001 | Kraus |
| 6,200,532 B1 | 3/2001 | Wu et al. |
| 6,269,686 B1 | 8/2001 | Hahn et al. |
| 6,397,661 B1 | 6/2002 | Grimes et al. |
| 6,448,024 B1 | 9/2002 | Bruegger |
| 6,575,900 B1 | 6/2003 | Zweig |
| 6,629,057 B2 | 9/2003 | Zweig et al. |
| 6,668,621 B1 | 12/2003 | Wright |
| 6,673,622 B1 | 1/2004 | Jina |
| 6,688,176 B2 | 2/2004 | Storm, Jr. et al. |
| 6,699,718 B1 | 3/2004 | Bruegger |
| 6,709,390 B1 | 3/2004 | Marie Pop |
| 6,771,081 B2 | 8/2004 | Borwick, III et al. |
| 6,800,488 B2 | 10/2004 | Khan et al. |
| 6,830,934 B1 | 12/2004 | Harding et al. |
| 6,849,456 B2 | 2/2005 | Patel et al. |
| 6,907,772 B2 | 6/2005 | Kensey et al. |
| 6,908,593 B1 | 6/2005 | Shartle |
| 6,938,462 B2 | 9/2005 | Jakoby et al. |
| 7,002,281 B2 | 2/2006 | Andle |
| 7,059,176 B2 | 6/2006 | Sparks |
| 7,117,721 B2 | 10/2006 | Neel et al. |
| 7,131,342 B2 | 11/2006 | Hodges |
| 7,191,667 B2 | 3/2007 | Wenger et al. |
| 7,207,939 B2 | 4/2007 | Husher |
| 7,235,213 B2 | 6/2007 | Mpock et al. |
| 7,263,874 B2 | 9/2007 | Fitch et al. |
| 7,290,441 B2 | 11/2007 | Baek |
| 7,328,604 B2 | 2/2008 | DeNatale et al. |
| 7,329,932 B2 | 2/2008 | DeNatale et al. |

| | | | |
|---|---|---|---|
| 7,458,265 B2 | 12/2008 | Shih et al. |
| 7,552,619 B2 | 6/2009 | Andle |
| 7,674,616 B2 | 3/2010 | Farnam, III et al. |
| 7,727,467 B2 | 6/2010 | Burke et al. |
| 7,745,224 B2 | 6/2010 | Zander et al. |
| 7,758,505 B2 | 7/2010 | Fine et al. |
| 7,770,436 B2 | 8/2010 | Baek |
| 7,775,084 B2 | 8/2010 | Huq et al. |
| 7,775,976 B2 | 8/2010 | Fuller et al. |
| 7,874,199 B2 | 1/2011 | Chaudoreille et al. |
| 7,879,615 B2 | 2/2011 | Kautzky |
| 7,879,618 B2 | 2/2011 | Mosoiu et al. |
| 7,922,985 B2 | 4/2011 | Mahoney et al. |
| 8,166,801 B2 | 5/2012 | Sinha |
| 8,166,812 B2 | 5/2012 | Desroques et al. |
| 8,173,008 B2 | 5/2012 | Leong |
| 8,178,313 B2 | 5/2012 | Mahoney et al. |
| 8,187,658 B2 | 5/2012 | Mahoney et al. |
| 8,197,418 B2 | 6/2012 | Lal et al. |
| 8,210,030 B2 | 7/2012 | Djakov et al. |
| 8,215,156 B2 | 7/2012 | Miura |
| 8,272,274 B2 | 9/2012 | Sparks et al. |
| 8,277,384 B2 | 10/2012 | Fine |
| 2004/0087836 A1 | 5/2004 | Green et al. |
| 2006/0035298 A1 | 2/2006 | Hill et al. |
| 2008/0257036 A1 | 10/2008 | Chaudoreille et al. |
| 2009/0120168 A1 | 5/2009 | Harrison et al. |
| 2010/0015649 A1 | 1/2010 | Day |
| 2010/0252452 A1 | 10/2010 | Newman et al. |
| 2010/0332155 A1 | 12/2010 | Puchades et al. |
| 2011/0020785 A1 | 1/2011 | Lowery, Jr. et al. |
| 2011/0039285 A1 | 2/2011 | Sadaba Champetier De Ribes et al. |
| 2011/0040572 A1 | 2/2011 | Chmiel et al. |
| 2011/0061462 A1 | 3/2011 | Ichihashi et al. |
| 2011/0129929 A1 | 6/2011 | Day et al. |
| 2011/0151491 A1 | 6/2011 | Dennis et al. |
| 2011/0312002 A1 | 12/2011 | Taktak et al. |
| 2012/0152001 A1 | 6/2012 | Reichel et al. |
| 2012/0239314 A1 | 9/2012 | Kurauchi et al. |
| 2013/0192349 A1* | 8/2013 | Ramkumar ........ G01N 33/4905 |
| | | 73/61.79 |
| 2015/0000397 A1* | 1/2015 | Day ..................... G01N 11/16 |
| | | 73/32 A |
| 2016/0032355 A1 | 2/2016 | Zaman et al. |
| 2017/0059464 A1 | 3/2017 | Ramkumar et al. |
| 2018/0313735 A1 | 11/2018 | Gallagher |
| 2019/0111431 A1 | 4/2019 | Frydman et al. |

FOREIGN PATENT DOCUMENTS

| | | |
|---|---|---|
| EP | 0 717 838 | 5/2004 |
| EP | 1 588 161 | 10/2007 |
| GB | 2180691 A | 4/1987 |
| GB | 2478225 | 8/2011 |
| JP | 62063828 A | 3/1987 |
| JP | 03148878 A | 6/1991 |
| JP | 04233280 A | 8/1992 |
| JP | 08293615 A | 11/1996 |
| JP | 09503859 A | 4/1997 |
| JP | 2000-161962 A | 6/2000 |
| JP | 2004527747 A | 9/2004 |
| WO | WO 1995/008765 | 3/1995 |
| WO | WO 2002/077613 A2 | 10/2002 |
| WO | WO 2008/081181 | 7/2008 |
| WO | WO 2012/009550 | 1/2012 |

OTHER PUBLICATIONS

Reichel, Resonant measurement of liquid properties in a fluidic sensor cell, 2008, pp. 540-543 (Year: 2008).*
Chinese Patent Application No. 201380013950.1, by Abram Scientific, Inc.; First Office Action, issued Mar. 4, 2016, with English Translation.
Chinese Patient Application No. 201380013950.1, by Abram Scientific, Inc.; Search Report, issued Feb. 24, 2016, EnglishTranslation.

(56) References Cited

OTHER PUBLICATIONS

Japanese Patent Application No. 2014-552385, by Abram Scientific, Inc.; First Office Action, issued Dec. 6, 2016, with English Translation.

Japanese Patent Application No. 2014-552385, by Abram Scientific, Inc.: Notice of Reasons for Rejection, mailed Oct. 31, 2017, with English translation (10 pages).

Bandey et al., "Blood rheological characterization using the thickness-shear mode resonator," *Biosensors and Bioelectronics*, 19: 1657-1665 (2004).

Day, Highland Bioscience Ltd., "Towards a new diagnostic for cattle TB," slide deck dated Apr. 18, 2012, 15 pages.

Jakoby et al., "An Automotive Engine Oil Viscosity Sensor," *IEEE Sensors Journal*, 3(5): 562-568 (2003).

Lowe, "Blood rheology in arterial disease," *Clinical Science*, 71: 137-146 (1986).

Matrai et al., "A Simple Method of Estimating Whole Blood Viscosity at Standardized Hematocrit," *Clinical Hemorheology*, 7: 261-265 (1987).

Nwankwo et al., "Fluid property investigation by impedance characterization of quartz crystal resonators—Part II: Parasitic effects, viscoelastic fluids," *Sensors and Actuators*, 72: 195-202 (1999).

Rosencranz et al., "Clinical Laboratory Measurement of Serum, Plasma and Blood Viscosity," *Am. J. Clin Pathol.*, 125(Suppl. 1): S78-S86 (2006).

Wang et al., "Electrochemical Glucose Biosensors," *Chem. Rev.*, 108: 814-825 (2008).

Ho, "White Blood Cell and Platelet Counts Could Affect Whole Blood Viscosity," *J Chin Med Assoc*, 67: 394-397 (2004).

Shah et al., "Modeling a Piezoelectric TSM Sensor to study Kinetics of Multi-layer Biosensing Structure," *IEEE/EMBS International Summer School on Medical Devices and Biosensors (ISSS-MD)*, pp. 12-16 (2004).

PCT Notification of Transmittal of the International Search Report and the Written Opinion of the International Searching Authority, or the Declaration for International Application No. PCT/US2013/021597, mailed Aug. 27, 2013 (18 pages).

Ramkumar et al., "Silicon ultrasonic horn actuated microprobes based self-calibrating viscosity sensor," *2010 IEEE 23rd International Conference on Micro Electro Mechanical Systems (MEMS)*, pp. 991-994 (2010).

PCT Invitation to Pay Additional Fees and, Where Applicable, Protest Fee, and Communication Relating to the Results of the Partial International Search for International Application No. PCT/US2013/021597, mailed Jun. 13, 2013 (5 pages).

Lucklum et al., (2011) "Miniature density-viscosity measurement cell utilizing electrodynamic-acoustic resonator sensors", Sensors & Actuators: A. Physical, 172(1)75-81.

International Application PCT/2020/016351, by Abram Scientific, Inc., International Search Report and Written Opinion, dated May 27, 2020.

Counterpart European Application No. 20752150.1, by Abram Scientific, Inc., Extended European Search Report dated Sep. 19, 2022.

Jakoby et al., "Miniaturized sensors for the viscosity and density of liquids—performance and issues", IEEE Trans Ultrason Ferroelectr Freq Control, 57(1)111-120 (2010).

Abdallah, "Measurement error estimation and quality factor improvement of an electrodynamic-acoustic resonator sensor for viscosity measurement," Sensors and Actuators, A 199:318-324 (2013).

* cited by examiner

FLUID PROPERTY MEASUREMENT DEVICES AND METHODS

This application claims the benefit of U.S. Provisional Patent Application No. 62/800,704, filed on Feb. 4, 2019, which is incorporated herein by reference.

The present invention relates to fluid property measurement devices, methods and systems, e.g., viscosity of a fluid sample, viscosity of a bulk phase of a fluid sample, viscosity of a continuous phase of a fluid sample, viscoelasticity of a fluid sample, density of a fluid sample, plasma viscosity of a blood sample, whole blood viscosity of a blood sample, viscoelasticity of a blood sample, density of a blood sample, a hematocrit of a blood sample, a platelet count of a blood sample, a blood clotting time of a blood sample, a blood clot stiffness of a blood sample, a platelet contraction activity of a blood sample, a fibrinolysis activity of a blood sample, a concentration of a blood coagulation factor of a blood sample, an activity of a blood coagulation factor of a blood sample, a concentration of a blood constituent of a blood sample, an activity of a blood constituent of a blood sample, a type of an anticoagulant in a blood sample and a concentration of an anticoagulant in a blood sample.

Viscometers commonly derive the viscosity and/or viscoelasticity of a fluid by measuring the force required to achieve a specified shear rate (e.g., Wells-Brookfield, cone-plate type viscometer) [1]. Conventional laboratory viscometers are often not conducive for portable and online measurement of viscosity and viscoelasticity due to their cost, space requirements, and other pre-conditions, e.g., vibration-free mounting. Also, sample handling for such devices often involves manual labor and tends to be time-consuming and error-prone.

Vibration-damping based sensors can be small in size and be used for fluid property measurement with small sample volumes. The vibration-damping based sensors when exposed to a fluid induce an acoustic vibration field in the medium, which results in a viscosity- or viscoelasticity-modified damping or flow that can be measured electronically, optically, etc. When the vibration of the sensors corresponds to a resonance oscillation of the sensor, the damping of the oscillation can be measured using the quality factor of the resonance, the resonance frequency, and/or the resonant motion amplitude, among other variables. Examples of such sensors include microacoustic sensors like quartz thickness shear mode resonators (TSM) [2] and surface acoustic wave (SAW) devices which have been successfully used as alternatives to traditional viscometers [3]. These devices generally measure viscosity at relatively high frequencies and small vibration amplitudes, which can lead to significant disadvantages. Since the penetration depth ($\delta_s = \sqrt{\eta/\rho\pi f}$, where $\eta$ is fluid viscosity, $\rho$ is fluid density and f is frequency) of the acoustic field excited by these sensors is small due to their high vibration frequencies f, only a thin film of liquid close to the device is probed. Thus for non-Newtonian fluids, including but not limited to those containing discrete components/additives, the results may exhibit significant deviations from that measured in conventional viscometers.

Whole blood viscosity (WBV), a global measure of the intrinsic resistance of bulk blood to flow in vessels, is determined by the interaction between blood cell rheology, plasma viscosity (PV) and hematocrit, and may be considered a marker of circulatory function. Its major determinants are the volume fraction of red blood cells (Hematocrit or Hct), plasma viscosity (determined mainly by plasma fibrinogen, other biologically reactant globulins, and lipoproteins), red cell deformation (under high flow/shear conditions) and red cell aggregation leading to clotting/coagulation (under low flow/shear conditions) [4, 5]. It has been shown that increasing levels of blood viscosity within the general population may promote cardiovascular events through its potential rheological effects on atherogenesis, thrombogenesis, or ischemia distal to atherothrombotic stenoses or occlusions [4, 6]. Epidemiological studies have associated high blood viscosity with conventional risk factors such as the male gender, cigarette smoking, blood pressure, and plasma lipid/lipoproteins [5, 7]. A study of a random population of 1592 men and women, followed over a mean of 5 years, showed mean blood viscosity, after adjustment for age and sex, was higher in patients experiencing ischemic heart attacks and strokes than those who did not [8]. After correction for diastolic blood pressure, LDL cholesterol and smoking, the link between blood viscosity (and hematocrit-corrected blood viscosity) was significant only for stroke (p<0.05). A prospective study of 331 middle-aged hypertensive men (followed for an average of 4.8 years) revealed that the top tertile diastolic blood viscosity patients had increased risk of cardiovascular events [9]. Also, there is a strong correlation between the incidence of type-2 diabetes with WBV, and both the prediction of plasma hyperviscosity syndrome and the prognosis of sickle cell disease with plasma viscosity.

Blood is a non-Newtonian fluid, i.e., the viscosity of blood is dependent on the velocity of blood flow through vessels (more specifically, blood's shear rate). At high velocities of blood, the disc-shaped red blood cells orient in the direction of the flow and the viscosity is lower. For extremely low shear rates red blood cell aggregation may occur, thus increasing viscosity to very high values. It has also been suggested and demonstrated that a minimum shear stress (yield stress, $\tau_y$) is required before the blood will start to flow. To measure the viscosity of a blood sample, modern viscometers generally measure the rate of fluid flow at a specified force or, conversely, the amount of force required to achieve a predefined rate of flow. It does not matter which method is used for plasma viscosity measurement due to its Newtonian fluid properties. The rate of flow (proportional to shear rate) ideally should be precisely controlled and specified when measuring whole blood viscosity so as to foster standardization of measurement. But the current blood viscometers are unable to allow for whole blood and plasma viscosity measurement on the same sample and are bulky requiring large sample volumes.

The capability of measuring the physical properties of blood rapidly can allow for monitoring these properties as a function of time, including real-time monitoring of the coagulation of blood. The currently available hemorheological tests for diagnosis and monitoring of diseases include blood coagulation tests such as Prothrombin Time (PT) or International Normalized Ratio (INR), Partial Thromboplastin Time (PTT), Activated Clotting Time (ACT) and Thromboelastogram (TEG). The laboratory gold standard of measurement for all of the above-mentioned coagulation tests is a direct-mechanical, viscoelastic method, which monitors the change in the physical properties of the blood sample as it coagulates. But these tests when performed in the laboratory may require large samples of blood (3-5 ml), the addition of anticoagulants to preserve the sample (e.g., sodium citrate), and laborious testing processes using vibration-sensitive instruments, often requiring long turnaround times for test results to be generated.

The currently available point of care (POC) systems for coagulation diagnostic tests used in hospitals, clinics and at home (e.g., Roche's CoaguChe®), generally follow the finger-stick, capillary whole blood sampling and strip-based testing method as is commonly used in blood glucose meters. Though these devices are portable and easy to use, in contrast to the gold standard, direct-mechanical laboratory methods, they typically use indirect methods (e.g., electrical, optical) that measure a second order effect due to blood clotting and are prone to errors due to confounding factors, including but not limited to varying hematocrit and fibrinogen concentrations in the blood sample. A real-time POC measurement of the physical property of the complex fluid (here, blood viscosity, viscoelasticity and density) may help give real-time feedback on the effectiveness and response time of the treatment/therapy allowing for optimal hemostasis management. Also, monitoring viscosity or viscoelasticity as a function of time can be used in performing multiple coagulation tests on the same blood sample (e.g., PT/INR, PTT, ACT & TEG). Such a device could in effect be used for measuring blood & plasma viscosities and perform standardized coagulation measurements (including but not limited to PT/INR, PTT, ACT & TEG), thus giving a comprehensive picture of the blood coagulation status before, during and after therapy.

Thus, there is a current need for low sample volume (e.g., <10 µl, including but not limited to finger-stick blood sampling), rapid real-time measurement of rheological properties of whole blood and plasma (viscosity, viscoelasticity, density, and coagulation) in vitro or in vivo. Such an instrument, together with biosensors such as, e.g., glucose measurement for diabetic patients, could serve as an invaluable tool for rapid diagnosis and monitoring of disease and blood function.

In some embodiments, the present invention provides an acoustic vibrating sensor that can generate relatively greater vibration amplitudes and acoustic field penetration depths in fluids, which in turn can lead to a higher sensitivity and larger breadth of measurement of fluid properties. In some embodiments, the vibrating element is designed such that at least two acoustic fields corresponding to two different penetration depths can be induced in the fluid medium, and consequently different physical properties of the fluid can be measured using the two acoustic fields. For example, by using two penetration depths that are greater than and smaller than the size of discrete components/additives in the fluid, the viscosity of the continuous phase and the bulk phase (which reflects contribution from discrete components/additives) can be accurately determined in the same sample, without need for separating the discrete components/additives from the fluid. Also, by varying the vibration mode of the sensor in a device according to some embodiments, the density of the fluid can also be precisely measured, which in turn may be used to quantify the concentration of any discrete components/additives. This sensor could be found useful in a wide variety of fluid property measurement applications, e.g., measurement of properties of foods, beverages, paints, inks, oils and petroleum products, as well as biological fluids in vivo and in vitro.

In some embodiments, methods and devices according to the invention provide advantages for the measurement of whole blood viscosity, which is highly dependent on the viscosity of its continuous phase, i.e., plasma, and the concentration of discrete components such as red blood cells.

Some embodiments of the invention provide sensors that enable the simultaneous and rapid measurement of whole blood and plasma viscosities on the same blood sample and/or that can be configured to measure the density of blood which can be used to determine the hematocrit, because of the density being linearly related to the hematocrit by the simple relationship $\rho=1.026+0.067$ Hct gm/cc [10]. Since whole blood viscosity is highly dependent on the plasma viscosity and hematocrit, in order to compare/group the blood viscosity of different individuals it may be advisable to standardize the blood viscosity to a fixed hematocrit (0.45 is generally used). In most of the studies whole blood viscosity was standardized (or corrected) to a standard hematocrit of 45% by the formula of Matrai et al. [11]—

$$\left(\frac{\eta_{WBV-0.45}}{\eta_{plasma}}\right) = \left(\frac{\eta_{WBV-Hct}}{\eta_{plasma}}\right)^{0.45/Hct}$$

where $\eta_{WBV-0.45}$ is the corrected whole blood viscosity, $\eta_{WBV-Hct}$ is the whole blood viscosity at hematocrit Hct, and $\eta_{Plasma}$ is the plasma viscosity. Thus, in order to estimate the standardized blood viscosity using this approach, the hematocrit, whole blood viscosity and plasma viscosity of a sample need to be accurately determined. Currently, the measurement of whole blood and plasma viscosities generally involves time-consuming sample processing viz. centrifugation of red blood cells to separate plasma and measure hematocrit, and measurement of viscosities using bulky instruments by trained professionals. Also, since the blood volumes available from patients can be small (e.g., finger-stick, capillary blood) they must be analyzed quickly, preferably without the addition of anticoagulants. The currently existing methods for clinical diagnosis and in vitro study of blood in laboratories generally involve the addition of anticoagulants such as sodium citrate and EDTA, thus deviating from the true physiological state of blood [12]. In some embodiments, the invention provides the advantage of performing all three measurements viz. whole blood viscosity, plasma viscosity and hematocrit measurement on the same blood sample without requiring pre-processing of the samples, thus serving as a rapid POC diagnostics tool.

Accordingly, in one embodiment, the invention provides a device for measuring, at one or more time points, one or more properties or changes in properties of a fluid sample, the device comprising: a chamber defining an internal volume of the device suitable for receiving and retaining the fluid sample; a plurality of layers, the plurality comprising at least a bottom layer below the chamber and at least a substrate layer above the chamber, wherein: the substrate layer is linked to at least one suspended beam at each end of its length; the suspended beam is located above the chamber, the suspended beam having a face capable of physical contact with the fluid sample; and the suspended beam is configured to oscillate upon application of an actuating signal to at least one electrically conductive path, which runs across the suspended beam.

In another embodiment, the invention provides a method of measuring one or more properties or changes in properties of a fluid sample using a device according to the invention, the method comprising: placing the fluid sample in the chamber of the device; oscillating at least one of the at least one suspended beam of the device, wherein the oscillation induces a current or voltage in at least one of the electrically conductive paths of the device; measuring the current or voltage at one or more times; and using one or more of the measurements of the current or voltage to calculate the one or more properties or changes in properties of the fluid sample.

In another embodiment, the invention provides a method of determining one or more properties or changes in properties of a fluid sample, the method comprising: placing the fluid sample in a chamber wherein a chamber surface is comprised of a physical element capable of oscillating while in contact with the fluid; oscillating the physical element at one or more oscillation frequencies; measuring one or more characteristics of the oscillation of the physical element at the one or more oscillation frequencies; and determining one or more properties or changes in properties of the fluid sample using one or more of the measured oscillation characteristics.

In another embodiment, the invention provides a method of identifying the type and determining the concentration of one or more analytes present in a fluid sample, the method comprising: placing the fluid sample in a chamber wherein a chamber surface is comprised of an oscillating device capable of determining one or more properties or changes in properties of the fluid using one or more of its measured oscillation characteristics; initiating a reaction in the fluid sample; determining one or more characteristics or changes in characteristics of one or more fluid constituents during the reaction using one or more of the measured fluid properties; identifying the type of one or more analytes using one or more of the measured characteristics of one or more of the fluid constituents; and determining the concentration of one or more analytes using one or more of the measured fluid properties.

In another embodiment, the invention provides a use of a device according to the invention for the determination of at least one of viscosity of a fluid sample, viscosity of a bulk phase of a fluid sample, viscosity of a continuous phase of a fluid sample, viscoelasticity of a fluid sample, density of a fluid sample, plasma viscosity of a blood sample, whole blood viscosity of a blood sample, viscoelasticity of a blood sample, density of a blood sample, a hematocrit of a blood sample, a platelet count of a blood sample, a blood clotting time of a blood sample, a blood clot stiffness of a blood sample, a platelet contraction activity of a blood sample, a fibrinolysis activity of a blood sample, a concentration of a blood coagulation factor of a blood sample, an activity of a blood coagulation factor of a blood sample, a concentration of a blood constituent of a blood sample, an activity of a blood constituent of a blood sample, a type of an anticoagulant in a blood sample and a concentration of an anticoagulant in a blood sample.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The foregoing aspects and advantages of this invention may become apparent from the following detailed description with reference to the accompanying drawings in which:

FIG. 2(a) shows a schematic view of a sensor device embodiment in the form of a disposable test strip for use in determining the viscosity, viscoelasticity and/or density of a fluid sample, in particular a body fluid such as blood, while FIG. 2(b) shows an exploded view of the test strip which illustrates the components therein. FIGS. 2(c) and 2(d) show photographs of the assembled disposable test strip without and with a blood sample introduced into the strip, respectively.

FIG. 16(*a*) shows uncalibrated thrombin concentration or generation profiles measured in blood samples with increasing heparin concentrations from 0 to 3 IU/ml and, FIG. 16(*b*) shows a correlation plot of the corresponding ACT times in the samples as measured using the disposable test strips (CoagCare ACT) and the TEG-5000 RapidTEG assay.

FIG. 17(*a*) illustrates a typical oscillation characteristic of the in-plane vibration mode of the suspended beam measured as a function of time that is used to monitor clot stiffness G. FIG. 17(*b*) illustrates a dose response for clot stiffness G demonstrating an increasing trend when exposed to blood samples with increasing concentrations of cleavable fibrinogen.

FIG. 18(*a*) illustrates a typical oscillation characteristic of the in-plane vibration mode of the suspended beam measured as a function of time that is used to monitor the contraction of platelets. FIG. 18(*b*) illustrates a dose response for the rate of platelet contraction demonstrating a decreasing trend when exposed to blood samples with increasing concentrations of Eptifibatide GPIIb/IIIa platelet inhibitor.

FIG. 19(*a*) illustrates a typical oscillation characteristic of the in-plane vibration mode of the suspended beam measured as a function of time that is used to monitor the fibrinolysis rate Lys-Rate. FIG. 19(*b*) illustrates a dose response for fibrinolysis rate Lys-Rate demonstrating an increasing trend when exposed to blood samples with increasing concentrations of tissue plasminogen activator (tPA).

FIG. 20(*a*) illustrates a dose response for clot formation time (R) when exposed to blood samples with increasing concentrations of Dabigatran and, FIG. 20(*b*) further illustrates a correlation plot between these R times measured using the disposable test strips (CoagCare) and the ACT times measured using the TEG-5000 RapidTEG assay.

FIG. 21(*a*) illustrates a dose response for clot formation time (R) when exposed to blood samples with increasing concentrations of Rivaroxaban and, FIG. 21(*b*) further illustrates a correlation plot between these R times measured using the disposable test strips (CoagCare) and the ACT times measured using the TEG-5000 RapidTEG assay.

FIG. 22(*b*) and FIG. 22(*c*) illustrate Rivaroxaban's and Dabigatran's effect on maximum thrombin generation (ThrombinPeak) and clot stiffness G, with increasing Rivaroxaban and Dabigatran concentrations in the tested blood samples, respectively, as measured using a physical element in a disposable test strip. FIG. 22(*d*) illustrates the differential response of Rivaroxaban and Dabigatran using a metric that is expressed as the ratio of the normalized ThrombinPeak and clot stiffness G (referred to as [Fibrinogen]$^2$ in this figure), which is plotted for the tested samples with increasing Dabigatran and Rivaroxaban concentrations (referred to as new oral anticoagulants or NOAC in this figure).

DETAILED DESCRIPTION OF THE INVENTION

Definitions

Figure 1:
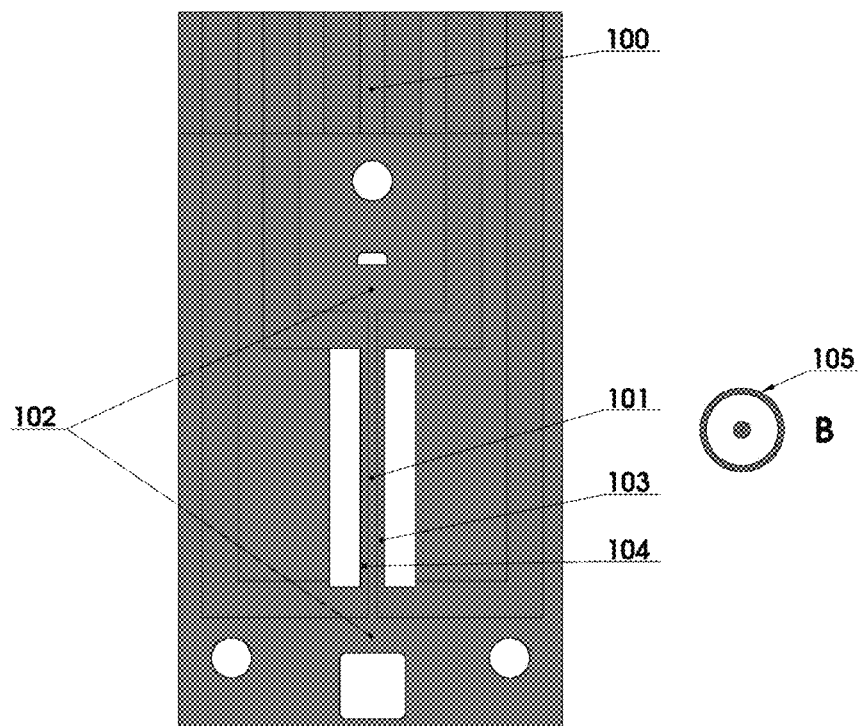
FIG. 1(a) depicts schematically an embodiment of a substrate layer comprising a physical element (i.e. suspended beam), which is suitable for measuring the absolute value of and/or changes in the viscosity, viscoelasticity and/or density of a fluid sample independently and/or before, during and after a reaction, with FIG. 1(b) showing an exploded view of the substrate layer that illustrates the component layers which contribute thereto.
Figure 1:
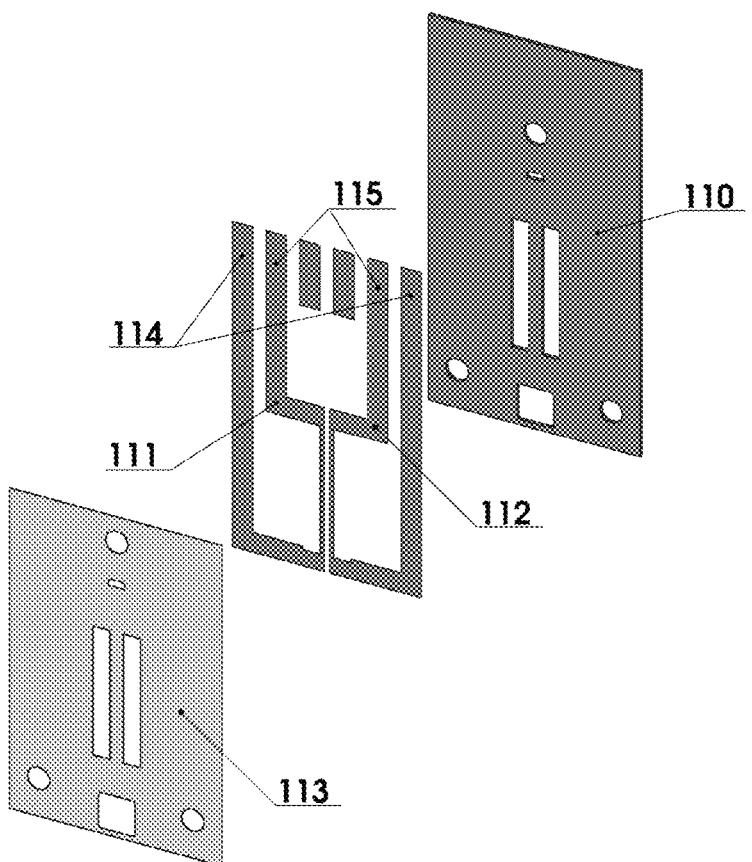

To facilitate the understanding of this invention, a number of terms are defined below. Terms not defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention but their usage does not delimit the invention, except as outlined in the claims.

Prothrombin Time (PT) or International Normalized Ratio (INR) test is an important index for the activity of coagulation factors of the extrinsic pathway—it is the coagulation time when tissue thromboplastin (a tissue factor) and/or calcium ions are added into the plasma or whole blood specimen to induce coagulation formation. Warfarin is prescribed to inhibit multiple factors involved in the coagulation cascade and its effectiveness is measured by the PT or INR test.

Partial Thromboplastin Time (PTT) test is an indicator of coagulation factors of the intrinsic pathway, measuring the time whole blood takes to coagulate. PTT is often used as a starting place when investigating the cause of a bleeding or thrombotic episode. The PTT test is used to determine the effectiveness of Heparin therapy administered to patients with perturbations in the intrinsic pathway (typically during invasive procedures).

Activated clotting time (ACT) test is used to monitor the effect of high-dose heparin before, during, and shortly after surgeries that require intense anticoagulant administration, such as cardiac bypass surgery, cardiac angioplasty, and dialysis. The test is performed in situations where the partial thromboplastin time (PTT) test is not clinically useful or takes too long.

Thromboelastography or Thromboelastogram (TEG) is a method of testing the efficiency of coagulation of blood. It is especially important in surgery, anesthesiology and trauma-related treatment. A small sample of blood (typically 0.36 ml) is placed into a cuvette (cup) which is rotated gently through 4° 45' (cycle time 6/min) to imitate sluggish venous flow and activate coagulation in the presence of an activator (e.g., thromboplastin, kaolin). When a sensor shaft is inserted into the sample a clot forms between the cup and the sensor. The speed and strength of clot formation is measured in various ways and depends on the activity of the plasmatic coagulation system, platelet function, fibrinolysis and other factors which may be affected by illness, environment and medications.

The quality factor (Q-factor) is a measurement of the "quality" of a resonant oscillating system; it is a measure of the sharpness of the oscillation's resonance or frequency selectivity of a resonant vibratory system, measured in a range of frequencies in the vicinity of the resonance oscillation frequency. The Q-factor can be measured by monitoring the amplitude of oscillation as a function of frequency in the vicinity of the resonance frequency. The Q-factor can be defined in multiple ways; a common definition is the ratio of the resonance frequency to the width of the peak. The width of the resonance peak can be determined, for example, as the distance between the two frequencies above and below the resonance frequency where the amplitude of oscillation falls to half the magnitude of the amplitude at the resonance frequency, which is generally known as the Full Width Half Max (FWHM). When a resonant oscillating system exhibits resonance and anti-resonance frequencies (as identified in the amplitude vs. frequency relationship), another way to measure Q-factor is by computing the ratio of the resonance frequency to the difference between the anti-resonance and resonance frequencies.

Shear penetration depth ($\delta_s$) is calculated as $\delta_s = \sqrt{\eta/\rho\pi f}$ where f is the oscillation frequency, $\eta$ is the viscosity of the fluid sample and $\rho$ is the density of the fluid sample.

Determination of properties of a fluid, including but not limited viscosity, viscoelasticity and density, can be achieved by determining the oscillation characteristics of a physical element. The oscillation may correspond to one of the natural or fundamental frequencies of resonance or oscillation of the physical element. The principle of resonance may be further defined with respect to the function of a tuning fork. When a tuning fork is excited by striking it against a surface or an object, its beams or prongs resonate at a certain frequency known as the fundamental frequency. The fundamental frequency of the prongs is dependent on the physical characteristics of the prongs such as the length and cross-sectional area of the prong, as well as the material from which the fork is made. More generally, the fundamental frequencies of resonance or oscillation of any physical element are dependent on the geometric shape and material properties of the same.

Electromagnetism has been used for inducing and monitoring motion as part of a variety of applications, for example, in rotors as part of motor assemblies. A possible electromagnetic mechanism of actuation involves applying an electrical current in the presence of a magnetic field resulting in a motion in the current carrying substrate as a result of the Lorentz force experienced by the conductor. Lorentz force $F_L$ is defined as the force experienced by a charge q moving with a velocity v in the presence of an electric field E and a magnetic field B given by $F_L = q[E + (v \times B)]$. Alternatively, the motion in a moving body with a conductive path through it can be detected by electromagnetic induction. Electromagnetic induction is the production of an electric current or voltage across a conductor moving in the presence of a magnetic field. Thus, using the principles of electromagnetism, motion can be both induced and monitored precisely. Alternatively, actuation methods such as piezoelectric, capacitive, electromagnetic, and thermal can be used to induce and monitor motion. Motion can also be monitored optically.

In some embodiments of the present invention, a device is provided in which the oscillation of a physical element (formed on or as part of a substrate layer), comprising a suspended beam attached to the substrate layer at each end of its length or width and capable of oscillations, is configured for monitoring the physical characteristics of a fluid. The physical element is provided with at least one conductive path running through it, and the suspended beam may have a planar, flat shape. An example of a planar, flat shape can be a rectangular shape with length and width in the range of 0.1 to 20 mm, and thickness less than 1/5th the length or width, with the flatness of the element defined by a surface roughness of less than $\frac{1}{5}^{th}$ the length or width. In an alternative embodiment, the physical element can be a non-rectangular shape. When an actuating signal by way of a current is passed through the physical element in the presence of a magnetic field with flux lines intersecting the physical element, oscillation is induced in the physical element. At a constant magnetic field, when an electric field via a time-varying current is applied/injected in at least one conductive path through the physical element, oscillation is induced in the physical element. Alternatively, applying a constant electric field through the physical element in the presence of a time-varying magnetic field can also be used to induce oscillation in the physical element. Also, the relative direction of the electric and magnetic fields can target specific types of oscillations and control the oscillation characteristics (such as amplitude, frequency, etc.) in the physical element. The oscillation is monitored by measuring the detection signal i.e. voltage or current induced by electromagnetic induction, in the at least one conductive path through the physical element, in a range of frequencies in the vicinity of the oscillation frequency. In some embodiments of the invention, the actuation and detection signals are applied and measured across the same or independent conductive paths through the physical element. Alternatively, other methods including but not limited to optical, piezoelectric, thermal, etc. can be used to monitor the oscillation.

The oscillation induced in the physical element can be at either a resonance or non-resonance frequency of the physical element. In some embodiments of the invention, when the frequency of the time-varying actuating signal corresponds to one or more of the natural or fundamental frequencies of resonance of the physical element, the corresponding mode(s) of oscillation is/are induced in the physical element. In other embodiments of the invention, the frequency of the time-varying actuating signal corresponds to one or more harmonics of one or more of the natural or fundamental resonance frequencies. The resonance oscillation characteristics can vary depending on the physical dimensional structure and material of the physical element, i.e. the suspended beam attached to the substrate layer at each end of its length, which can target specific frequencies of oscillation.

For example, the suspended beam can be flat and rectangular. Given the length l and width w of the rectangular beam, one can design two specific frequencies of resonance of the physical element along the length and width directions, respectively, and the magnitude of the resonance frequencies can be controlled by the corresponding lengths l and w. In some embodiments of the invention, the resonance frequencies of oscillation can correspond to in-plane and out-plane modes of oscillation of the physical element. In some embodiments of the invention, the resonance characteristics of the induced oscillation in the physical element can be computed by monitoring the induced detection signal in a range of frequencies in the vicinity of the resonance oscillation frequency. The measurable or quantifiable oscillation characteristics of the physical element include without limitation oscillation amplitude, phase, frequency and quality factor. In some embodiments of the invention, the actuation signal may correspond to a first resonance oscillation that couples to a second resonance or non-resonance oscillation, and results in both modes of oscillation being induced in the physical element. In this case, the detection signal can be measured in the vicinity of either or both of the induced oscillation frequencies.

In another embodiment of the invention, the oscillation of the physical element can be induced by coupling, interfacing or contacting the substrate where the physical element is located with a vibration inducing actuator which uses one excitation field or a combination of excitation fields chosen from (i) piezoelectricity-based mechanical, (ii) capacitive, (iii) electromagnetic, and (iv) thermal excitation fields. In some embodiments of the invention the physical element is provided with at least one conductive path running through it which may comprise elements with limited conductivity such as thermal resistors, piezoelectric resistors, etc. For example, a piezoelectric quartz crystal (PZT) oscillator can be physically affixed to the substrate layer, and the PZT oscillator can be driven to induce oscillations in the physical element at a particular oscillation frequency. When the PZT oscillator is driven at a frequency corresponding to one of the natural or fundamental frequencies of resonance (or their harmonics) of the physical element the corresponding mode of oscillation is excited. The geometric shape and material properties of the physical element, which may comprise a planar flat suspended beam, can be configured for the natural or fundamental frequency/frequencies of resonance of the physical element to be a specific value or within a given range of frequencies such as 1 Hz to 1 MHz. The PZT when actuated at these above-mentioned frequencies, induces resonance oscillations in the physical element.

Another embodiment involves applying capacitive fields between the physical element and one or more isolated, stationary electrode (located at a finite distance from the substrate layer linked to the physical element) to induce oscillations. The capacitive fields can be set up by applying a time-varying voltage signal between the conductive path running through the physical element and the one or more stationary electrodes. Applying a time-varying voltage at the natural or fundamental frequencies (or their harmonics) of the physical element can induce resonance oscillations in the physical element.

In yet another embodiment, thermal resistors are provided as part of the conductive path running through the physical element. Oscillations in the physical element at resonance or non-resonance frequencies can be induced by heating the resistors upon passing current through the conductive path running through the physical element. By applying a time-varying current signal, steady-state or transient oscillations can be induced in the physical element.

In another embodiment of the invention, the oscillation induced in the physical element is detected by one detection field or a combination of detection fields chosen from (i) piezoelectricity-based electrical, (ii) capacitive, (iii) electromagnetic, (iv) thermal and (v) optical detection fields arising due to the oscillation. For example, when a piezoelectric quartz crystal (PZT) oscillator affixed to the substrate is used to induce oscillations in the physical element, the oscillation characteristics can be monitored by measuring the PZT's electrical input characteristics in a frequency range in the vicinity of the oscillation frequency excited in the physical element.

Alternatively, one or more piezoelectric resistors can be provided as part of the conductive path running through the physical element, which exhibit a change in resistance due to the oscillation of the physical element. The oscillation can be monitored by incorporating the piezoelectric resistors as part of a Wheatstone bridge circuit and measuring the bridge voltage in a frequency range in the vicinity of the oscillation frequency excited in the physical element.

In yet another alternative, one or more thermal resistors are provided as part of the conductive path running through the physical element that can measure the change temperature due to the oscillation of the physical element. The thermal resistors can be made of pyroelectric materials which have the ability to induce a voltage with a change in temperature. The oscillations in the physical element can be monitored by measuring the change in voltage across the resistors in a frequency range in the vicinity of the oscillation frequency excited in the physical element.

In yet another alternative, an optical sensor module is used to direct an optical signal onto the physical element and monitor the reflected or transmitted optical signal using a photodetector. Measuring the photodetector output signal in the vicinity of the oscillation frequency excited in the physical element can monitor the oscillations in the physical element. Alternatively, a photodetector module can be incorporated on the physical element as part of the conductive path running through it. When an optical signal is directed onto the photodetector, the oscillation in the physical element can be monitored by measuring the change in the photodetector output in a frequency range in the vicinity of the oscillation frequency excited in the physical element.

In some embodiments of the invention, one or more physical elements (i.e. suspended beams) are located above a chamber, defining an internal volume which is suitable for receiving and retaining a fluid sample, and the one or more suspended beams are configured to oscillate upon application of an actuating signal.

In some embodiments of the invention, the internal volume of the chamber is configured to receive and hold the fluid sample in place before fluid property measurement is performed. The chamber is formed by a plurality of layers such that there exists at least one layer above (substrate layer) and at least one layer below (bottom layer) the chamber, such that the one or more physical elements (linked to the substrate layer) have a face capable of physical contact with the fluid sample. The use of a minimum of one substrate layer (linked to one or more physical elements)

above and a minimum of one bottom layer below the chamber enables advantages including but not limited to using the minimum number of layers necessary to define the chamber (thus, reducing cost), while ensuring contact between a face of one or more of the physical element sensors and the fluid in the chamber. The substrate layer may generally be parallel to the layers below the chamber, except to the extent of out-of-plane oscillations of the one or more physical elements linked to the substrate layer, during which the physical elements are deformed from a parallel configuration. In another embodiment of the invention, the top surface of the chamber is comprised of at least a portion of the substrate layer with one or more physical elements linked to it. When introduced into the chamber, the fluid sample is in contact with one or more physical elements and occupies at least a volume in the vicinity of the region below the one or more physical elements and above the bottom of the chamber and affects the oscillations in the physical elements. Further, in order to define one or more fluidic access pathways to one or more of the physical elements, the fluid sample may also occupy additional volumes in the chamber below regions of the substrate layer that lead toward and/or away from the one or more physical elements. In yet another embodiment of the invention, the fluid flow into the chamber is directed along the length of the suspended beam (i.e. physical element) and occupies a volume at least in the vicinity of the region below the beam and above the bottom of the chamber. In yet another embodiment of the invention, depending on the surface-wetting properties (e.g., contact angle) of the underside of the suspended beam and the bottom surface of the chamber, once introduced the fluid may occupy a volume at least in the vicinity of the region below the beam and above the bottom of the chamber along the beam length, wherein this region is either within or beyond the width of the suspended beam based on the fluid wetting interaction. For example, when the said region is beyond the width of the suspended beam, it may be within a factor of 1.1, 1.2, 1.3, 1.4, 1.5, 2, 3, 4, 5, 6, 7, 8, 9 or 10 of the width of the beam. In another example, when the said region is within the width of the suspended beam, it may be within a factor of 0.01, 0.05, 0.1, 0.2, 0.3, 0.4, 0.5, 0.6, 0.7, 0.8 or 1 of the width of the beam. These embodiments with the fluid occupying a volume at least in the vicinity of the region below the physical element (i.e. suspended beam) and above the bottom of the chamber enable advantages including but not limited to, reducing fluid volume required for testing, improved device sensitivity to measuring physical properties of the fluid by maximizing the surface area of the device (i.e. suspended beam) exposed to the fluid, and avoiding unintended interaction between the fluid and other regions of the chamber.

When a fluid sample is present in the chamber, the effect(s) (e.g., damping) on the oscillations in the physical element, because of a face of the physical element being in contact with the fluid sample in the chamber below it, can be used to determine one or more physical properties of the fluid such as viscosity, viscoelasticity and density. In some embodiments of the invention, the oscillation induced in the physical element can be at a non-resonance frequency. The measurable or quantifiable oscillation characteristics of the physical element include without limitation oscillation amplitude, phase, frequency and quality factor. In all resonating devices, the quality factor is affected by the surroundings; the quality factor of a resonant system changes according to the viscosity, viscoelasticity and density of the media it is in contact with. The amplitude of the oscillating element is proportional to the fluid viscosity; when in contact with a low viscosity fluid, the element will oscillate with much higher amplitude over a narrow frequency range near the natural or fundamental frequency, compared to when in contact with a high viscosity fluid. Introduction of a fluid sample in the vicinity of the physical element causes damping in its oscillation characteristics, and changes in amplitude, phase, frequency and/or quality factor and are indicative of the viscosity, viscoelasticity and density of the fluid. In some embodiments of the invention, the conductive path through the physical element comprises one or more heating elements, including but not limited to for example, one or more resistive track heaters, to control the temperature of the fluid medium in the chamber, and/or one or more sensing elements, to monitor the temperature of the fluid medium in the chamber. In some embodiments of the invention, one or more conductive paths comprising one or more heating elements and/or one or more sensing elements may be disposed on a layer below the chamber to control and monitor the temperature of the fluid medium in the chamber, respectively.

In some embodiments of the invention, when the physical element is in contact with a biological fluid which can undergo a reaction leading to coagulation, the oscillating element is further dampened by the increasing viscosity or viscoelasticity of the fluid sample as it coagulates. This damping effect can be measured periodically (i.e., at two or more time points) to determine the coagulation of the body fluid as a function of time. In some embodiments of the invention, the biological fluid comprises whole blood or plasma. In some embodiments, the blood coagulation is initiated by physical contact with negatively charged substrates or by the addition of blood coagulation-inducing compounds, for example, thromboplastin, and the time to formation of the blood clot can be accurately determined as part of blood tests such as Prothrombin Time (PT), Partial Thromboplastin Time (PTT), Activated Clotting Time (ACT), etc. In some embodiments, the oscillation damping of the physical element can be used to monitor blood viscoelasticity periodically (i.e., at two or more time points) and corresponding viscoelastic parameters can be accurately determined as part of blood tests such as Thromboelastogram (TEG). In other embodiments, the measured blood viscoelastic parameters can be used to detect the presence of one or more anticoagulants in the blood, discriminate between two or more anticoagulants in the blood, and/or determine the concentration of one or more anticoagulants in the blood. In other embodiments, the measured blood viscoelastic parameters can be used to detect the presence of, measure the concentration of, and/or measure the activity of a blood coagulation factor (e.g., Fibrinogen, Thrombin) and/or blood constituent (e.g., red blood cells, platelets). In other embodiments, the measured blood viscoelastic parameters can be used to determine blood clot-specific characteristics (e.g., clot stiffness, fibrinolysis).

As discussed earlier, the fluid characteristics can be determined from oscillation characteristics of the physical element. Alternatively, the entire structure comprised of the physical element and the chamber formed by the substrate and bottom layers, can be oscillated at a corresponding resonance or non-resonance frequency to determine the fluid characteristics such as the fluid density. The additional mass of the fluid once introduced in the chamber dampens the oscillation of the entire structure and subsequently shows reduction in measurable oscillation characteristics such as oscillation amplitude, frequency and Q-factor.

In-Plane Vibration

One method of measuring viscosity and viscoelasticity of a fluid involves trapping the fluid between a fixed and moveable parallel plates or planar structures, and monitoring the drag experienced by the moveable planar structure when it is moved in its own plane at a constant velocity relative to the fixed planar structure. The fluid experiences a true shear stress resulting in a shear strain on the fluid, and the fluid viscosity and viscoelasticity is computed as determined by the ratio of the stress applied to the strain experienced by the fluid.

Miniaturized microacoustic sensors like quartz thickness shear mode resonators (TSM) and surface acoustic wave (SAW) devices have been successfully used as alternatives to traditional viscometers, but these devices measure viscosity at relatively high frequencies and small vibration amplitudes. Since the penetration depth ($\delta_s = \sqrt{\eta/\rho\pi f}$) of the shear waves excited by these sensors are small (due to high frequencies), only a thin film of liquid close to the device is probed. In addition, due to the small penetration depth these sensors are unable to detect the presence and effect of particles (size>$\delta_s$) in complex or non-Newtonian fluids and can only measure the viscosity of the continuous phase of the fluid. Finally, the smaller vibration amplitude in these sensors results in lower measurement sensitivity.

In devices and methods according to the present invention, the physical element can be configured so that the suspended beam has at least one natural or fundamental frequency of vibration corresponding to an in-plane oscillation. When a fluid sample is introduced and confined in the chamber located below the physical element, which is in contact with the fluid, the oscillation induced in the physical element applies a true shear stress to the fluid. By measuring vibration characteristics of the physical element, which can be further translated into the shear rate and shear stress experienced by the fluid, the fluid viscosity and viscoelasticity can be determined. In some embodiments of the invention, the physical element's in-plane oscillation can be tailored to be sensitive to the fluid density and hence, the fluid density can be determined from the damping of oscillation characteristics. This device and methodology offer high-accuracy measurement of the absolute and instantaneous value of the fluid viscosity, viscoelasticity and/or density in a fluid sample.

In one embodiment of the invention, based on the geometric design, structure and material properties of the physical element the oscillation frequency can be relatively low, such as in the range of a few tens of Kilo-Hertz or less (e.g., less than or equal to 30, 25, 20, 15, 10, 5, 4, 3, 2, or 1 kHz), resulting in a relatively large shear penetration depth into the fluid under concern. Also, higher oscillation amplitudes can be achieved resulting in higher sensitivity to fluid viscosity. In another embodiment of the invention, the physical element can have at least two in-plane oscillation modes, one with a low frequency (see above) and the other with high frequency (e.g., more than 30 kHz), thus having two distinct oscillation modes with large and small shear penetration depths, respectively. In a fluid comprising discrete components/additives, including non-Newtonian fluids, the oscillation corresponding to a shear penetration depth smaller than the size of the discrete components/additives can be used to determine the fluid viscosity corresponding to the continuous phase, and shear penetration depth larger than the size of the discrete components/additives can be used to determine the bulk viscosity of the fluid. In some embodiments of the invention, the size of the discrete components/additives can be a number in the range of 0.5 to 500 μm.

"Size" may refer to the hydrodynamic diameter or the largest physical dimension measured along standard Cartesian coordinates. These two in-plane oscillation modes can be induced in the physical element simultaneously or in sequence, thus enabling the measurement of the viscosity of the continuous and bulk phases of complex or non-Newtonian fluids. In some embodiments of the invention, the amplitude of vibration induced in the physical element can be controlled by increasing the amplitude of actuation, consequently controlling the shear rate ($\dot{\gamma}$) applied to the fluid. In some embodiments of the invention, where electromagnetic actuation is employed the amplitude of vibration can be changed by changing the magnitude of current through the conductive path and/or the magnetic field applied. Thus, fluid viscosity at varying shear rates can be determined for complex or non-Newtonian fluids.

In some embodiments, the device can be configured so that the physical element oscillation induces a first acoustic field in the fluid sample with a first shear penetration depth smaller than a threshold value, wherein the threshold value ranges from 0.5 microns to 500 microns, and oscillation at the second oscillation frequency induces a second acoustic field in the fluid sample with a second shear penetration depth greater than the threshold value. In some embodiments, the first and second shear penetration depths differ by at least a minimum amount, which may be a value greater than or equal to 0.5, 1, 2, 3, 4, 5, 10, 15, 20, 25, or 30 microns, or a value ranging from 0.5 to 1, 1 to 2, 2 to 3, 3 to 4, 4 to 5, 5 to 10, 10 to 15, 15 to 20, 20 to 25, or 25 to 30 microns.

In some embodiments of the invention, when a biological fluid such as blood is introduced in the chamber, the two in-plane oscillation modes can have penetration depths greater or smaller than the average size of the red blood cells, which form the discrete component in the sample. In some embodiments of the invention, the two in-plane oscillation modes can have penetration depths greater or smaller than 5 μm, which corresponds to a lower limit of the size of red blood cells. In some embodiments of the invention, the two in-plane oscillation modes can have penetration depths greater or smaller than 10 μm, which corresponds to an upper limit of the size of red blood cells. As discussed above, the two in-plane oscillation modes can be used to measure the viscosity of the plasma (continuous phase) and whole blood (bulk phase) of the blood sample simultaneously or in sequence. In some embodiments of the invention, when a body fluid such as blood is introduced in the chamber, the two in-plane oscillation modes can have penetration depths greater or smaller than the average size of platelets which form the discrete component in the sample. In some embodiments of the invention, the two in-plane oscillation modes can have penetration depths greater or smaller than 2 μm, which corresponds to a lower limit of the size of platelets. In some embodiments of the invention, the two in-plane oscillation modes can have penetration depths greater or smaller than 0.5 μm, which corresponds to a size of some macromolecules or macromolecular assemblies, where the size is defined by the hydrodynamic diameter of the molecule.

The chamber of devices according to the invention defines an internal volume which is suitable for receiving and retaining a fluid sample and is comprised of a substrate layer located above the chamber linked to at least one physical element in contact with the fluid, which is disposed in a manner that allows for the motion or oscillation of the suspended beams. The motion or oscillation can occur in an unimpeded manner, i.e., occupying any of the range of space traversed during the oscillation and does not result in collision or contact of the physical element with other solid material. To be clear, "unimpeded" does not mean "without any resistance at all"; fluid, when present, provides a degree of resistance to or damping of the oscillation, and the beam structure may provide a restoring force when the suspended beam is displaced from its resting position, and the presence of resistance from fluid, restoring force from the beam structure, and the like are entirely consistent with "unimpeded" motion or oscillation as used herein. The chamber is defined by means of substrate and bottom layers positioned above and below the chamber, respectively, such that the physical element (linked to the substrate layer) has a face capable of physical contact with the fluid sample in the chamber; the substrate layer may be formed, patterned, or otherwise assembled or constructed to comprise the one or more physical elements. In some embodiments of the invention, the substrate layer is affixed to the bottom layer by means of intermediary layers in all areas except for the physical element positioned above the chamber, thus effectively restricting motion of the substrate to the physical element alone. In some embodiments of the invention, the chamber can include multiple physical elements in the same substrate or in multiple substrates as part of the plurality of layers in the device.

In another embodiment of the invention, when oscillation is induced in the physical element (i.e. suspended beam) a shear-wave field is induced in the fluid retained in the chamber. The device can be configured such that the distance between the bottom layer and the physical element linked to the substrate layer (D) is configured to have a standing shear-wave field induced in the fluid medium between the bottom layer and the suspended beam during oscillation. In order to have a consistent and reliable standing shear-wave field induced, the distance D can be smaller than or equal to the shear penetration depth of the oscillation ($\delta_s=\sqrt{\eta/\rho\pi f}$). For example, if the fluid medium is water with density of 1 gm/cc and viscosity of 1 cP and an oscillation frequency of 1 kHz, the distance D should be smaller than or equal to $\delta_s$=17.84 µm. The lower the ratio of the distance D to the shear wavelength ($\lambda_s$) of the field induced in the fluid medium in the chamber below the physical element, the higher is the consistency and uniformity of the acoustic field set up in the fluid medium, where $\lambda_s=2\pi\delta_s/\sqrt{2}\ \cos(\delta_t/2)$ where $\delta_s$ is the shear penetration depth ($\delta_s=\sqrt{\eta/\rho\pi f}$) and $\delta_t$ is the loss-tangent angle of the fluid medium.

The distance D can be adjustable or permanently fixed depending on the properties of the surrounding medium. In some embodiments of the invention, the distance D can be adjusted by means of intermediate layers between the substrate layer comprising the physical element and the bottom layer. The intermediate layers can be composed of flexible materials such as foam, polymeric substrates, etc., such that the intermediate layer thickness can be varied by applying compression to the device in the thickness direction. The compression pressure can be applied offline before measurement depending on the fluid sample, or in real-time with the fluid under test introduced into the chamber, alongside monitoring the standing shear-wave field induced in the fluid. In some embodiments of the invention, the distance D can be adjusted by physically moving the bottom layer closer to or farther away from the physical element, or vice-versa, using an automated assembly, followed by filling of the region around the physical element between the substrate layer containing the physical element and the bottom layer in order to form the chamber. The filling material can be one that can flow and change state from a fluid to a solid including but not limited to epoxy, etc. In some embodiments of the invention, the acoustic field setup in the fluid trapped between the physical element and the chamber walls can be used to not only determine the viscosity of the fluid but also its viscoelastic properties. Also, the presence of the fixed chamber walls close to the oscillating physical element offers additional benefits for high accuracy monitoring of the change in physical properties of the fluid as a function of time during gel formation.

In some embodiments of the invention, when a biological fluid such as blood is introduced in the chamber and undergoes a coagulation reaction, the blood clot formed between the physical element and the chamber walls can be used to compute the viscoelastic properties of the blood clot. In some embodiments of the invention, the viscoelastic properties of blood undergoing coagulation can be monitored as a function of time, and corresponding viscoelastic parameters can be accurately determined as part of blood tests such as Thromboelastogram (TEG). In other embodiments, the measured blood viscoelastic parameters can be used to detect the presence of one or more anticoagulants in the blood, discriminate between two or more anticoagulants in the blood, and/or determine the concentration of one or more anticoagulants in the blood. In other embodiments, the measured blood viscoelastic parameters can be used to detect the presence of, measure the concentration of, and/or measure the activity of a blood coagulation factor (e.g., Fibrinogen, Thrombin) and/or blood constituent (e.g., red blood cells, platelets). In other embodiments, the measured blood viscoelastic parameters can be used to determine blood clot-specific characteristics (e.g., clot stiffness, fibrinolysis).

Out-Of-Plane Vibration

In another embodiment of the invention, the suspended beam (i.e. physical element) can have at least one natural or fundamental frequency of vibration corresponding to an out-of-plane oscillation. When a fluid sample is introduced and confined in a chamber, with the physical element located above the chamber and in contact with the fluid, the oscillation characteristics of the suspended beam are damped. The density of the fluid can be determined by monitoring the oscillation characteristics including but not limited to oscillation amplitude, phase, frequency and quality factor. The oscillation characteristics may be measured as a change in the respective characteristic upon addition of the fluid sample to the chamber. In addition, the physical element's out-of-plane oscillation can be tailored to be sensitive to the fluid density and hence, the fluid density can be determined from the damping of oscillation characteristics. In some embodiments of the invention, the fluid density measured can be used to identify the concentration of at least one discrete component/additive in a fluid. The discrete components/additives can be, for example, macromolecules, macromolecular complexes (e.g., cytoskeletal filaments), red blood cells, platelets, particulates or solid-phase objects. In some embodiments of the invention, the physical element oscillation can be configured for measurement of the density of the continuous phase and bulk phase of the fluid independently using the same or different resonance oscillation modes of the physical element.

In another embodiment of the invention, the physical element can enable the measurement of the fluid's continuous phase viscosity, bulk viscosity and density. In some embodiments of the invention, a standardized measure of bulk viscosity of a fluid can be determined as a function of one or more of viscosity of continuous phase, bulk phase, fluid density and concentration of discrete component/additive (if any). Further, the static or dynamic viscoelastic properties of a fluid as a function of time can be determined from the measured (or standardized measures) viscosities of the fluid at different applied shear rates using various theoretical or empirical models. For example, the bulk viscosity measured at varying shear rates can be used with Casson's model, given by $\eta=(\sqrt{\tau_y}+\sqrt{k\dot{\gamma}})/\dot{\gamma}$ where $\tau_y$ is the yield stress of the fluid, $\dot{\gamma}$ is the shear rate applied to fluid and k is a constant, in order to determine a value for $\tau_y$ and k by statistical methods such as regression analysis.

In another embodiment of the invention, where the fluid under test is blood introduced into the chamber, the physical element can be used to measure the plasma viscosity ($\eta_{plasma}$, continuous phase), whole blood viscosity ($\eta_{WBV}$, bulk phase) and blood density when exposed to a blood sample. The blood density measured can be used to identify the concentration of red blood cells or hematocrit (Hct) in the sample. Since whole blood viscosity is highly dependent on the plasma viscosity and hematocrit, in order to identify the normalcy or abnormality of blood viscosity of different individuals the blood viscosity needs to be standardized or corrected to a fixed hematocrit (0.45 is generally used). The formula for the standardized or corrected whole blood viscosity at a fixed hematocrit of 0.45 is given by—

$$\left(\frac{\eta_{WBV-0.45}}{\eta_{plasma}}\right)=\left(\frac{\eta_{WBV-Hct}}{\eta_{plasma}}\right)^{0.45/Hct}$$

where $\eta_{WBV-0.45}$ is the standardized or corrected whole blood viscosity at a hematocrit of 0.45, $\eta_{WBV-Hct}$ is the whole blood viscosity at hematocrit Hct, and $\eta_{plasma}$ is the plasma viscosity.

In another embodiment of the invention, the chamber along with the substrate layer comprising the physical element can be incorporated in a disposable test strip. The chamber is assembled to have the one or more physical elements in the substrate layer suspended above the chamber, with a face capable of physical contact with the fluid sample in the chamber underneath, while another part of the substrate layer is affixed to the bottom layer below the chamber, as part of a plurality of layers stacked to form the test strip. Further, the chamber can be comprised of a plurality of layers patterned/formed in order to have its walls positioned closely together to form a capillary. The materials chosen to create the surfaces of the chamber can be selected to provide a low surface tension and/or contact angle (e.g., less than or equal to 45 degrees) that allows the chamber to fill by a capillary action. These materials are selected as they enhance liquid filling without interfering with the reaction. Examples of such materials will be well known to the person skilled in the art. In some embodiments of the invention, the substrate and bottom layers of the chamber can comprise a plurality of components, including but not limited to electrically conductive paths to perform electrochemical analysis and/or, to detect the presence of an analyte in the fluid and/or the fluid itself in the chamber. In some embodiments of the invention, the electrically conductive paths can be used to perform electrochemical detection of sugar levels in the blood sample introduced into the chamber [13]. In some embodiments of the invention, the substrate and bottom layers can further comprise electrically conductive paths which contain one or more heating elements, such as resistive track heaters, and/or one or more temperature sensors, to control and monitor the temperature of said chamber, respectively.

In some embodiments, a fluid sample may be introduced into the chamber wherein the fluid sample begins undergoing a chemical reaction soon after its addition. For example, the chamber may contain an agent that reacts with the sample once it is present, or an agent can be added to the sample once it is present, or one or more of the surfaces of the chamber may promote or catalyze a reaction in the fluid sample. When a fluid is introduced and confined to the chamber housed inside the test strip, the oscillation characteristics (including but not limited to amplitude, phase, frequency, Q-factor, etc.) of the physical element will generally stabilize momentarily, before further changes take place due to the chemical reaction, allowing for rapid determination of physical characteristics of the fluid. The fast response time of the sensor can also allow for the accurate identification of the time at which the fluid sample was introduced into the chamber.

The substrate layer comprising the physical element can be made of any suitable inert material and may be selected from amongst others: polymers such as polyester (PET), plastics, etc. The substrate layer can be fabricated using mass manufacturing methods including but not limited to roll-to-roll continuous flow manufacturing. The physical elements can be formed or patterned by etching, laser treatment or by mechanical punching (for e.g., using a die) of the substrate layer. The electrically conductive paths through the physical elements can be made by means of patterned conductive paths on the substrate layer that form circuits such as in the case of printed circuit boards. The conductive circuits can be of any suitable conductive material and may be selected from, but not limited to conductive polymers or inks, gold, platinum, copper or silver. The conductive paths can be patterned by several methods such as laser ablation, or by screen- or inkjet-printing. Further, the conductive paths can be insulated from the fluid by deposition of insulating layers on the conductive paths or, have the conductive layer embedded within the substrate layer comprising the physical element.

In some embodiments of the invention, the conductive paths can be exposed to the fluid allowing for electrochemical analysis and/or, detection of the presence of an analyte in the fluid and/or the fluid itself in the chamber. In some embodiments of the invention, the conductive paths can be used to perform electrochemical detection of sugar levels in a blood sample introduced into the chamber. The conductive paths would serve to form a closed electrical path through the physical element. In some embodiments of the invention, the substrate comprising the physical element can be made of a substantially or fully metallic material also serving the additional functional purpose of an electrically conductive path through the physical element.

In other embodiments, the physical element is not substantially metallic. For example, the metal content of the physical element may be less than 50%, 40%, 30%, 20%, 10%, 5%, or 1% by weight or volume. Configurations of the device in which the physical element is not substantially metallic can provide beneficial properties. For example, the substrate can be made of polyester and the conductive paths can be formed by printing conductive ink onto the polyester substrate. Use of a physical element which is not substantially metallic makes it possible to control the geometry of the polyester substrate and the conductive paths independently, consequently enabling greater control over the oscillation characteristics of the physical element than if the element were substantially metallic. Additionally, polyester, being flexible, is compatible with high-volume roll-to-roll continuous flow manufacturing processes, which can be beneficial to the cost-effective manufacturing of the substrate layer, e.g., as part of a disposable test strip.

In some embodiments of the invention, the substrate layer on which the physical element is disposed can be patterned by laser cutting a sheet of polyester, onto which the conductive path is printed in a specific pattern to provide conductivity through the physical element. Conductive inks including but not limited to silver-ink and Palladium-ink can be used for printing the conductive path on the substrate layer.

In certain embodiments, a series of edge connectors on the disposable strip could be provided to allow direct contact or connection between a test meter and the physical elements. An additional purpose of the conductive circuit would be to activate the device in readiness to receive a fluid sample, by means of bridging contacts provided by the edge connectors. Alternatively, the physical elements could be excited and/or monitored by non-contact means such as acoustic wave amplitude reflection, light beams or radio frequency. The separate layers of the test strip could be fabricated and aligned such that no further trimming or adjustment to their size and/or outer peripheral surface would be necessary following assembly of the test strip. Alternatively, a plurality of test strips could be produced simultaneously by fabricating and aligning separate layers of the test strip and, following assembly, trimmed to the desired size and shape of the individual disposable test strips.

In another embodiment of the invention, the fluid under test is a biological fluid, in particular blood. The chamber can be provided with one or more reagents comprising at least one blood clotting agent in an amount suitable to induce coagulation of a blood sample in the chamber. In some embodiments of the invention, the reagent is present in dry form in the chamber. The reagent can be added to the chamber before or after completion of assembly of the strip. Further, the reagent can be provided on the chamber-facing face of the physical element of the substrate layer located above the chamber. In some embodiments of the invention, the reagent is added to the chamber prior to or after the introduction of blood. In some embodiments of the invention, the reagent is comprised of one or a combination of anticoagulants (such as Heparin, Warfarin, etc.), viscosity-changing molecules (such as Dextran) and coagulation factor molecules that can induce coagulation. Generally, coagulation factor molecules include naturally occurring or synthesized compounds that either promote or inhibit blood coagulation including but not limited to Factor I, II, III, IV, V, VI, VII, VIII, IX, X, XI, XII, XIII, von Willebrand factor, prekallikrein, high-molecular-weight kininogen, fibronectin, antithrombin III, heparin cofactor II, protein C, protein S, protein Z, protein Z-related protease inhibitor, plasminogen, alpha 2-antiplasmin, tissue plasminogen activator (tPA), urokinase, plasminogen activator inhibitor-1 (PAI1), plasminogen activator inhibitor-2 (PAI2) and cancer procoagulant. Generally, "viscosity-changing molecules" include compounds that alter the viscosity of blood by at least 0.001 cP upon introduction into blood present in the chamber. In other embodiments, the above-mentioned reagents can be present in the fluid as it is introduced into the chamber and need not necessarily be present in the device as it stands. For example, a reagent could be present in a blood sample as a result of having been administered to the individual who supplied the blood. In another embodiment, the device comprises multiple chambers in which one or more of the reagents is provided in one or more chambers, accommodating at least one substrate with one or more physical elements suspended above the chambers and having a face capable of physical contact with the fluids in the chambers. Further, the same blood sample can be directed and split into multiple microfluidic paths leading to the different chambers in the device. Thus, blood coagulation can be induced and monitored at discrete regions of the device in the same blood sample.

In some embodiments of the invention, when a biological fluid such as blood is introduced in the chamber, two in-plane oscillation modes of the physical element can have penetration depths greater or smaller than the average size of red blood cells which form a discrete component in the sample. In some embodiments of the invention, the two in-plane oscillation modes can have penetration depths greater or smaller than 5 µm, which corresponds to an approximate lower limit of the size of red blood cells. The two in-plane oscillation modes can be used to measure the viscosity of the plasma (continuous phase) and whole blood (bulk phase) of the blood sample simultaneously or in sequence. In some embodiments of the invention, when a biological fluid such as blood is introduced in the chamber, the two in-plane oscillation modes can have penetration depths greater or smaller than the average size of platelets which form a discrete component in the sample. In some embodiments of the invention, the two in-plane oscillation modes can have penetration depths greater or smaller than 2 µm, which corresponds to a lower limit of the size of platelets. In some embodiments of the invention, the two in-plane oscillation modes can have penetration depths greater or smaller than 0.5 µm, which corresponds to the approximate size of some macromolecules and/or macromolecular complexes. As discussed earlier, the two penetration depths may differ by at least a minimum amount or by an amount in a given range.

In another embodiment of the invention, where the fluid under test is blood introduced into the chamber, the physical element is configured to measure the plasma viscosity ($\eta_{plasma}$, continuous phase), whole blood viscosity ($\eta_{WBV}$, bulk phase) and blood density when exposed to a blood sample. The blood density measured can be used to identify the concentration of red blood cells or hematocrit (Hct) in the sample. Since whole blood viscosity is highly dependent on the plasma viscosity and hematocrit, in order to identify the normalcy and abnormality of blood viscosity of different individuals the blood viscosity needs to be standardized or corrected to a fixed hematocrit (0.45 is generally used).

In some embodiments of the invention, the biological fluid is comprised of blood or plasma and coagulation can be initiated by physical contact to negatively charged substrates or exposure to blood coagulation-inducing compounds including but not limited to thromboplastin and kaolin. Thus, a blood coagulation-inducing compound such as thromboplastin may be present in a device according to the invention, including before addition of blood or plasma, and used in methods according to the invention. Alternatively, the blood coagulation-inducing compound such as thromboplastin may be added to blood or plasma before or after insertion into the chamber. The plasma, whole blood viscosity, viscoelasticity and/or density of the sample can be monitored before, during and/or after the coagulation reaction. Further, the time to formation of a blood clot can be determined as part of blood tests including but not limited to Prothrombin Time (PT), Partial Thromboplastin Time (PTT), Activated Clotting Time (ACT), etc. In some embodiments of the invention, when a biological fluid such as blood is introduced in the chamber and undergoes a coagulation reaction, the blood clot formed between the physical element and the chamber walls can be used to measure the viscoelastic properties of the blood clot. In some embodiments of the invention, the viscoelastic properties of blood undergoing coagulation can be monitored as a function of time and blood tests such as a Thromboelastogram (TEG) can be performed. In some embodiments of the invention, the hematocrit computed in the blood sample by way of the measured blood density can be used to calibrate the above-mentioned blood coagulation tests (PT, PTT, ACT, TEG, etc.) performed.

In some embodiments of the invention, when a biological fluid such as blood is introduced in the chamber and undergoes a coagulation reaction, the damping of oscillation characteristics in one or more physical elements in the substrate layer can be used to determine the real-time viscoelasticity of blood as it clots. The measurable or quantifiable oscillation characteristics of the physical element include without limitation oscillation amplitude, phase, frequency and quality factor. In some embodiments of the invention, the oscillation of one or more physical elements can be either in-plane or out-of-plane. In some embodiments of the invention, when the oscillation corresponds to a natural or fundamental resonance frequency (or its harmonic) of the physical element, the oscillation characteristics are determined by actuating and detecting the oscillation in the physical element in a range of frequencies in the vicinity of the resonance frequency. These oscillation characteristics such as amplitude and phase can be measured as a function of frequency in the vicinity of the resonance frequency (for e.g., amplitude vs. frequency and phase vs. frequency scans), which can be monitored and recorded periodically (i.e., at two or more time points) to determine different aspects of the blood coagulation cascade. These oscillation characteristics' frequency scans monitored periodically over time can be used to perform tests such as a Thromboelastogram (TEG), wherein a characteristic wineglass shaped viscoelastic curve and parameters can be extracted. The TEG-like viscoelastic parameters include but are not limited to clot formation time (R), activated clotting time (ACT), maximum thrombin generation (ThrombinPeak), clot stiffness (G), platelet contraction rate (Plt-Cont), and fibrinolysis rate (Lys-Rate). In some embodiments of the invention, the TEG-like curve and parameters can be extracted in under 10 minutes, due the high-sensitivity of the physical element device and the low blood sample volume required for testing, given that smaller clots are faster to form. This enables a significant advantage over the commercially available TEG systems (e.g., Haemonetics' TEG-5000, 6s and Instrumentation Laboratory's ROTEM) that require up to 30-60 minutes to generate the entire TEG curve and parameters. In some embodiments of the invention, the coagulation test measurement performed using the disposable test strip is insensitive to ambient vibrations (e.g., frequency<100 Hz), since the oscillations in the physical element can be at high frequencies (e.g., in the order of tens, hundreds or thousands of kHz). This enables a significant advantage over the commercially available systems that are vibration sensitive and non-portable. Mathematical models of the viscoelastic oscillation damping of the physical element, which incorporate the different kinetic processes in the blood coagulation cascade, can be used to fit to the data from the oscillation characteristics' frequency scans as a function of time, and thus, enable the extraction of different hemostatic parameters, including but not limited to Time for threshold Thrombin generation (R), rate of catalysis by Prothrombinase or Factor-Xa ($k_2$), rate of catalysis by Thrombin or Factor-IIa ($k_1$), concentration of cleavable Fibrinogen or Factor-I ($C_{fibrinogen}$), concentration of uncleavable Fibrinogen or Factor-I, clot stiffness (G), platelet contraction rate (Plt-Cont), and fibrinolysis rate (Lys-Rate). These measured hemostatic parameters are used to extract the above-mentioned TEG-like viscoelastic parameters and enable the monitoring of the concentration and activity of different coagulation factors (e.g., fibrinogen, thrombin), blood clot-specific characteristics (e.g., clot stiffness G, fibrinolysis rate Lys-Rate), and activity/effect of different blood constituents participating in coagulation (e.g., platelet contraction rate Plt-Cont, effect of red blood cells or hematocrit), as a function of time during the blood coagulation cascade.

In some embodiments of the invention, monitoring the concentration of cleaved fibrinogen as a function of time during the blood coagulation cascade and plotting it by mirroring it about the time axis (for e.g., x-axis is time and y-axis is fibrinogen concentration), can enable the generation of a wineglass shaped viscoelastic curve that is typically outputted in a TEG test. Alternatively, one of the oscillation characteristics (for e.g., amplitude) at one or more oscillation frequencies can be plotted as a function of time and mirrored about the time-axis to generate the typical TEG-like viscoelastic curve. In another embodiment of the invention, monitoring the concentration of thrombin as a function of time during the blood coagulation cascade, can enable the measurement of time for threshold thrombin generation (for e.g., clot formation time R), time to maximum thrombin generation (for e.g., ACT), maximum thrombin concentration (for e.g., ThrombinPeak), and area under thrombin generation curve at different time durations (for e.g., endogenous thrombin potential ETP), and thus, be used to perform tests such as a thrombin generation assay (TGA). In yet another embodiment of the invention, the thrombin concentration can be extracted by monitoring the rate of increase in cleaved fibrinogen concentration. In yet another embodiment of the invention, thrombin concentration and/or time for threshold thrombin generation or clot formation time R can be monitored to detect the presence and quantify the effect of one or more anticoagulants in the blood, including but not limited to heparin and Factor-Xa inhibitors (e.g., Rivaroxaban, Apixaban).

In some embodiments of the invention, monitoring the blood clot-specific characteristics such as clot stiffness G as a function of time during the blood coagulation cascade and plotting it by mirroring it about the time axis (for e.g., x-axis is time and y-axis is clot stiffness G), can enable the generation of a wineglass shaped viscoelastic curve that is typically outputted in a TEG test. In another embodiment of the invention, clot stiffness G can be monitored to measure the concentration and quantify the effect of one or more coagulation factors, including but not limited to cleavable Fibrinogen or Factor-I and Factor-XIIIa. In yet another embodiment of the invention, the clot stiffness G can be expressed a function of the cleaved fibrinogen concentration (e.g., G may be proportional to $(C_{fibrinogen})^2$). In yet another embodiment of the invention, the clot stiffness G, concentration of cleaved fibrinogen, and/or time for threshold thrombin generation or clot formation time R can be monitored to detect the presence and quantify the effect of one or more anticoagulants in the blood, including but not limited to Factor-IIa inhibitors (e.g., Dabigatran). In yet another embodiment of the invention, monitoring the activity/effect of different blood constituents (e.g., platelets, red blood cells or hematocrit) participating in coagulation as a function of time during the blood coagulation cascade, can enable the measurement of concentration of these blood constituents (e.g., platelets) and quantification of their corresponding effect on blood coagulation processes, such as platelet contraction and effect of red blood cells on clot stiffness. In yet another embodiment of the invention, the platelet contraction rate Plt-Cont can be monitored to detect the presence and quantify the effect of one or more platelet agonists, including but not limited to adenosine diphosphate (ADP), arachidonic acid (AA), collagen, and thrombin receptor activator peptide 6 (TRAP-6), and/or platelet inhibitors, including but not limited to glycoprotein (GP) IIb/IIIa inhibitors (e.g., Abciximab, Eptifibatide), Aspirin®, and Clopidogrel, in the blood and thus, be used to perform tests such as platelet function assays (PFA) (e.g., Roche's Multiplate Analyzer).

In some embodiments of the invention, monitoring the blood clot-specific characteristics such as fibrinolysis rate Lys-Rate as a function of time during the blood coagulation cascade can enable the quantification of blood coagulation processes, such as internal and external fibrinolysis. In another embodiment of the invention, fibrinolysis rate Lys-Rate can be monitored to detect the presence and quantify the effect of one or more additives in the blood, including but not limited to tissue plasminogen activator (tPA) and tranexamic acid (TXA), which affect one or more blood coagulation processes (e.g., external fibrinolysis).

In some embodiments of the invention, the concentration and/or effect of two or more coagulation factors can be monitored to discriminate between the presence of two or more anticoagulants, for example discriminating between factor-Xa (e.g., Rivaroxaban, Apixaban) and factor-IIa (e.g., Dabigatran) inhibitor-based anticoagulants. In another embodiment of the invention, thrombin and cleaved and/or uncleaved fibrinogen concentrations (or their effect on one or more oscillation characteristics) can be monitored to discriminate between the presence of factor-Xa and factor-IIa inhibitor-based anticoagulants in the blood, since factor-Xa inhibitors tend to decrease thrombin concentration but have limited to no effect on cleaved or uncleaved fibrinogen concentration, whereas factor-IIa inhibitors have limited to no effect on thrombin concentration but tend to decrease the cleaved (or increase the uncleaved) fibrinogen concentration, thus allowing for a differential response to enable discrimination between the anticoagulants. In another embodiment of the invention, this differential response to enable discrimination between the anticoagulants can be a metric defined by the ratio of thrombin to cleaved or uncleaved fibrinogen concentrations. In yet another embodiment of the invention, this differential response to enable discrimination between the anticoagulants can be a metric defined by the ratio of one or a combination of oscillation characteristics of the suspended beam sensitive to thrombin concentration, to one or a combination of oscillation characteristics sensitive to cleaved or uncleaved fibrinogen concentration. In yet another embodiment of the invention, following the successful identification of the specific anticoagulant in the blood, the effect of the anticoagulant on clot formation time R can be used to determine the concentration of the anticoagulant, using a pre-determined calibration or anticoagulant dose-response curve for the clot formation time R.

Monitoring or reading of a device according to the invention in order to provide an automated means for determining the viscosity, viscoelasticity and/or density of a fluid sample can be provided by the use of a machine, such as a metering device, which can interact with the sensor device of the invention in a manner which allows for the meter to determine the results of the sample testing. In some embodiments of the invention, the metering device comprises one or more of the following: processor, bus, input interface such as keypad or data port, input interface such as a resistive or capacitive touch-screen display, output interface such as display screen, output interface such as a data port, wired and/or wireless connectivity for input and/or output interface, power supply such as battery or power cord or power receptacle, strip connector interface for providing conductivity, etc. In some embodiments of the invention, where the sensor device is connected to, or engaged with a meter, this provides an automated means for determining the physical characteristics of a fluid including but not limited to viscosity, viscoelasticity and/or density. For example, where the meter is connected to the sensor device, the meter could be releasably/temporarily engaged with the test strip and would have the ability to output the test results, typically by means of a visual display or readout. In addition, where the meter processes the data received from the sensor device, the meter may process this information and apply correction factors which would take into account any batch to batch variability associated with the disposable test strip manufacture.

In some embodiments of the invention, the meter may include electronic components as part of a processor unit which is configured to induce and detect the oscillation of the physical element. When the meter is connected to the sensor device, electrical conductivity is established between the processor unit and the conductive paths through the one or more physical elements in the sensor device. In some embodiments of the invention, oscillation at a particular frequency is induced in the physical element by the processor unit applying a time-varying actuation signal such as a voltage/current corresponding to the oscillation frequency through one or more conductive paths in the physical element. Similarly, a time-varying detection signal, such as a voltage/current, is measured by the processor unit through one or more conductive paths in the physical element in the vicinity of the oscillation frequency. In some embodiments of the invention, when the oscillation corresponds to a natural or fundamental resonance frequency (or its harmonic) of the physical element, the resonance characteristics are determined by actuating and detecting the oscillation in the physical element in a range of frequencies in the vicinity of the resonance frequency, for example, within a factor of 1.5, 2, 3, 4 or 5 of the resonance frequency. The resonance characteristics measured can include but are not limited to resonance amplitude, phase, resonance frequency, Q-factor, etc. In some embodiments of the invention, where the oscillation in the physical element is induced and/or detected using electromagnetism, the actuating signal provided by the processor unit corresponds to a current injected/applied in the range of 100 nA to 10 A, for example, 100 μA to 1 A, through the conductive paths in the physical element in the presence of a magnetic field in the range of 0.001 T to 10 T, for example, 0.01 T to 2 T. Similarly, in some embodiments, the detection signal measured by the processor unit corresponds to a voltage in the range of 0.01 μV to 10 V, for example, 1 μV to 1 V, in the presence of a magnetic field in the range of 0.001 to 10 T or 0.01 T to 2 T. In some embodiments, the amplitude of oscillation induced in the physical element is in the range of 1 nanometer to 100 microns, for example, 10 nanometers to 10 microns. The meter is provided with one or more enclosures to accommodate one or more permanent or variable magnet assemblies (such as an electromagnet) in the vicinity of a connector that provides conductivity to the one or more physical elements in the sensor device. In some embodiments of the invention, the meter is provided with top and bottom halves forming part of a clam-shell based assembly, that allows items including but not limited to the touchscreen display for the input and output interface, connector to the sensor device, the magnet assembly, the processor unit, battery, data port and power cord receptacle to be enclosed in either the bottom or top halves. The top and bottom halves can comprise one or more alignment features that allow for precise assembly and securing or fastening of the two halves using means such as snap-fit assembly, screw-based compression assembly, etc.

In some embodiments of the invention, the meter may include a facility to sample environmental conditions such as temperature, humidity, altitude, atmospheric pressure, etc. and apply a correction factor to the measurement response. In another embodiment of the invention, the meter provides an actuation signal for and measures a detection signal from the oscillations in the physical element in a range of frequencies in the vicinity of the resonance frequency of the physical element and records a scan of the oscillation characteristics as a function of frequency. This frequency scan of the oscillation characteristics can be used as a metric to identify any batch-to-batch variability associated with the disposable test strip manufacture. In yet another embodiment of the invention, the frequency scan of the oscillation characteristics can also be used to detect and monitor the physical element's resonance frequency as a function of time, which can be sensitive to environmental conditions such as a temperature, humidity, etc., and can be used to measure these environmental conditions using a predetermined calibration curve established to enable the same. Additionally, the meter can have a memory facility that would allow previous readings to be stored and recalled, for example to provide a comparison of measurements across two or more dates or times. This feature may be of particular utility in the case of regular testing for monitoring different aspects of the blood coagulation cascade (e.g., anticoagulant levels such as Warfarin, Heparin, etc.). In some embodiments of the invention, in order to calibrate the machine or the individual sensor device, the meter may perform an initial self-test on the disposable strip prior to blood introduction. As blood is introduced into the strip, the change in the fluid properties of the regions around the oscillating physical element results in changes in the oscillation characteristics of the structure, this including the electronics commencing analysis of the blood sample. During a known time period, the analysis is completed and the change in viscosity, viscoelasticity and density of the blood sample before, during and after the coagulation reaction is measured. After a suitable reaction time has passed, an algorithm would be used to convert the measured oscillation characteristics of the physical element into a usable test result.

FIG. 1(a) shows embodiments of a substrate layer of the sensor device of the invention comprising of a physical element, the oscillation of which is suitable for measuring properties of a fluid, including but not limited to viscosity, viscoelasticity and/or density. The fluid can be a biological fluid, the properties of which can be measured before, during and after a chemical reaction. As shown in FIG. 1(a), there is provided a substrate layer assembly 100 for integration into a disposable test strip embodiment of the sensor device of the invention. According to this embodiment, a substrate layer comprises a "physical element" (e.g., as a result of having been machined to form the physical element), which comprises a suspended beam 101 attached to the main body of the substrate layer 102 at each end of its length. The main body of the substrate layer 102 is maintained to be stationary, such that the physical element is configured to perform unimpeded motion or oscillations upon actuation. Also, the main body of the substrate layer 102 can be relatively larger than the suspended beam 101. Two electrical conductors 103 and 104 are formed and patterned on the substrate layer such that there are two independent and isolated conductive paths through the physical element. In an alternative embodiment, a single electrical conductor is formed and patterned on the substrate layer. A magnetic field 105 is applied in a direction perpendicular to the plane of the substrate layer. A time-varying current applied through one or both conductors 103 and 104 in the presence of a constant magnetic field 105 causes the physical element to oscillate in-plane; oscillation may be at the fundamental resonance frequency or at a harmonic resonance frequency of the physical element. Alternatively, a magnetic field 105 applied in the same plane as that of the physical element causes the physical element to oscillate out-of-plane; again, oscillation may be at the fundamental resonance frequency or at a harmonic resonance frequency of the physical element. The oscillation of the electrical conductors 103 and 104 in the presence of the magnetic field 105 electromagnetically induces a "detection voltage", which can be used to ascertain the characteristics of the physical oscillatory movement in the structure. The time-varying current and the detection voltage can be applied and measured, respectively, through either one of the electrical conductors 103 and 104 thus isolating the actuation and detection signals reducing crosstalk or interference. In an alternative embodiment, a single electrical conductor can be formed and patterned on the substrate layer such that both the time-varying current and the detection voltage can be applied and measured through the same electrical conductor. The shape and geometry of the suspended beam 101 and the exact location of its attachment to the main body of the substrate layer 102 may be selected to obtain the optimum sensitivity for the measurement of fluid properties, ascertained by methods such as finite element analysis, empirical analysis, theoretical analysis, trial and error, etc. In addition, the geometry can be consistent with a relatively low or high oscillation frequency, resulting in a relatively large or small shear penetration depths ($\delta_s = \sqrt{\eta/\rho\pi f}$) into the fluid under test, respectively. Also, the amplitude of oscillation induced in the physical element can be controlled by the current applied through either one or both of the conductors 103 and 104 subsequently controlling the shear rate ($\dot{\gamma}$) applied to the fluid.

FIG. 1(b) shows an exploded schematic of the substrate layer assembly for integration into a disposable test strip. A substrate layer 110 is patterned to form a rectangular suspended beam (i.e. physical element) attached to the main body of the substrate layer at each end of its length. The physical element structure may be formed by any appropriate method, such as the conventional methods of laser cutting, CNC milling, chemical etching, stamping, or mechanical punching (for e.g., using a die) of the substrate layer. Independent and isolated patterned conductive tracks 111 and 112 are disposed on the substrate layer 110. These conductive tracks may be disposed by any appropriate method, such as the conventional methods of screen-printing, inkjet-printing, or laser ablation, and can be composed of any suitably conductive and chemically inert material. A patterned insulating dielectric layer 113 is disposed onto the conductive tracks 111 and 112 such that the conductive tracks are completely insulated everywhere except on a region 114 and 115 dedicated to providing electrical connections to the physical element.

Figure 2:
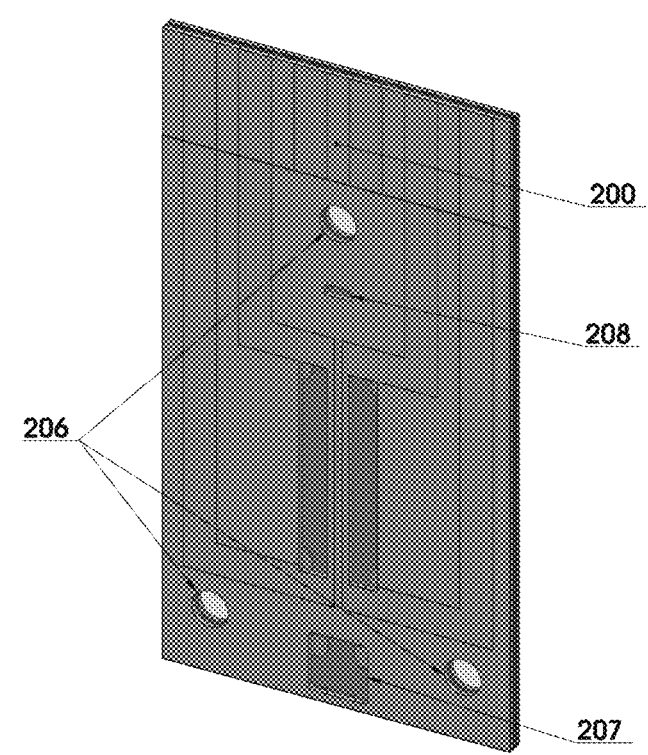
Figure 2:
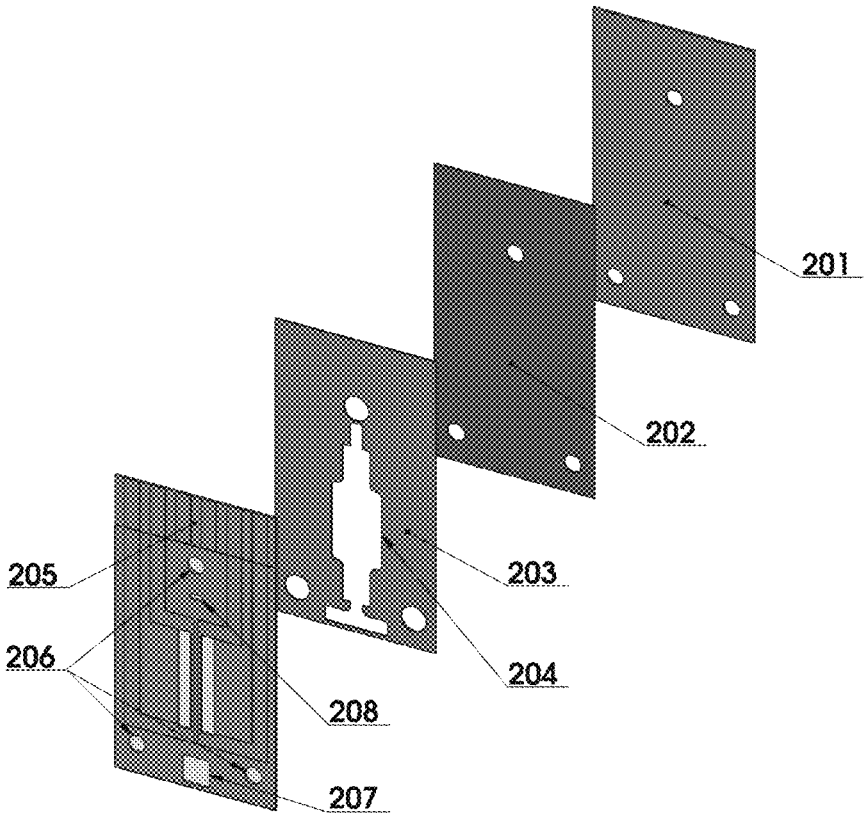
Figure 2:
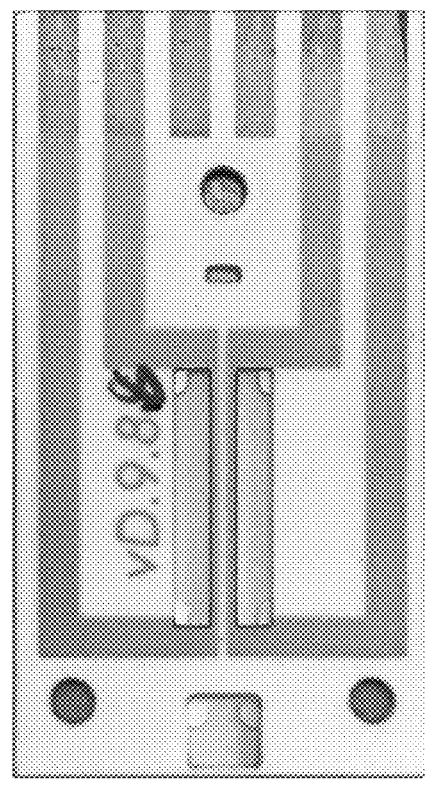
Figure 2:
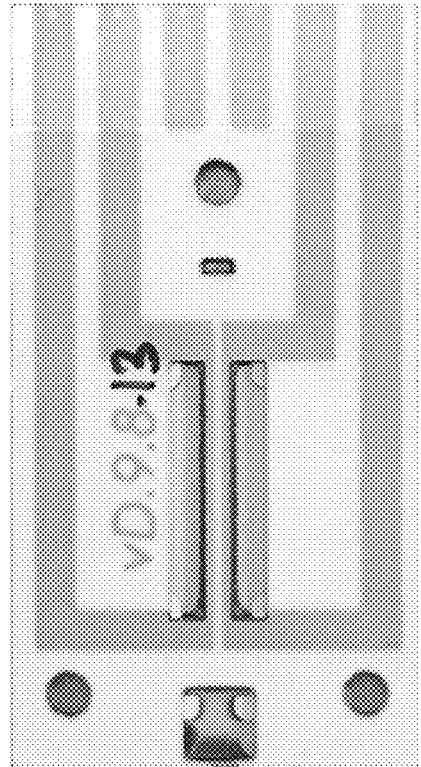

FIG. 2(a) shows a further embodiment of a sensor device in the form of a disposable test strip 200. FIG. 2(b) shows an exploded schematic of the disposable test strip 200 of FIG. 2(*a*). FIGS. 2(*c*) and 2(*d*) show photographs of the assembled disposable test strip without and with a blood sample introduced into the strip, respectively.

The disposable test strip 200 comprises of a base substrate 201, onto which is disposed a hydrophilic wicking layer 202, which may optionally comprise a reagent to facilitate a chemical reaction. The base substrate 201 provides rigidity and improves the overall stiffness of the disposable test strip. A chamber forming layer 203 is disposed onto the hydrophilic wicking layer 202. This chamber forming layer may be formed, e.g., using a patterned pre-cast film, or by laser-cutting, or mechanical punching (for e.g., using a die) a film, or by screen- or inkjet-printing a suitable non-reactive polymeric material. This chamber forming layer is patterned to have a cut-out 204 to form the chamber wall, in the vicinity of the physical element allowing for it to be suspended for unimpeded motion or oscillation above the chamber, with a face of the physical element capable of physical contact with a fluid sample in the chamber. In an alternative embodiment, the reagent to facilitate a chemical reaction in the fluid may be present as a sublayer. In yet another alternative embodiment, a reagent may be provided upon any internal surface of the chamber. The assembled "bottom stack" of layers comprise of the base substrate 201, hydrophilic layer 202 and the chamber forming layer 203. These component layers may be incorporated with adhesives (for e.g., pressure sensitive adhesive) on either or both of their faces to facilitate adhesion between each of the layers to form the assembly. The reagent layer to facilitate the reaction in the chamber could alternatively be loaded onto the exposed surface of the hydrophilic wicking layer 202, after the "bottom stack" of the layers is assembled.

A physical element sensor device assembly 205, such as that detailed in the embodiment depicted in FIGS. 1(*a*) and 1(*b*) may be laminated over the "bottom stack" comprising the base substrate 201, hydrophilic layer 202 and chamber forming layer 203, such that the physical element (or rectangular suspended beam) is suspended above the "chamber", which is defined by the side-walls of the cut-out 204 in the chamber forming layer 203. The physical element sensor device assembly 205 and/or the chamber forming layer 203 may be incorporated with adhesives (for e.g., pressure sensitive adhesive) on their corresponding sides that face each other, in order to facilitate adhesion between the 2 layers to form the disposable test strip 200. The physical element sensor device assembly 205 is patterned to have 3 circular openings 206 as seen in FIG. 2(*a*). These circular openings may be formed by any appropriate method, such as the conventional methods of laser cutting, CNC milling, chemical etching, stamping, or mechanical punching (for e.g., using a die) of the physical element sensor device assembly 205. As seen in FIG. 2(*b*), these 3 circular openings are also patterned in the "bottom stack" of layers at the same exact location as the 3 circular openings 206 on the physical element sensor device assembly 205. The circular openings may be formed in the individual layers of the "bottom stack" or patterned after assembly of these layers to form the "bottom stack" assembly, using any appropriate method, such as the conventional methods of laser cutting, CNC milling, chemical etching, stamping, or mechanical punching (for e.g., using a die). The 3 circular alignment openings on the physical element sensor device assembly 205 and the "bottom stack" layers serve as alignment features to facilitate the alignment between the two assemblies, in order to ensure accurate positioning of the suspended beam above the chamber. The physical element sensor device assembly 205 is further patterned to have 2 rectangular openings 207 and 208, which serve as a port for introducing fluid into the strip and a vent to permit air to escape from the chamber as it is loaded with the fluid sample, respectively. The location of these rectangular openings may be chosen to be above the chamber and within the footprint of the cut-out 204 in the chamber forming layer 203, in order to provide access for the fluid to enter and permit air to escape from the chamber. Further, the opening size, shape and geometry of these rectangular openings may be designed and selected to optimize the fluid introduction and air venting in the chamber.

The distance (D) between the bottom hydrophilic layer 202 and the physical element sensor device assembly 205 as defined by the height of the chamber forming layer 203, and the geometry of the cut-out 204 in the chamber forming layer can be designed and selected to optimize the volume of the chamber, and optimize the fluid introduction and air venting in the chamber. The distance D or the height of the chamber forming layer 203 can be further configured to have the oscillating physical element induce a standing shear-wave field in the fluid medium in the chamber, between the bottom hydrophilic layer 202 and the physical element sensor device assembly 205. In order to have a consistent and reliable standing shear-wave field induced, depending on the fluid properties the distance D can be configured to be smaller than or equal to the shear penetration depth ($\delta_s = \sqrt{\eta/\rho\pi f}$). The lower the ratio of the distance D to the shear wavelength ($\lambda_s$) of the field induced in the medium surrounding the physical element, the higher is the consistency and uniformity of the acoustic field set up in the fluid medium, where $\lambda_s = 2\pi\delta_s/\sqrt{2} \cos(\delta_l/2)$ where $\delta_s$ is the shear penetration depth ($\delta_s = \sqrt{\eta/\rho\pi f}$) and $\delta_1$ is the loss-tangent angle of the medium. The distance D can be configured to be adjustable or permanently fixed depending on the properties of the fluid under test introduced into the chamber. The chamber forming layer 203 can be formed of single or multiple laminated polymeric substrates to tailor the distance D and, incorporated with pressure sensitive adhesives on both sides to facilitate the lamination to the physical element sensor device assembly 205 above and the hydrophilic layer 202 below it. The acoustic field setup in the fluid trapped between the physical element and the chamber walls can be used to not only determine the viscosity of the fluid but also its viscoelastic properties. Also, the presence of the fixed chamber walls close to the oscillating physical element offers additional benefits for high accuracy monitoring of the physical properties of the fluid as a function of time.

The structure and arrangement of the elements of the chamber forming layer 203 may comprise two or more subsidiary, discrete pads arranged in relation to the main body of the chamber forming layers 203 in order to define an opening which allows a fluid sample to be loaded into the chamber, which is defined by an internal volume provided within the sensor device. The fluid may be a biological fluid, for example blood. The arrangement of the two or more subsidiary pads which contribute to the chamber forming layer 203, may be arranged in relation to the main body of the chamber forming layer 203 in order to further provide at least one further channel or opening, typically provided at a different side of the chamber to the main opening. These secondary openings allow for the side filling of liquids, or which, due to the opening being communicable with the central chamber, also permit air to escape from the chamber as it is loaded with a fluid sample.

FIG. 2(*c*) depicts a photograph of the assembled disposable test strip 200 shown in FIG. 2(*a*). FIG. 2(*d*) illustrates a further embodiment depicting a photograph of the assembled disposable test strip with a blood sample introduced into the chamber through the rectangular opening 207 in the physical element sensor device assembly 205 as depicted in FIGS. 2(*a*) and 2(*b*) and affects the oscillations in the physical element (i.e. suspended beam). In this embodiment, the top surface of the chamber is comprised of at least a portion of the substrate layer and a suspended beam is attached to the main body of the substrate layer at each end of its length. The blood sample when introduced into the disposable test strip through the inlet port (i.e. rectangular opening 207 in FIG. 2(*a*)) flows into the chamber under a region of the substrate layer leading up to the suspended beam, followed by the blood flow being directed through the chamber along the beam length while maintaining contact with the underside of the beam, and finally, flowing through the chamber under a region of the substrate layer past the beam leading up to the vent port (i.e. rectangular opening 208 in FIG. 2(*a*)), which permits air to escape from the chamber as it is loaded with the blood sample. Given the good surface-wetting properties (e.g., low contact angle) of the bottom surface of the chamber (i.e. hydrophilic wicking layer 202), the blood sample occupies a region in the chamber below the suspended beam and above the bottom of the chamber along the beam length, wherein this region extends up to or beyond the width of the beam (for example, within a factor of 1.5 of the width of the beam as seen in FIG. 2(*d*)). The bottom surface of the chamber (i.e. hydrophilic wicking layer 202) is disposed with a blood coagulation inducing reagent in the vicinity of a region below the suspended beam. Following the introduction of the blood sample into the disposable test strip, the blood undergoes coagulation as initiated by the reagent and the physical properties of the blood sample (e.g., viscosity, viscoelasticity, density) before, during and after coagulation are determined by periodically monitoring the oscillations of the suspended beam and the corresponding damping experienced by it.

Figure 3:
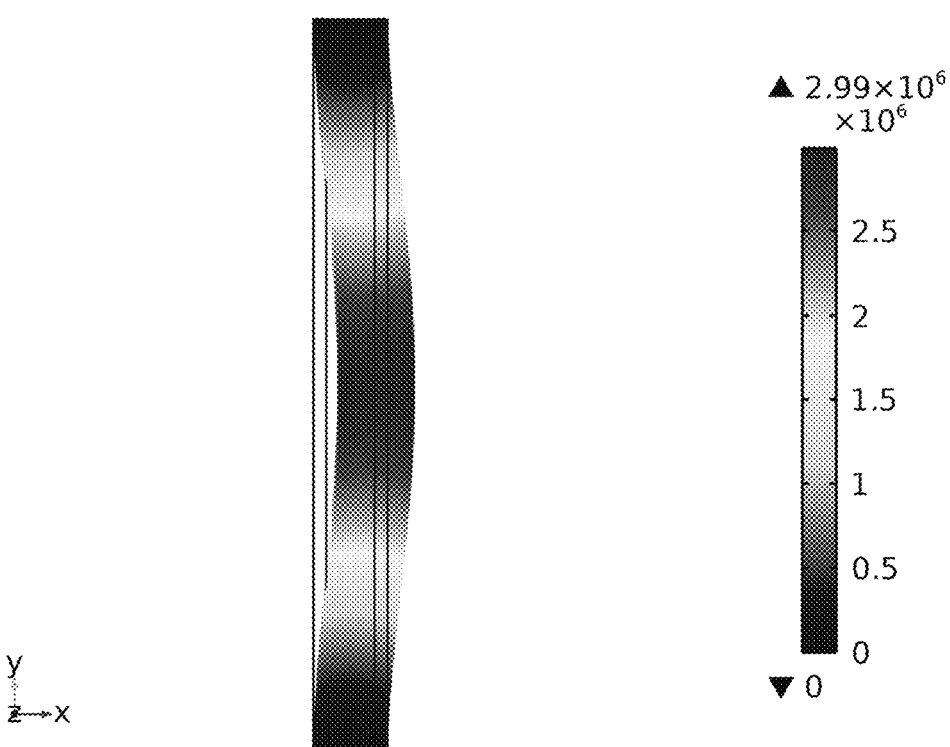
FIG. 3(a) and FIG. 3(b) shows Finite Element Analysis (FEA) simulations of an embodiment of the physical element (as seen in FIG. 1(a)), where FIG. 3(a) portrays its fundamental resonance of in-plane oscillations along the width (x-axis) direction and FIG. 3(b) portrays its fundamental resonance of out-of-plane oscillations along the thickness (z-axis) direction.
Figure 3:
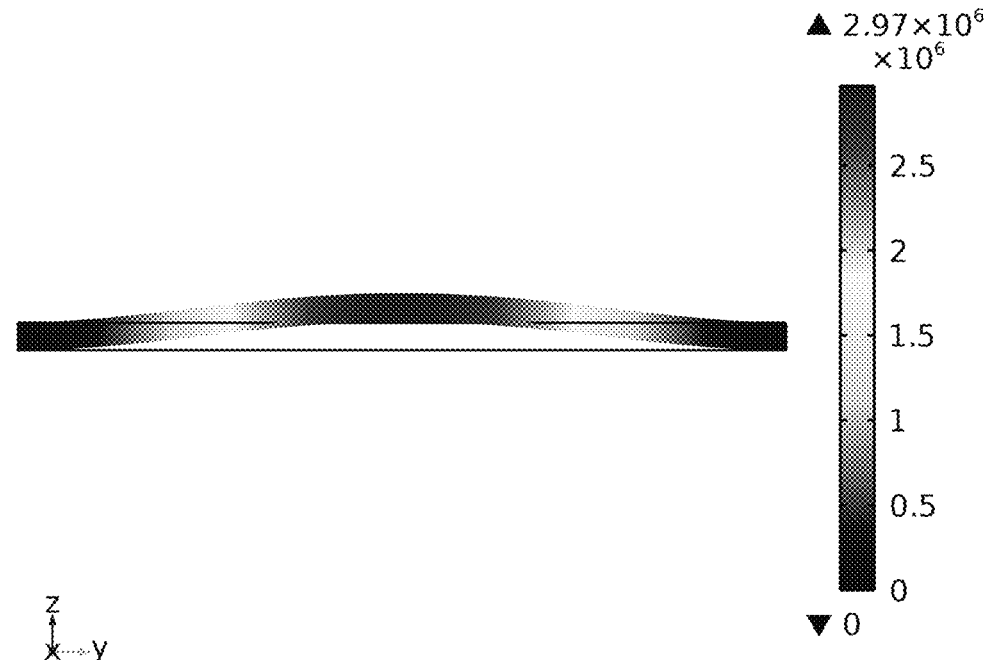

FIG. 3(*a*) shows in-plane oscillations and FIG. 3(*b*) shows out-of-plane oscillations computed using Finite Element Analysis (FEA) simulations induced in a physical element sensor device assembly, such as that detailed in the embodiment depicted in FIGS. 1(*a*) and 1(*b*), and assembled in the form of a disposable test strip such as that detailed in the embodiment depicted in FIGS. 2(*a*) and 2(*b*). FIG. 3(*a*) shows the fundamental resonance of in-plane oscillations in the physical element in the direction of its width (x-axis as seen in the x-y plane or top view), which can be induced by fixing the direction of the magnetic field and varying the direction of the applied current or electric field applied to the physical element or, by varying the direction of the magnetic field and fixing the direction of the applied current or electric field applied to the physical element. FIG. 3(*b*) shows the fundamental resonance of out-of-plane oscillation in the physical element in the direction of its thickness (z-axis as seen in the y-z plane or cross-section/side view), which can be induced by fixing the direction of the magnetic field and varying the direction of the applied current or electric field applied to the physical element or, by varying the direction of the magnetic field and fixing the direction of the applied current or electric field applied to the physical element. In an embodiment, the in-plane (FIG. 3(*a*)) and out-of-plane (FIG. 3(*b*)) oscillations could be induced in a single or a combination of multiple physical elements, located above a single or multiple individual chambers, wherein a face of one or more physical elements is capable of physical contact with the fluid in one or more of the chambers.

FIG. 4 through FIG. 22 are discussed in the Examples section below.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1: Determining the Fluid Characteristics of Ethylene Glycol Aqueous Solutions Using a Physical Element Sensor Device Assembled into a Disposable Test Strip Materials and Methods FIG. 2(*b*) shows an exploded schematic of the disposable test strip 200 of FIG. 2(*a*). The strip was fabricated and assembled using standard diagnostic test strip manufacturing materials made of polyester-based substrates with acrylic adhesives to hold the structure in place.
Bottom Stack Assembly:
The base substrate 201 was composed of a double-sided pressure sensitive adhesive (PSA) layer (0.0032" thick, AR 90445, Adhesives Research, Inc.) laminated on one of its sides to a polyester (PET) layer (0.010" thick, Melinex® 339, Dupont Teijin) to provide structural support. A polyester substrate with a hydrophilic wicking layer on one side 202 (0.0045" thick, ARFlow 90469, Adhesives Research, Inc.) was laminated onto the base substrate, with the hydrophilic side facing away from the base substrate. The chamber forming layer 203, composed of a double-sided PSA (0.005" thick, AR 8939, Adhesives Research, Inc.), was patterned to have a cut-out 204 to form the chamber wall in the vicinity of the physical element and laminated on one of its sides to the hydrophilic layer atop the base substrate, such that the hydrophilic face is exposed through the cut-out. The base substrate 201, hydrophilic layer 202 and the first chamber forming layer 203 layers were also patterned with 3 circular openings at the same exact location as the 3 circular openings 206 on the physical element sensory device assembly 205, in order to serve as alignment features to facilitate the assembly of the substrate layer above the "bottom stack". Finally, the assembled "bottom stack", comprising of the base substrate 201, hydrophilic layer 202 and the first chamber forming layer 203, was patterned to form the footprint of the strip (1.6×3.0 cm$^2$) surrounding the chamber as shown in FIG. 2(*b*).
Physical Element Sensor Device Assembly:
A physical element sensor device was made by screen printing silver-based conductive ink on a polyester substrate (with thickness ranging from 0.003" to 0.0030") to pattern the electrically conductive paths 103 and 104 through the suspended beam 101 and provide electrical pads to connect to the meter as depicted in FIG. 1(*a*). As shown in FIG. 1(*b*), an insulating dielectric layer 113 made of polymeric ink was screen-printed onto conductive tracks 111 and 112 such that the conductive tracks are completely insulated everywhere except on a region 114 and 115 dedicated to providing electrical connections to the meter. The physical element comprised of the suspended beam was patterned by laser machining of the polyester substrate comprised of the conductive paths and dielectric layer. The physical element was fabricated in the shape of a rectangular beam with lengths and widths varying from 0.5 to 20 mm.

Final Disposable Strip Assembly:

The physical element sensor device assembly 205 was laminated over the "bottom stack" assembly, such that the suspended beam was suspended above the chamber, as defined by the hydrophilic layer 202 and the side-walls of the cut-out 204 in the chamber forming layer 203, consequently, the beam forming a portion of the top surface of the chamber. An alignment fixture was used to match the 3 circular openings on the physical element sensor device assembly 205 and the "bottom stack" assembly, in order to facilitate alignment between the two assemblies and ensure accurate positioning of the suspended beam above the chamber. The distance (D) between the hydrophilic surface of the hydrophilic layer 202 and the physical element sensor device assembly 205, as defined by the height of the chamber forming layer 203 (0.005"), and the geometry of the suspended beam in the polyester substrate layer, were selected to have a total fluid volume required for testing to be <10 μl.

Measurement Methodology:

The meter used to perform the measurement was fabricated using standard stereolithography (SLA) processes. It was designed to include a strip receptacle with mechanical guides to ensure consistent and reliable strip insertion and connectivity to an electrical connector at the end of the receptacle. The connector provided electrical connections to the conductive paths through the suspended beam in order to apply and detect time-varying electrical currents/voltages at frequencies in the vicinity of the resonance frequency of the beam. The strip receptacle also comprised of a resistive heater and optionally a thermistor to control and monitor the temperature of the strip during measurement (for e.g., 37° C. for blood testing). The design also included a magnet enclosure for precisely positioning a permanent magnet (sintered, N52 grade, 0.1-0.5 T) relative to the strip in the receptacle, in order to provide in-plane and/or out-of-plane magnetic fields (relative to the strip surface) necessary to enable electromagnetic actuation and detection of oscillations in the suspended beam at frequencies in the vicinity of one or more resonance frequencies of the beam (for e.g., in-plane and out-of-plane resonance). A function generator (Hewlett-Packard HP33120), low-noise pre-amplifier (Stanford Research SR560), DSP lock-in amplifier (Stanford Research SR850), and data acquisition unit (National Instruments USB-6009) were used to apply the current through and measure the "detection voltage" from the suspended beam, with all instruments being controlled through General Purpose Interface Bus (GPIB) wired connectivity to a computer running a Python code that automated the measurement process. In some tests, an off-the-shelf microcontroller based printed circuit board (PCB) system that interfaced with a custom PCB was used to miniaturize and further automate this measurement process.

Electrical current on the order of 0.1-1 A at varying frequencies (detailed in the results section below) was introduced into the physical element or suspended beam through a first conductive path in the presence of a magnetic field (0.1 to 0.5 T). When considering the magnetic field perpendicular to the suspended beam (along z-axis in FIG. 3(*a*)), in-plane motion in a direction perpendicular to the long edge of the rectangular beam (along x-axis in FIG. 3(*a*)) and corresponding to the fundamental frequency of resonance was induced when the electrical current was applied at or near that frequency. When considering the magnetic field parallel to the suspended beam and perpendicular to its long edge (along x-axis in FIG. 3(*b*)), out-of-plane motion in a direction perpendicular to the rectangular beam (along z-axis in FIG. 3(*b*)) and corresponding to the fundamental frequency of resonance was induced when the electrical current was applied at or near that frequency. The oscillation characteristics of the suspended beam viz. amplitude, phase, frequency and quality factor were measured by monitoring the "detection voltage" induced via electromagnetic induction at varying frequencies through the second conductive path running through the suspended beam. These oscillation characteristics such as amplitude and phase of the "detection voltage" were measured as a function of frequency in the vicinity of the resonance frequency (for e.g., amplitude vs. frequency and phase vs. frequency scans), which was monitored and recorded to measure their response to the physical properties to varying fluid types (in this example, ethylene glycol solutions).

Figure 4:
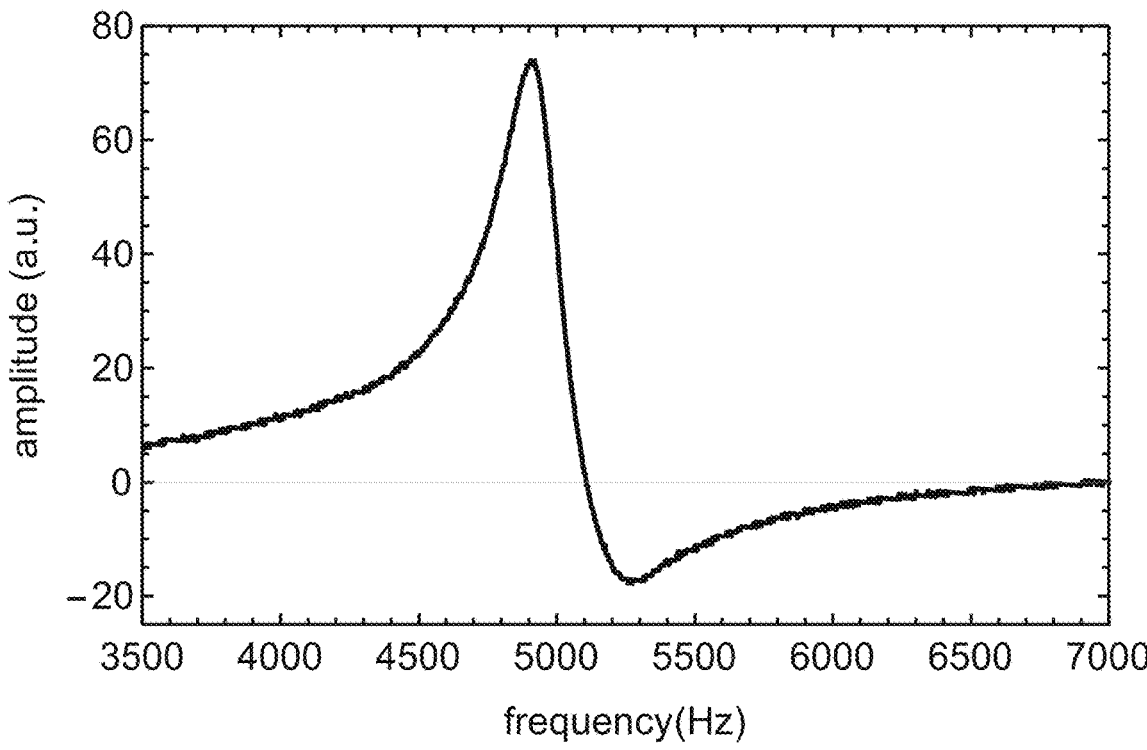
FIG. 4(a) shows an example of a single amplitude frequency scan (from 3500 to 7000 Hz) of a physical element undergoing in-plane oscillations with air present in the chamber, to measure a resonance frequency of 4907 Hz.
FIG. 4(b) shows an example of a single amplitude frequency scan (from 750 to 3250 Hz) of the same physical element undergoing out-of-plane oscillations with air present in the chamber, to measure a resonance frequency of 1374 Hz.
Figure 4:
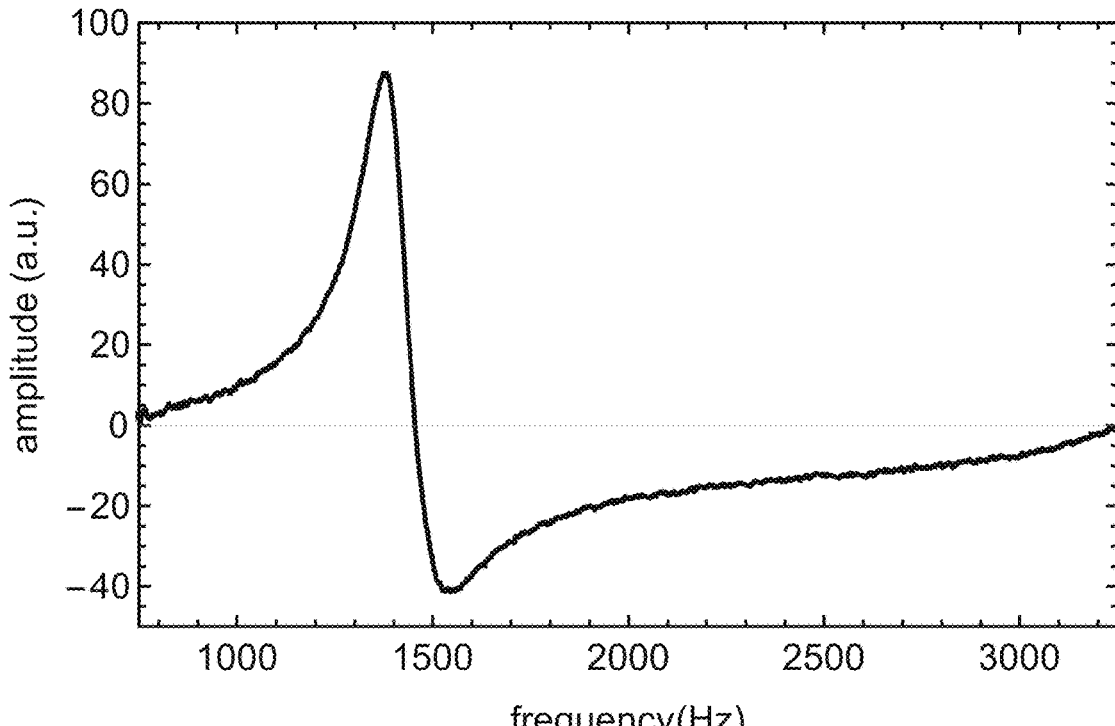
Figure 5:
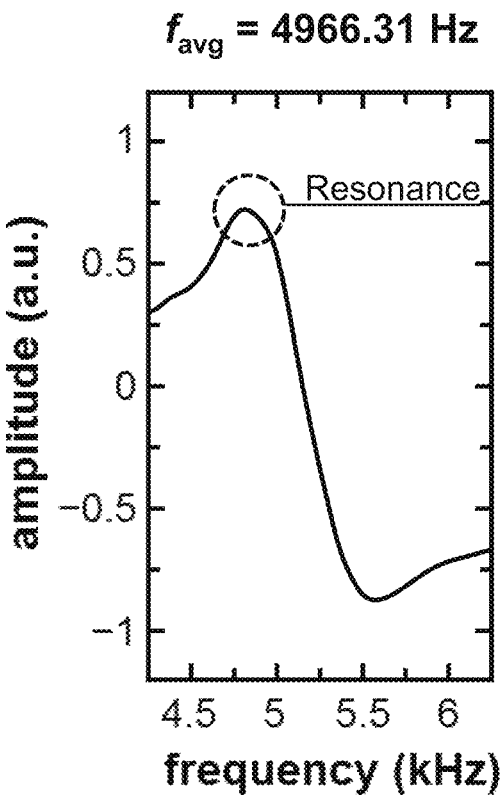
FIG. 5(a) shows an example of a set of normalized amplitude frequency scans of the physical element in multiple strips and FIG. 5(b) shows the statistical binning of the square roots of their respective resonance frequencies.

Sensor Characterization:

Prior to fluid testing, multiple disposable test strips were produced and the oscillation amplitude and phase of their respective suspended beams in air were recorded using the meter (as described above). An example of an amplitude frequency scan in air for in-plane and out-of-plane oscillation of the physical element is shown in FIGS. 4(*a*) and 4(*b*), respectively. In this specific example, the frequency sweep for the in-plane and out-of-plane oscillations were performed in the vicinity of 3500 to 7000 Hz and 750 to 3250 Hz to measure a resonance frequency of 4907 Hz and 1374 Hz, respectively. In order to measure the strip-to-strip consistency in performance, amplitude frequency scans of the in-plane oscillation in beams from multiple strips were normalized and their respective resonance frequencies were identified. The square roots of these resonance frequencies were used as a metric for strip-to-strip consistency for measuring fluid properties, which were statistically binned to identify the strip-to-strip variance. An example of a set of normalized amplitude frequency scans of the physical element in multiple strips and the statistical binning of the square roots of their respective resonance frequencies is shown in FIGS. 5(*a*) and 5(*b*), respectively. In this specific example, 192 disposable test strips were tested, and the square root of resonance frequency metric exhibited an average and standard deviation of 70.46 and 1.19 $Hz^{1/2}$, respectively, with a coefficient of variance (CV) of 1.68%.

Fluid Testing Procedure:

Ethylene glycol solutions were prepared using de-ionized water in varying concentrations ranging from 0 to 40.38% as shown in Table I. The solutions were prepared in 20 ml de-ionized water and corresponding volume of ethylene glycol solutions concentrations. The fluid sample, when introduced into the assembled disposable test strip through the inlet port (i.e. rectangular opening 207 in FIG. 2(*a*)), wicked into the chamber under the region of the substrate layer leading up to the suspended beam, followed by the fluid flow being directed through the chamber along the beam length while maintaining contact with the underside of the beam (at or slightly beyond its width), and finally, flowing through the chamber under the region of the substrate layer past the beam leading up to the vent port (i.e. rectangular opening 208 in FIG. 2(*a*)), which permits air to escape from the chamber as it is loaded with the fluid sample.

TABLE I

| Ethylene Glycol (v/v) [%] | Viscosity (cP) | Density (gm/cc) |
|---|---|---|
| 10 | 1.9903 | 1.03508 |
| 16.22 | 2.7938 | 1.05178 |
| 22.5 | 3.711 | 1.06479 |
| 40.38 | 6.8247 | 1.08806 |

Figure 6:
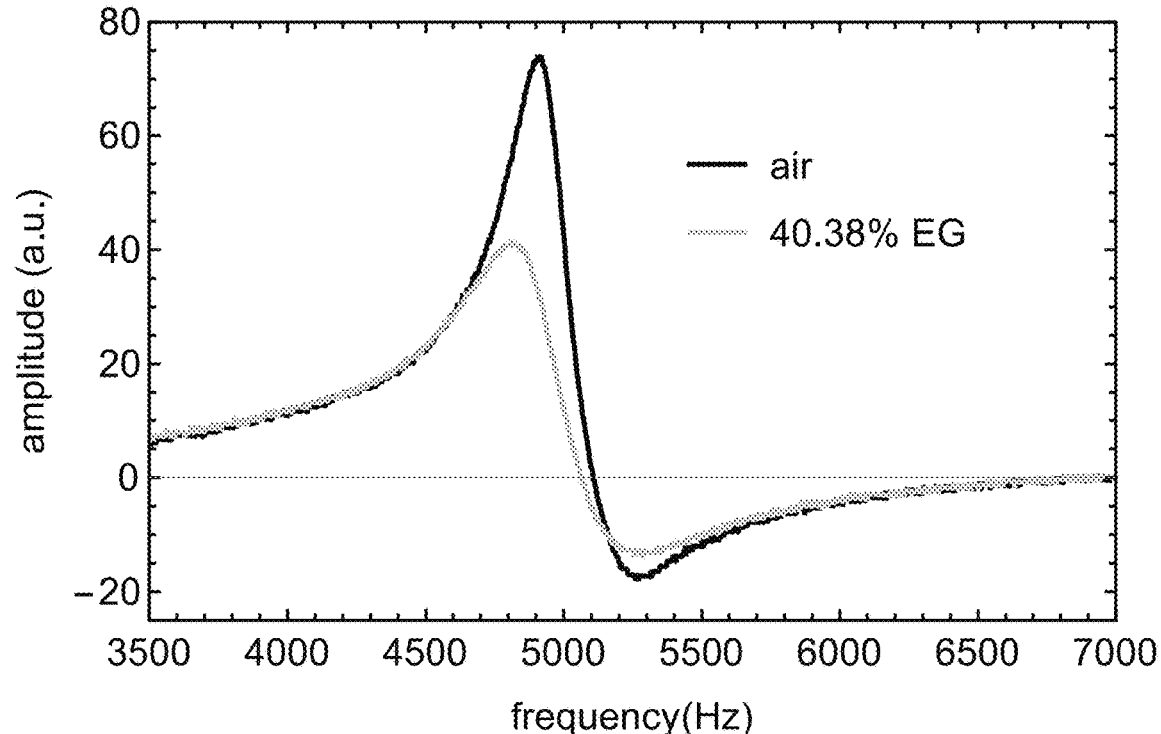
FIG. 6 shows an example of an amplitude frequency scan for in-plane oscillation of the physical element in air and in contact with 40.38% v/v ethylene glycol (EG) solution.
Figure 7:
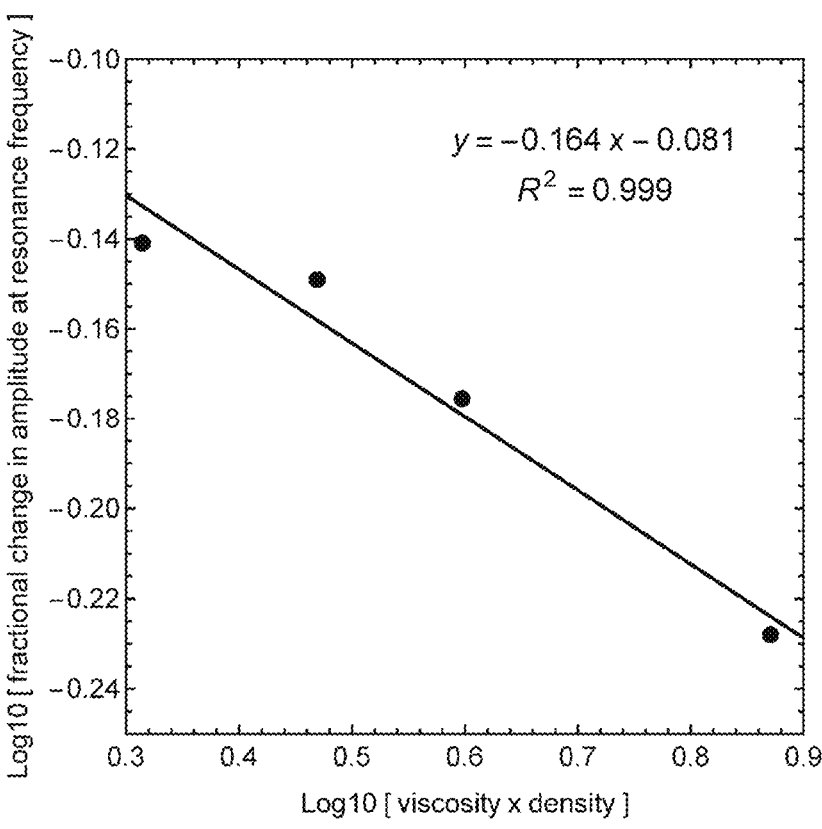
FIGS. 7(a), (b) and (c) show examples of three graphs illustrating the relationship between fluid properties and response of the physical element undergoing in-plane resonance oscillations i.e. amplitude (FIG. 7(a)), frequency (FIG. 7(b)) and quality factor (FIG. 7(c)) for ethylene glycol solutions in de-ionized water.
Figure 7:
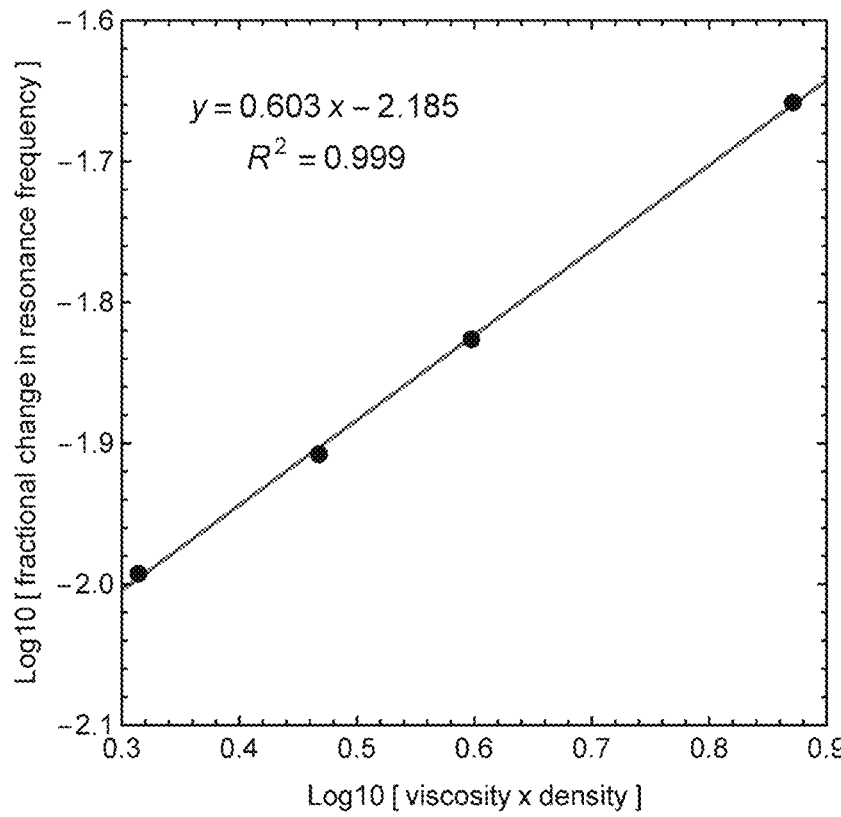
Figure 7:
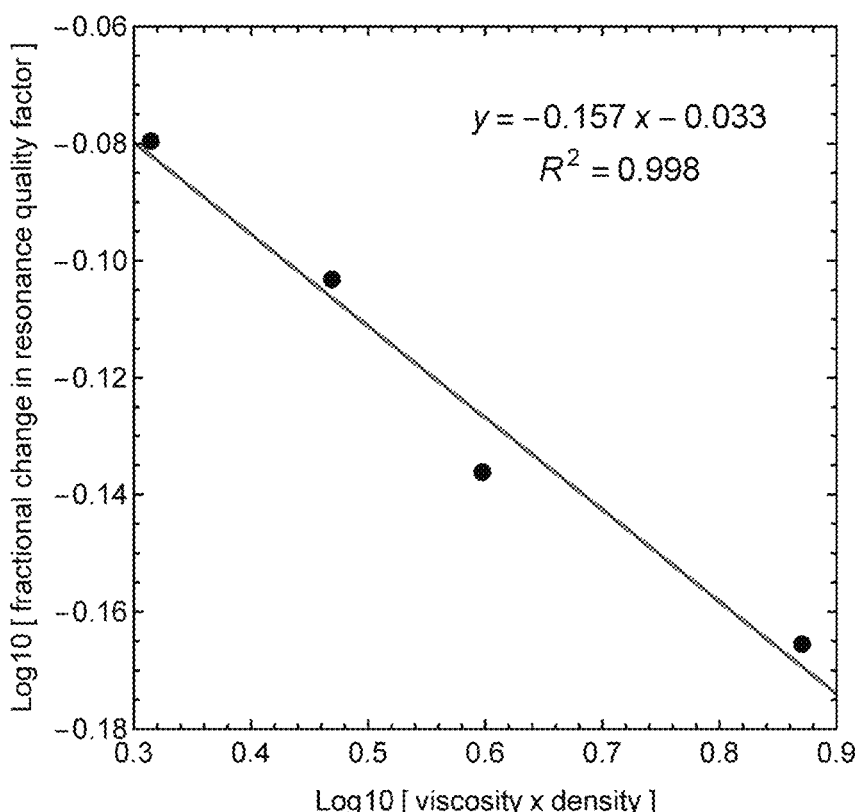

Results:

Amplitude frequency scans of the in-plane and out-of-plane oscillations of the suspended beam in the single-use disposable test strips were measured before and after insertion of the 4 ethylene glycol solutions (as stated above), with 3 strips tested per solution. The normalized fractional change in resonance amplitude, frequency and quality factor (for in-plane and out-of-plane oscillations) after insertion of the solutions were computed. Increasing concentrations of ethylene glycol dampen the sensor, such that the amplitude and frequency decreases. As the solutions become denser and more viscous it causes the physical element to oscillate more slowly and less vigorously when in contact with the fluid for both in-plane and out-of-plane oscillation modes. An example of an amplitude frequency scan for in-plane oscillation of the physical element in air and in contact with 40.38% v/v ethylene glycol (EG) solution is shown in FIG. 6. In this specific example, both the peak amplitude and frequency of the in-plane resonance are reduced when the solution is introduced into the strip.

An example of the oscillation characteristics of the in-plane mode of the physical element when exposed to varying concentrations of ethylene glycol solutions is shown in FIGS. 7(a), 7(b) and 7(c). In this specific example, the logarithm of the normalized fractional change in resonance amplitude, frequency and quality factor exhibited linear trends with the logarithm of the product of density and viscosity of the ethylene glycol solutions, as seen in FIGS. 7(a), 7(b) and 7(c), respectively. The result in this example is as predicted by theory of oscillation damping of mechanical structures wherein the damping is proportional to the inverse square root of the product of density and viscosity of the fluid.

By monitoring the in-plane and out-of-plane oscillations of the physical element, the viscosity and density of an arbitrary fluid can be deduced. The density of a fluid can be estimated from the out-of-plane mode characteristics and the viscosity-density product can be estimated from the in-plane mode, thus allowing for the independent and absolute measurement of density and viscosity of the fluid under test.

Example 2: Performance of Prothrombin Time (PT) or International Normalized Ratio (INR) Coagulation Test Using a Physical Element Sensor Device Assembled into a Disposable Test Strip Materials and Methods In this example, the general methods and procedures used were similar to that outlined in "Example 1", except for the incorporation of a blood coagulation-inducing reagent and blood sample acquisition & processing as detailed below.

Prothrombin Time Reagent Incorporation:

The disposable test strips used in this example were incorporated with a reagent comprising of rabbit brain thromboplastin (Pacific Hemostasis Prothrombin Time reagent, Thromboplastin-DS, Product #29-227-3), calcium chloride (25 mM) and Tween (2% v/v aqueous solution). Prior to the final assembly of the strip, the reagent was incorporated by dispensing the solution on to the exposed hydrophilic surface in the bottom stack, followed by air-drying in a drying box with humidity control at standard room temperature and pressure. The ratio of the volume of the reagent to blood tested in the chamber was maintained at close to 2:1 to ensure successful initiation of the blood coagulation reaction. The assembled strip incorporated with the reagent was then placed into a metallic foil pouch alongside a desiccant (e.g., silica gel) and heat-sealed, followed by storage for multiple days prior to use, in order to ensure the reagent was dried to an optimal state with minimal time-delay in initiating the coagulation reaction when in contact with the blood sample.

Blood Sample Acquisition & Processing:

In this example, finger-stick, capillary whole blood samples from patients undergoing warfarin therapy at an anticoagulation clinic and from normal subjects were used. Following procurement of informed consent under an Institutional Review Board (IRB) approved protocol, a standard lancet was used to extract blood samples by finger-stick and a pipette or dropper was used to pick up the sample for insertion into the disposable test strip. Per the standard medical procedures in the anticoagulation clinic, the lancet was used for a second time to extract blood samples for testing in the commercially available Roche CoaguChek® XS system.

Figure 8:
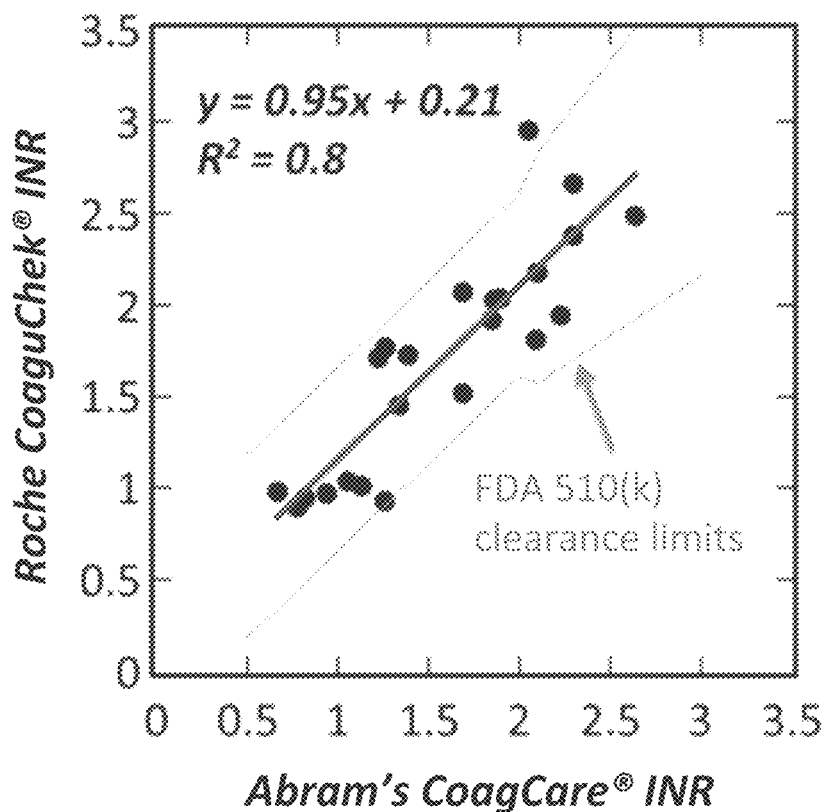
FIG. 8 shows an example of the correlation between the INR results from the Roche CoaguChek® XS system and the disposable test strip under this invention (Abram's CoagCare).

Results:

In this example, the oscillation characteristics (e.g., amplitude) of the in-plane mode of a physical element in single-use disposable test strips were monitored and recorded before and after introduction of the blood sample, in order to measure the change in viscosity and viscoelasticity of the blood sample as a function of time as it undergoes coagulation. The blood sample upon entering the chamber reacted with the dried reagent and started to coagulate through the extrinsic coagulation pathway. An algorithm was used to track the measured oscillation characteristics, viscosity and/or viscoelasticity as a function of time and identify a time to clot formation (measured starting from blood sample insertion time, t=0), in other words known as the prothrombin time (PT). The PT/INR results from the commercially available Roche CoaguChek® XS system was also recorded for comparison. An example of the correlation between the INR results from the Roche CoaguChek® XS system and the disposable test strip under this invention (Abram's CoagCare) is shown in FIG. 8. In this specific example, two rounds of testing were performed viz. calibration round (19 patients, 7 normals) and correlation round (16 patients, 7 normals). The calibration round was used to determine a calibration curve to establish a relationship between the measured PT time using the disposable test strip and the INR result from the CoaguChek® XS system. The correlation round was used to apply this calibration curve to the measured PT times and calculate a measured INR result. In this specific example, a good linear correlation with a regression coefficient $R^2$ of 0.8 was demonstrated for 0.5 to 3 INR range, with all the data points lying within the Food and Drug Administration (FDA) 510(k) clearance limits as imposed on commercially available PT/INR systems.

Example 3: Performance of Hematocrit (Hct) Measurement Using a Physical Element Sensor Device Assembled into a Disposable Test Strip Materials and Methods In this example, the general methods and procedures used were similar to that outlined in "Example 1", except for the blood sample acquisition & processing as detailed below.

Blood Sample Acquisition & Processing:

In this example, venous whole blood samples from normal subjects were used. Following procurement of informed consent under an Institutional Review Board (IRB) approved protocol, phlebotomy was performed to extract blood samples by venipuncture and the samples were directly dispensed into blood collection tubes containing ethylenediamine tetraacetic acid (EDTA) anticoagulant. The EDTA-anticoagulated whole blood samples were centrifuged to extract plasma and re-suspended with red blood cells to formulate whole blood samples with hematocrit ranging from 0 to 80% in steps of 10%. A standard microliter pipette was used to dispense the blood sample into the disposable test strip.

Figure 9:
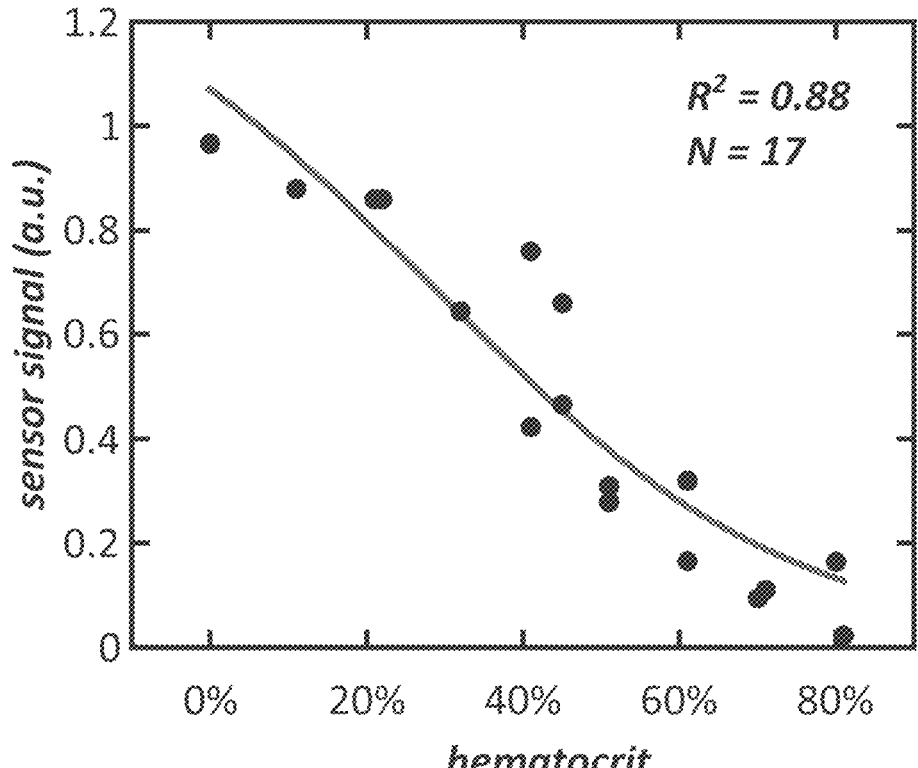
FIG. 9 shows an example of the damping in out-of-plane oscillations of a physical element in a disposable test strip, where in the sensor signal exhibits a steady and predictable decrease when exposed to blood samples with increasing hematocrit from 0 to 80%.

Results:

In this example, the oscillation characteristics (e.g., amplitude) of the out-of-plane mode of a physical element in single-use disposable test strips were monitored and recorded before and after introduction of the blood sample, in order to measure the density of the blood sample. The blood sample upon entering the chamber interacts with the physical element and damps its oscillation primarily due to its density. An example of the signal damping experienced by a physical element in a disposable test strip is shown in FIG. 9, wherein the sensor signal exhibits a steady and predictable decrease (following a vibration damping fit, regression coefficient $R^2=0.88$) when exposed to blood samples with increasing hematocrit from 0 to 80%. Since the density is linearly related to the hematocrit in a blood sample by the simple relationship $\rho=1.026+0.067$ Hct gm/cc, hematocrit can be accurately ascertained from the blood density, which is computed using the damping of the oscillation characteristics.

Example 4: Performance of Activated Partial Thromboplastin Time (aPTT) Coagulation Test Using a Physical Element Sensor Device Assembled into a Disposable Test Strip

Materials and Methods

In this example, the general methods and procedures used were similar to that outlined in "Example 1", except for the incorporation of a blood coagulation-inducing reagent and blood sample acquisition & processing as detailed below.

Activated Partial Thromboplastin Time Reagent Incorporation:

The disposable test strips used in this example were incorporated with a reagent comprising of Actin-FS activated partial thromboplastin time reagent (Siemens Diagnostics, Catalog #B4218-20), calcium chloride (25 mM) and Tween (2% v/v aqueous solution). Prior to the final assembly of the strip, the reagent was incorporated by dispensing the solution on to the exposed hydrophilic surface in the bottom stack, followed by air-drying in a drying box with humidity control at standard room temperature and pressure. The ratio of the volume of the reagent to blood tested in the chamber was maintained at close to 2:1 to ensure successful initiation of the blood coagulation reaction. The assembled strip incorporated with the reagent was then placed into a metallic foil pouch alongside a desiccant (e.g., silica gel) and heat-sealed, followed by storage for multiple days prior to use, in order to ensure the reagent was dried to an optimal state with minimal time-delay in initiating the coagulation reaction when in contact with the blood sample.

Blood Sample Acquisition & Processing:

In this example, venous whole blood and finger-stick, capillary whole blood samples from a normal subject were used. Following procurement of informed consent under an Institutional Review Board (IRB) approved protocol, phlebotomy was performed to extract the blood sample by venipuncture and the sample was directly dispensed into blood collection tubes containing sodium citrate anticoagulant. The citrated whole blood sample was spiked with unfractionated heparin (ScienCell, Catalog #0863) in vitro to formulate whole blood samples with varying heparin concentrations ranging from 0.0 to 1.0 IU/ml in steps of 0.2 IU/ml. In addition, a standard lancet was used to extract a capillary whole blood sample by finger-stick. A standard microliter pipette was used to dispense the blood sample into the disposable test strip.

Figure 10:
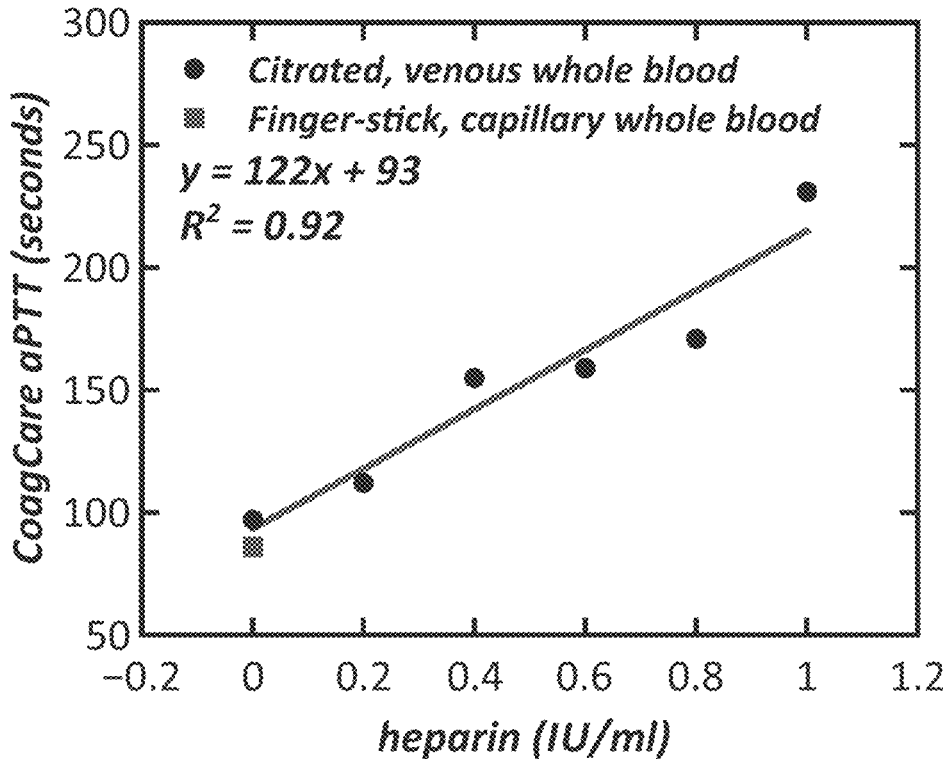
FIG. 10 shows an example of the uncalibrated aPTT blood clotting time measured using a physical element in a disposable test strip.

Results:

In this example, the oscillation characteristics (e.g., amplitude) of the in-plane mode of a physical element in single-use disposable test strips were monitored and recorded before and after introduction of the blood sample, in order to measure the change in viscosity and viscoelasticity of the blood sample as a function of time as it undergoes coagulation. The blood sample upon entering the chamber reacted with the dried reagent and started to coagulate through the intrinsic coagulation pathway. An algorithm was used to track the measured oscillation characteristics, viscosity and/or viscoelasticity as a function of time and identify a time to clot formation (measured starting from blood sample insertion time, t=0), in other words known as the partial thromboplastin time (aPTT). An example of the uncalibrated aPTT clotting time measured using a physical element in a disposable test strip is shown in FIG. 10, wherein the clotting time exhibits a linear dose response (regression coefficient $R^2=0.92$) when exposed to venous whole blood samples with increasing concentrations of heparin. In this specific example, the aPTT clotting time measured on the finger-stick, capillary whole blood sample from a normal subject (not undergoing heparin therapy) was close to that measured in the subject's venous whole blood sample with no heparin (0.0 IU/ml).

Example 5: Performance of Low Range Activated Clotting Time (ACT) Coagulation Test Using a Physical Element Sensor Device Assembled into a Disposable Test Strip

Materials and Methods

In this example, the general methods and procedures used were similar to that outlined in "Example 1", except for the incorporation of a blood coagulation-inducing reagent and blood sample acquisition & processing as detailed below.

Activated Clotting Time Reagent Incorporation:

The disposable test strips used in this example were incorporated with a reagent comprising of kaolin suspended in distilled water, calcium chloride (25 mM) and Tween (2% v/v aqueous solution). Prior to the final assembly of the strip, the reagent was incorporated by dispensing the solution on to the exposed hydrophilic surface in the bottom stack, followed by air-drying in a drying box with humidity control at standard room temperature and pressure. The ratio of the volume of the reagent to blood tested in the chamber was maintained at close to 2:1 to ensure successful initiation of the blood coagulation reaction and optimal sensitivity to the low range of heparin concentrations in the blood samples. The assembled strip incorporated with the reagent was then placed into a metallic foil pouch alongside a desiccant (e.g., silica gel) and heat-sealed, followed by storage for multiple days prior to use, in order to ensure the reagent was dried to an optimal state with minimal time-delay in initiating the coagulation reaction when in contact with the blood sample.

Blood Sample Acquisition & Processing:

In this example, venous whole blood samples from a normal subject were used. Following procurement of informed consent under an Institutional Review Board (IRB) approved protocol, phlebotomy was performed to extract the blood sample by venipuncture and the sample was directly dispensed into blood collection tubes containing sodium citrate anticoagulant. The citrated whole blood sample was spiked with unfractionated heparin (ScienCell, Catalog #0863) in vitro to formulate whole blood samples with varying heparin concentrations in the low range of 0.0 to 3.0 IU/ml in steps of 1.0 IU/ml. A standard microliter pipette was used to dispense the blood sample into the disposable test strip.

Figure 11:
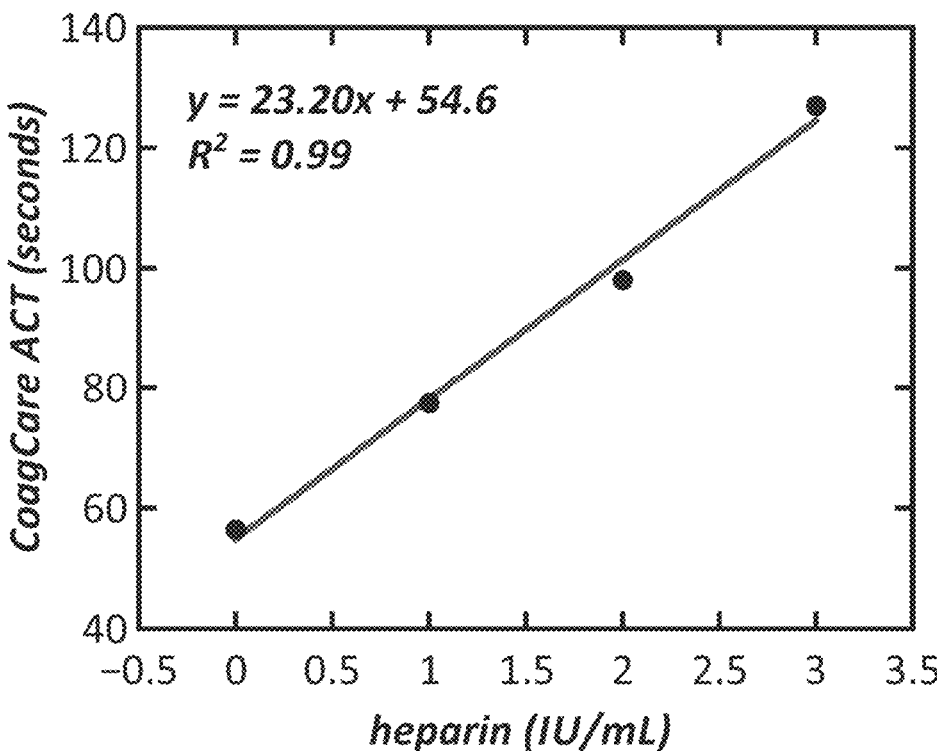
FIG. 11 shows an example of the uncalibrated low-range ACT blood clotting time measured using a physical element in a disposable test strip.

Results:

In this example, the oscillation characteristics (e.g., amplitude) of the in-plane mode of a physical element in single-use disposable test strips were monitored and recorded before and after introduction of the blood sample, in order to measure the change in viscosity and viscoelasticity of the blood sample as a function of time as it undergoes coagulation. The blood sample upon entering the chamber reacted with the dried reagent and started to coagulate through the intrinsic coagulation pathway. An algorithm was used to track the measured oscillation characteristics, viscosity and/or viscoelasticity as a function of time and identify a time to clot formation (measured starting from blood sample insertion time, t=0), in other words known as the activated clotting time (ACT). An example of the uncalibrated ACT clotting time measured using a physical element in a disposable test strip is shown in FIG. 11, wherein the clotting time exhibits a linear dose response (regression coefficient $R^2$=0.99) when exposed to venous whole blood samples with increasing concentrations of heparin. In this specific example, the ACT clotting time measured corresponds to a low-range ACT measurement given the system's sensitivity from 0.0 to 3.0 IU/ml, which corresponds to the low range of heparin therapy used during cardiac and hepatic surgeries.

Example 6: Performance of High Range Activated Clotting Time (ACT) Coagulation Test Using a Physical Element Sensor Device Assembled into a Disposable Test Strip Materials and Methods In this example, the general methods and procedures used were similar to that outlined in "Example 1", except for the incorporation of a blood coagulation-inducing reagent and blood sample acquisition & processing as detailed below.

Activated Clotting Time Reagent Incorporation:

The disposable test strips used in this example were incorporated with a reagent comprising of kaolin suspended in distilled water, calcium chloride (25 mM) and Tween (2% v/v aqueous solution). Prior to the final assembly of the strip, the reagent was incorporated by dispensing the solution on to the exposed hydrophilic surface in the bottom stack, followed by air-drying in a drying box with humidity control at standard room temperature and pressure. The ratio of the volume of the reagent to blood tested in the chamber was maintained at close to 2:1 to ensure successful initiation of the blood coagulation reaction and optimal sensitivity to the high range of heparin concentrations in the blood samples. The assembled strip incorporated with the reagent was then placed into a metallic foil pouch alongside a desiccant (e.g., silica gel) and heat-sealed, followed by storage for multiple days prior to use, in order to ensure the reagent was dried to an optimal state with minimal time-delay in initiating the coagulation reaction when in contact with the blood sample.

Blood Sample Acquisition & Processing:

In this example, venous whole blood samples from a normal subject were used. Following procurement of informed consent under an Institutional Review Board (IRB) approved protocol, phlebotomy was performed to extract the blood sample by venipuncture and the sample was directly dispensed into blood collection tubes containing sodium citrate anticoagulant. The citrated whole blood sample was spiked with unfractionated heparin (ScienCell, Catalog #0863) in vitro to formulate whole blood samples with varying heparin concentrations in the high range of 1.0 to 5.0 IU/ml in steps of 1.0 IU/ml. A standard microliter pipette was used to dispense the blood sample into the disposable test strip.

Figure 12:
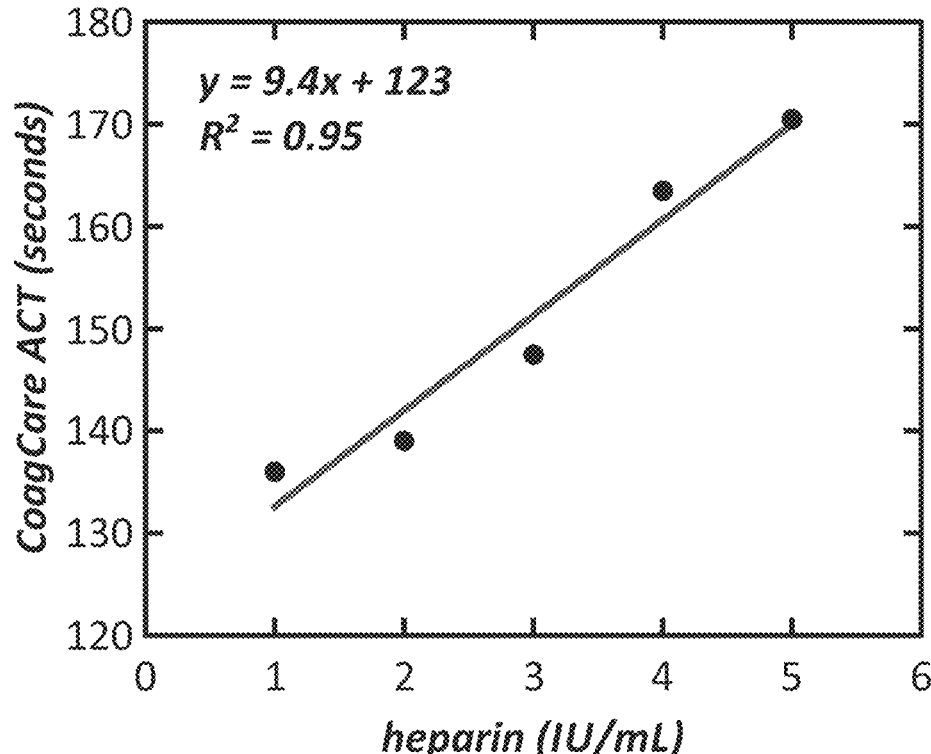
FIG. 12 shows an example of the uncalibrated high-range ACT blood clotting time measured using a physical element in a disposable test strip.

Results:

In this example, the oscillation characteristics (e.g., amplitude) of the in-plane mode of a physical element in single-use disposable test strips were monitored and recorded before and after introduction of the blood sample, in order to measure the change in viscosity and viscoelasticity of the blood sample as a function of time as it undergoes coagulation. The blood sample upon entering the chamber reacted with the dried reagent and started to coagulate through the intrinsic coagulation pathway. An algorithm was used to track the measured oscillation characteristics, viscosity and/or viscoelasticity as a function of time and identify a time to clot formation (measured starting from blood sample insertion time, t=0), in other words known as the activated clotting time (ACT). An example of the uncalibrated ACT clotting time measured using a physical element in a disposable test strip is shown in FIG. 12, wherein the clotting time exhibits a linear dose response (regression coefficient $R^2$=0.95) when exposed to venous whole blood samples with increasing concentrations of heparin. In this specific example, the ACT clotting time measured corresponds to a high-range ACT measurement given the system's sensitivity from 1.0 to 5.0 IU/ml, which corresponds to the high range of heparin therapy used during cardiac and hepatic surgeries.

Example 7: Performance of Thromboelastogram (TEG) Coagulation Test Using a Physical Element Sensor DAevice Ssembled into a Disposable Test Strip Materials and Methods In this example, the general methods and procedures used were similar to that outlined in "Example 1", except for the incorporation of a blood coagulation-inducing reagent and blood sample acquisition & processing as detailed below.

Thromboelastogram Reagent Incorporation:

The disposable test strips used in this example were incorporated with a reagent comprising of rabbit brain thromboplastin (Pacific Hemostasis Prothrombin Time reagent, Thromboplastin-DS, Product #29-227-3), calcium chloride (25 mM) and Tween (2% v/v aqueous solution). Prior to the final assembly of the strip, the reagent was incorporated by dispensing the solution on to the exposed hydrophilic surface in the bottom stack, followed by air-drying in a drying box with humidity control at standard room temperature and pressure. The ratio of the volume of the reagent to blood tested in the chamber was maintained at close to 2:1 to ensure successful initiation of the blood coagulation reaction. The assembled strip incorporated with the reagent was then placed into a metallic foil pouch alongside a desiccant (e.g., silica gel) and heat-sealed, followed by storage for multiple days prior to use, in order to ensure the reagent was dried to an optimal state with minimal time-delay in initiating the coagulation reaction when in contact with the blood sample.

Blood Sample Acquisition & Processing:

In this example, venous whole blood and finger-stick, capillary whole blood samples from a normal subject were used. In addition, finger-stick, capillary whole blood samples from patients undergoing warfarin therapy at an anticoagulation clinic were used. Following procurement of informed consent under an Institutional Review Board (IRB) approved protocol, phlebotomy was performed to extract the blood sample by venipuncture and the sample was directly dispensed into blood collection tubes containing sodium citrate anticoagulant. The citrated whole blood samples were contrived in vitro to incorporate varying amounts of unfractionated heparin (0 to 3 IU/ml), cleavable fibrinogen (42 to 231 mg/dL), Eptifibatide (GPIIb/IIIa platelet inhibitor, 0 to 12 µg/mL), and tissue plasminogen activator (tPA, 0 to 1.8 nM). Further in some tests, following procurement of informed consent under an Institutional Review Board (IRB) approved protocol, a standard lancet was used to extract blood samples by finger-stick and a standard microliter pipette or dropper was used to pick up the sample for insertion into the disposable test strip. Lastly, in some tests, blood samples were also tested using 2 Haemonetics' TEG-5000 instruments (2 tests per instrument) and their corresponding TEG curve & parameters were recorded, in order to perform side-by-side comparison with the results generated using the disposable test strips.

Figure 13:
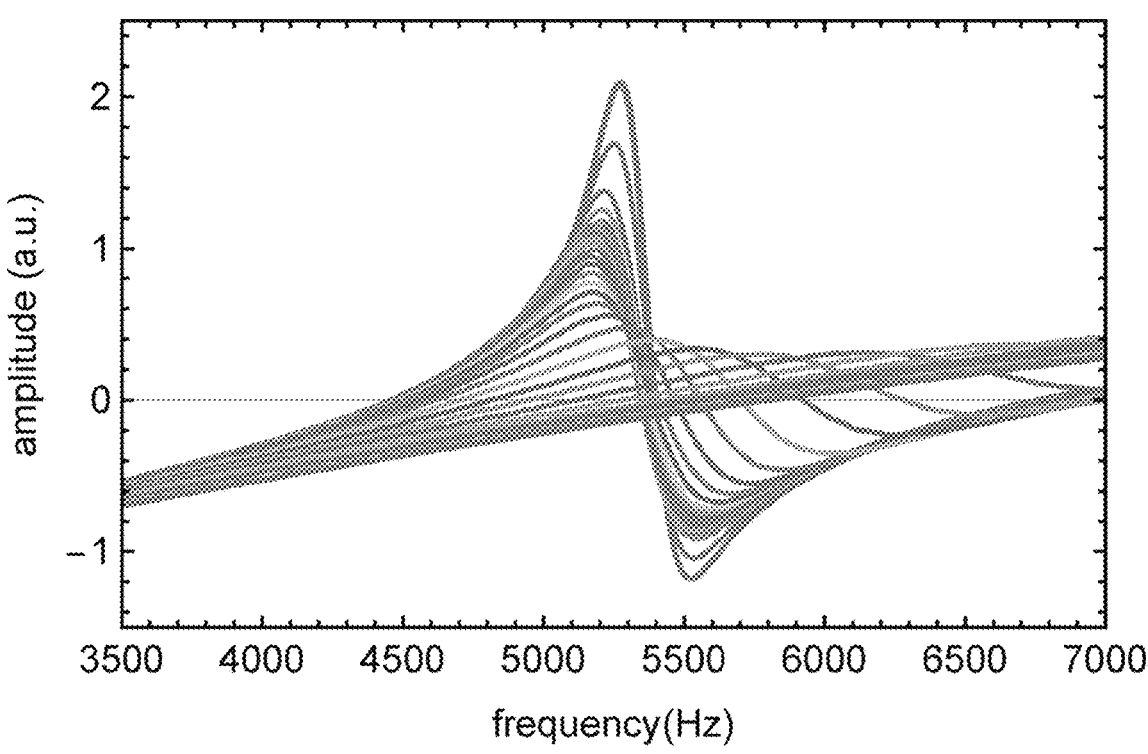
FIGS. 13(a) and 13(b) show examples of the amplitude and phase frequency scans, respectively, of an oscillating physical element in a disposable test strip with a blood sample in the chamber undergoing coagulation.
Figure 13:
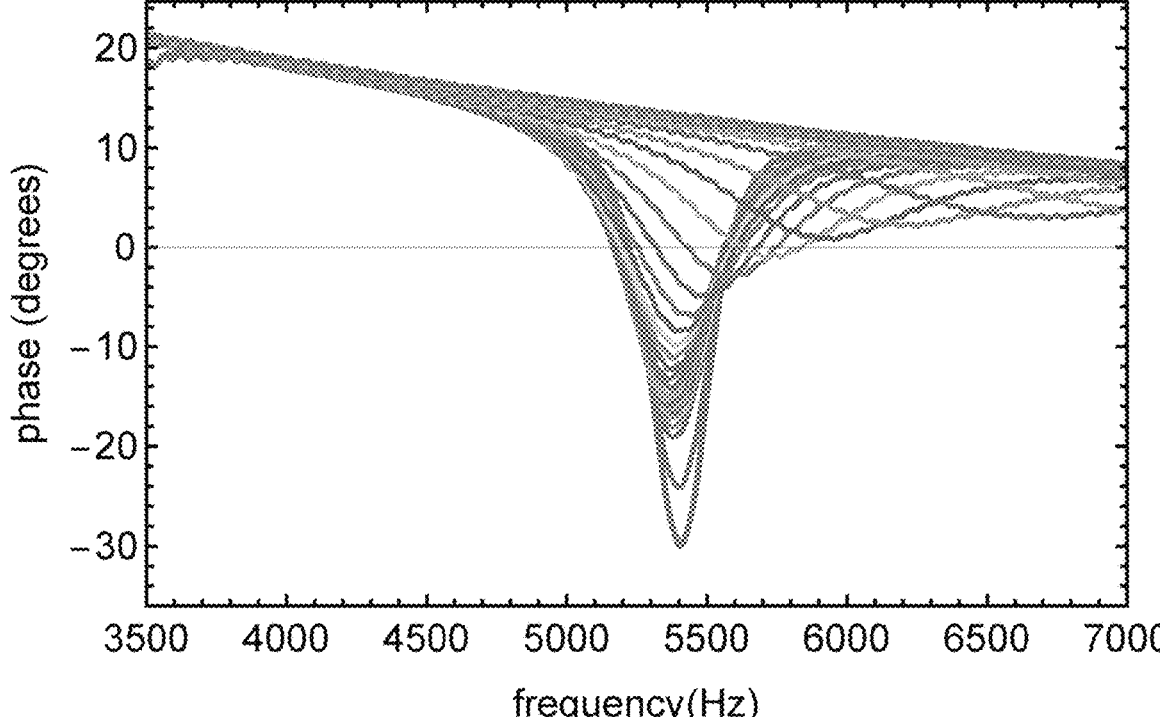

Results:

In this example, the oscillation characteristics (amplitude and phase) of the in-plane vibration mode of a physical element in single-use disposable test strips were measured as a function of frequency in the vicinity of the resonance frequency, and these amplitude & phase frequency scans were monitored periodically to determine different aspects of the blood coagulation cascade. The blood sample upon entering the chamber reacted with the dried reagent and started to coagulate through the extrinsic coagulation pathway. An example of the amplitude and phase frequency scans of an oscillating physical element in a disposable test strip with a blood sample in the chamber undergoing coagulation is shown in FIGS. 13(*a*) and 13(*b*), respectively, wherein the amplitude and phase at the resonance frequency peak are seen to decrease in magnitude as the blood coagulation cascade progresses. These amplitude and phase frequency scans monitored periodically over time were used to perform a Thromboelastogram (TEG) test, wherein a characteristic wineglass shaped viscoelastic curve and parameters were extracted. The TEG-like viscoelastic parameters extracted were clot formation time (R), activated clotting time (ACT), maximum thrombin generation (ThrombinPeak), clot stiffness (G), platelet contraction rate (Plt-Cont), and fibrinolysis rate (Lys-Rate). A mathematical model of the viscoelastic oscillation damping of the physical element, which incorporated the different kinetic processes in the coagulation cascade, was used to fit to data from the amplitude and phase frequency scans measured as a function of time. This model enabled the extraction of different hemostatic parameters, such as Time for threshold Thrombin generation (R), rate of catalysis by Prothrombinase or Factor-Xa ($k_2$), rate of catalysis by Thrombin or Factor-IIa ($k_1$), concentration of cleavable Fibrinogen or Factor-I ($C_{fibrinogen}$ or [Fibrinogen]), clot stiffness (G), platelet contraction rate (Plt-Cont), and fibrinolysis rate (Lys-Rate). These measured hemostatic parameters were used to extract the above-mentioned TEG-like viscoelastic parameters and monitor the concentration and activity of different coagulation factors (e.g., fibrinogen, thrombin), blood clot-specific characteristics (e.g., clot stiffness G, fibrinolysis rate Lys-Rate), and activity/effect of different blood constituents participating in coagulation (e.g., platelet contraction rate Plt-Cont,), as a function of time during the blood coagulation cascade.

Figure 14:
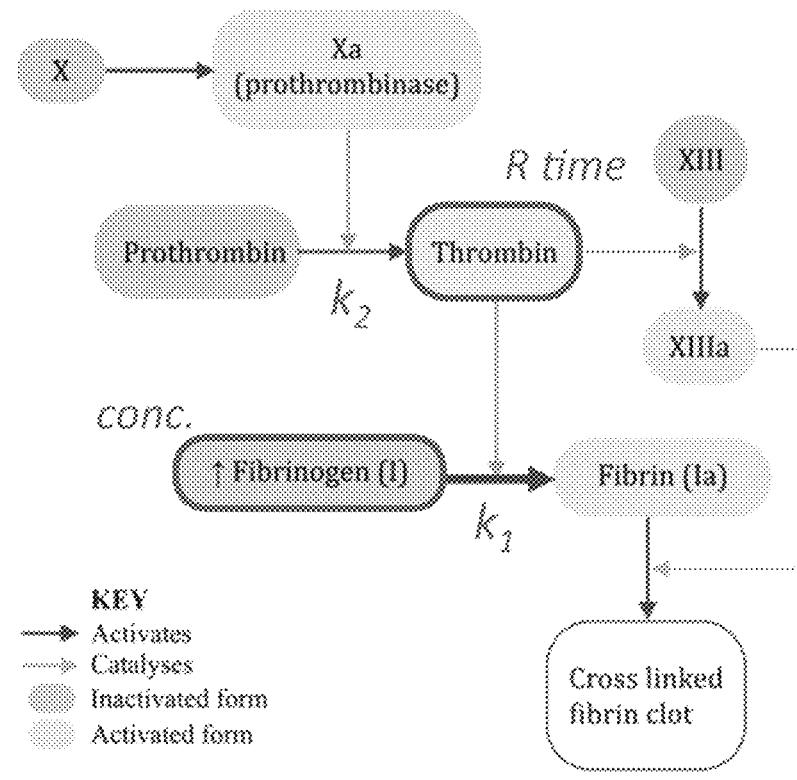
FIG. 14(*a*) shows an example illustration of the extracted hemostatic parameters related to the blood coagulation cascade and FIG. 14(*b*) shows an example of the corresponding viscoelastic vibration damping fit to the oscillation amplitude data from a physical element in a disposable test strip with a blood sample in the chamber undergoing coagulation.
Figure 14:
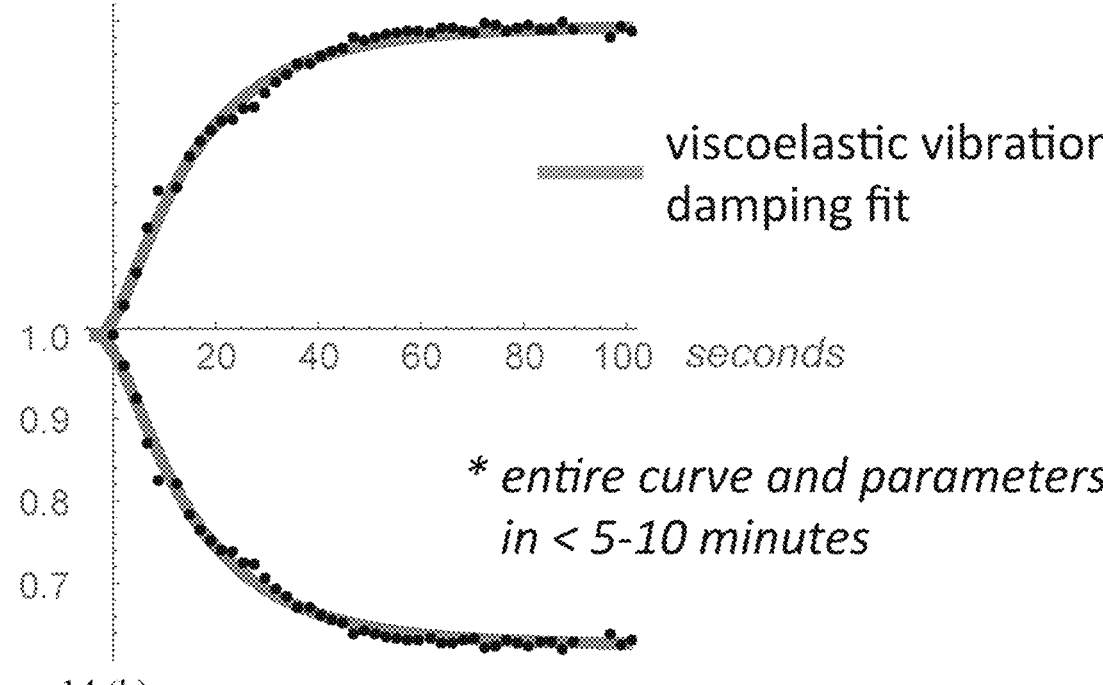

An example illustrating the extracted hemostatic parameters related to the blood coagulation cascade and a corresponding viscoelastic vibration damping fit to the oscillation amplitude data from a physical element in a disposable test strip with a blood sample in the chamber undergoing coagulation is shown in FIGS. 14(*a*) and 14(*b*), respectively. In this specific example, the oscillation amplitude data & its fit plotted as a function of time and mirrored about the time-axis, similar to a typical TEG-like wineglass shaped viscoelastic curve, was generated alongside extraction of the abovementioned TEG-like viscoelastic parameters in under 5-10 minutes. This fast turnaround time was made possible because of the high sensitivity of the physical element device and the low blood sample volume required for testing, given that smaller clots are faster to form.

Figure 15:
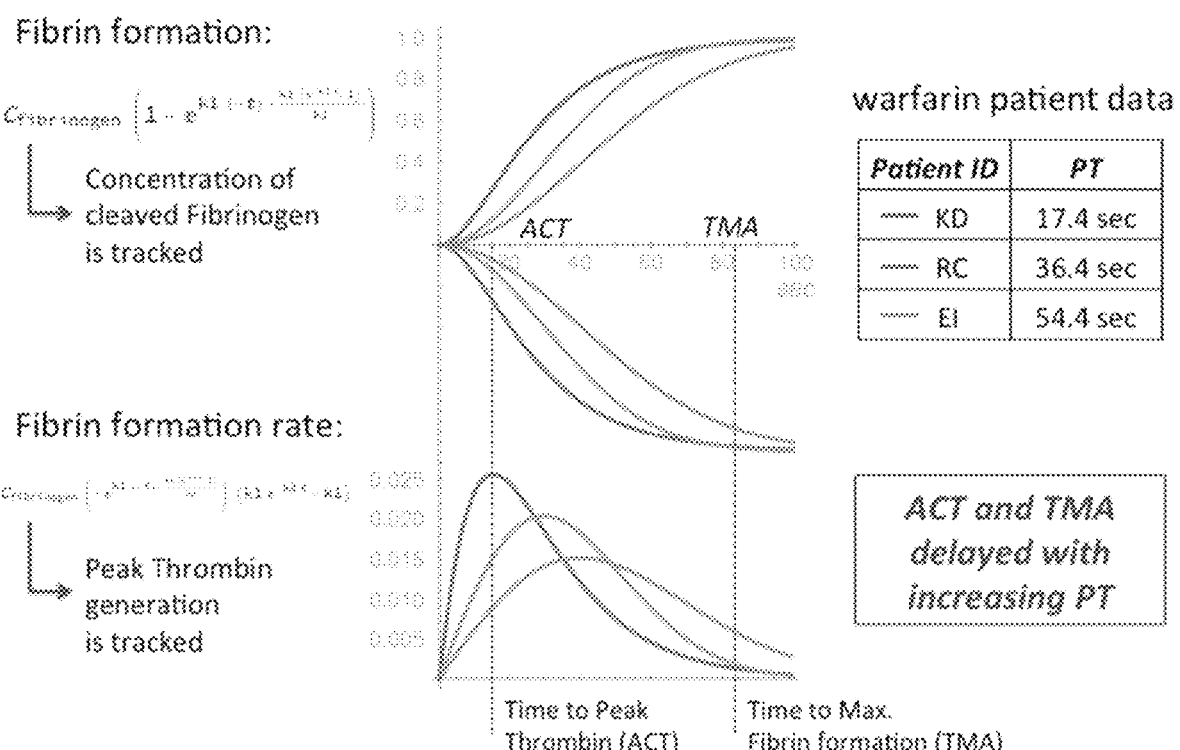
FIG. 15 shows an example illustration of the hemostatic parameters extracted from the fit being used to generate cleaved fibrinogen or fibrin and thrombin concentration profiles as a function of time during the blood coagulation cascade, as measured using a physical element in a disposable test strip.

An example illustrating the hemostatic parameters extracted from the fit being used to generate cleaved fibrinogen or fibrin and thrombin concentration profiles as a function of time during the blood coagulation cascade, as measured using a physical element in a disposable test strip is shown in FIG. 15. An example of the typical mathematical formulations used to track the concentration of cleaved fibrinogen (or converted fibrin) and thrombin are shown in the left-hand side of FIG. 15. In this specific example, 3 warfarin patient samples (with increasing PT values of 17.4, 36.4 and 54.4 seconds) were used to perform blood coagulation measurement using the disposable strips, wherein various aspects of the blood coagulation cascade were inhibited due to increasing levels of warfarin. As seen on the right-hand side of FIG. 15, the cleaved fibrinogen and thrombin concentration profiles for these 3 samples were generated, which indicate the steady decrease in maximum thrombin generation with increasing warfarin activity across the samples. Note that the cleaved fibrinogen concentration profile as a function of time was mirrored about the time axis. Further, other parameters such as time to maximum thrombin generation (analogous to the ACT) and time to maximum fibrin formation (TMA) were observed to be delayed with increasing warfarin activity across the samples. Note that this cleaved fibrinogen or fibrin formation profile as a function of time mirrored about the time-axis can also be used for reporting a typical TEG-like wineglass shaped viscoelastic curve, alongside the measured TEG-like viscoelastic parameters.

Figure 16:
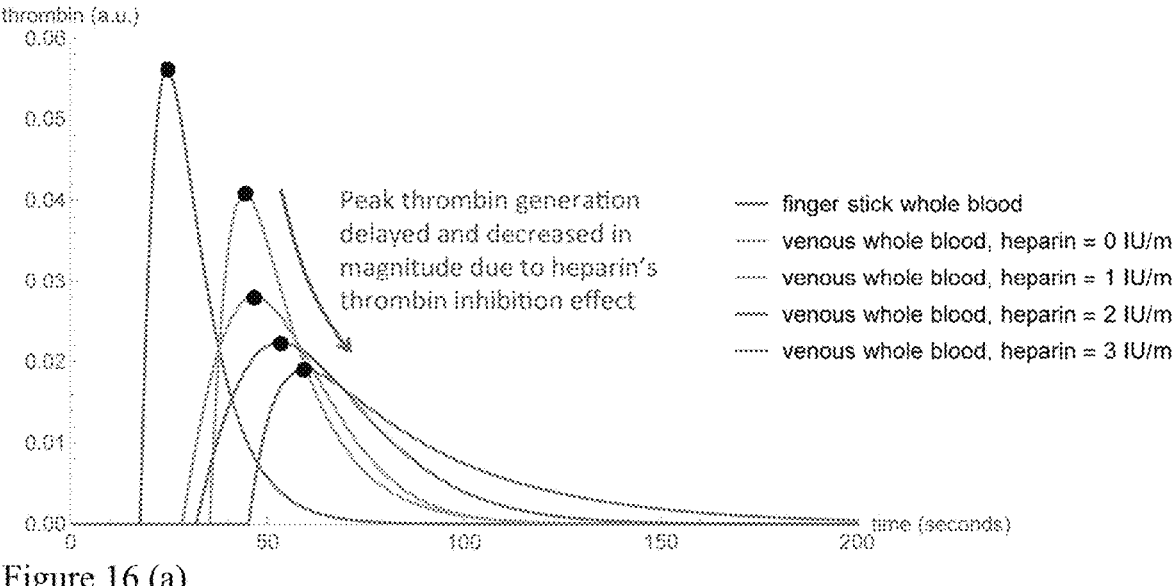
FIG. 16(*a*) and FIG. 16(*b*) shows an example illustration of the variation in thrombin generation and activated clotting time (ACT) in the presence of heparin anticoagulant (thrombin-inhibitor), as measured using a physical element in a disposable test strip.
Figure 16:
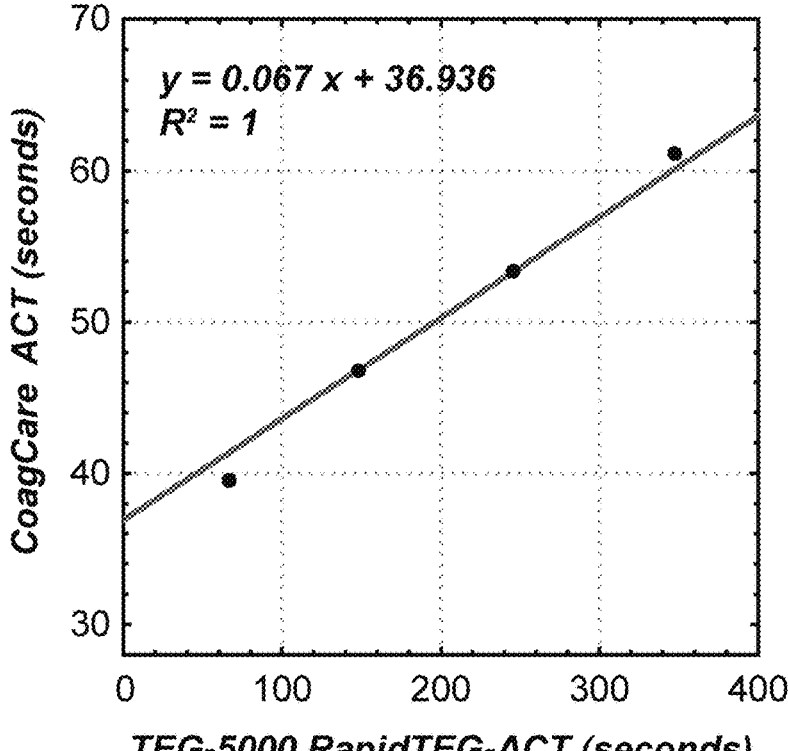

An example illustrating the variation in thrombin generation and activated clotting time (ACT) in the presence of heparin anticoagulant (thrombin-inhibitor), as measured using a physical element in a disposable test strip is shown in FIGS. 16(*a*) and 16(*b*). In this specific example, FIG. 16(*a*) shows thrombin concentration or generation profiles (in arbitrary units, since it is uncalibrated) were measured in blood samples with increasing heparin concentrations from 0 to 3 IU/ml, wherein the peak thrombin generation was observed to decrease and be delayed (i.e. increase in ACT) due to heparin's thrombin inhibition effect. Note that the thrombin concentration profiles and corresponding parameters generated in under 5-10 minutes are similar to the typical thrombin generation assay (TGA) curve & parameters measured in commercially available systems and, hence, this result can be calibrated to perform this TGA measurement. This enables a significant advantage over the commercially available TGA systems that require up to 30-60 minutes to generate the entire TGA curve and parameters. Further in this specific example, FIG. 16(*b*) illustrates a correlation plot of the increasing ACT times in the samples as measured using the disposable test strips (CoagCare ACT) and the TEG-5000 RapidTEG assay, which demonstrated a linear dose response (regression coefficient $R^2=1$).

Figure 17:
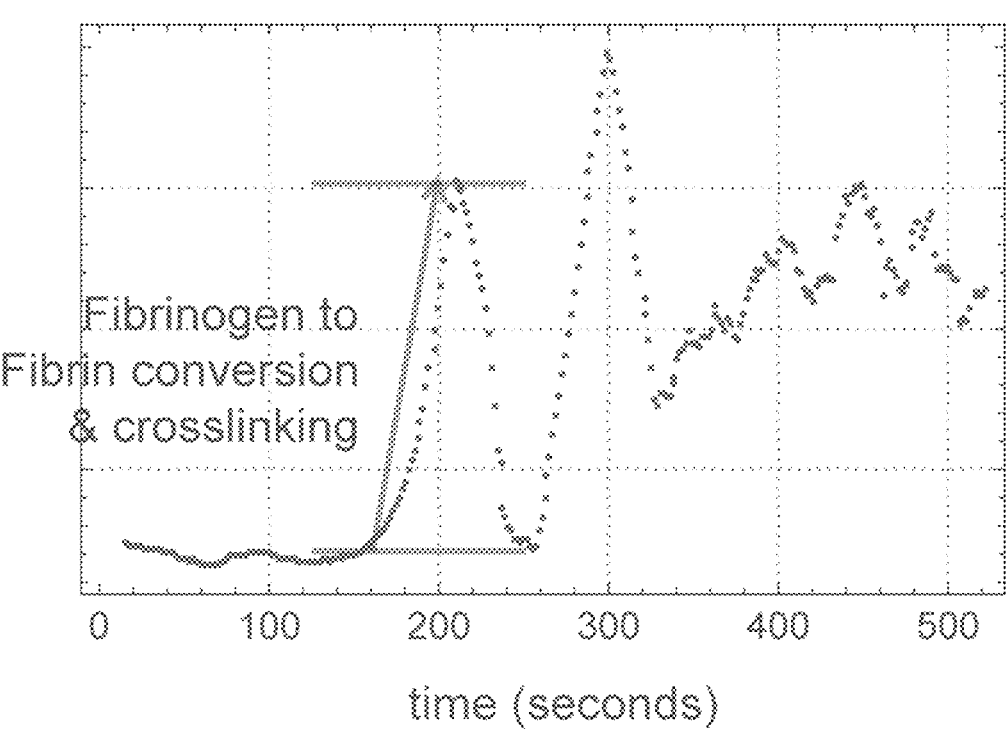
FIG. 17(*a*) and FIG. 17(*b*) shows an example illustration of the hemostatic parameters extracted from the fit being used to monitor a blood clot-specific characteristic, clot stiffness G, during the blood coagulation cascade, as measured using a physical element in a disposable test strip.
Figure 17:
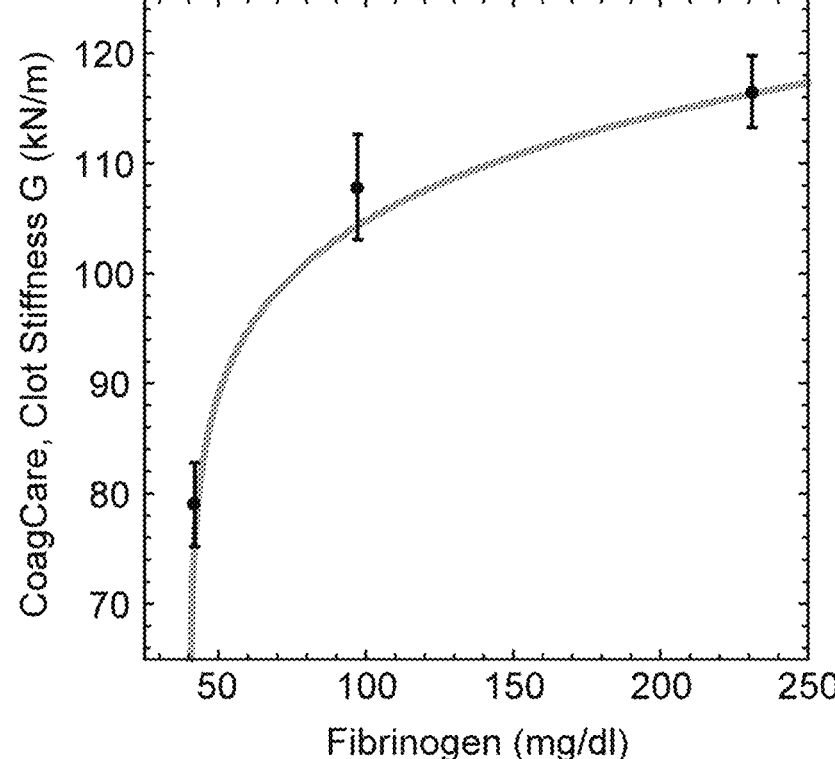

An example illustrating the hemostatic parameters extracted from the fit being used to monitor a blood clot-specific characteristic, clot stiffness G, during the blood coagulation cascade, as measured using a physical element in a disposable test strip is shown in FIGS. 17(*a*) and 17(*b*). In this specific example, FIG. 17(*a*) illustrates a typical oscillation characteristic of the in-plane vibration mode of the suspended beam measured as a function of time, wherein a steep increase observed initially is indicative of the clot stiffness G that tracks the conversion of fibrinogen (i.e. cleaving) to fibrin, followed by its crosslinking to form the fibrin network. This clot stiffness G is computed using the hemostatic parameters extracted from the fit. Further in this specific example, FIG. 17(*b*) illustrates a dose response for clot stiffness G demonstrating an increasing trend (with a good fit to the mathematical formulation), when exposed to blood samples with increasing concentrations of cleavable fibrinogen.

Figure 18:
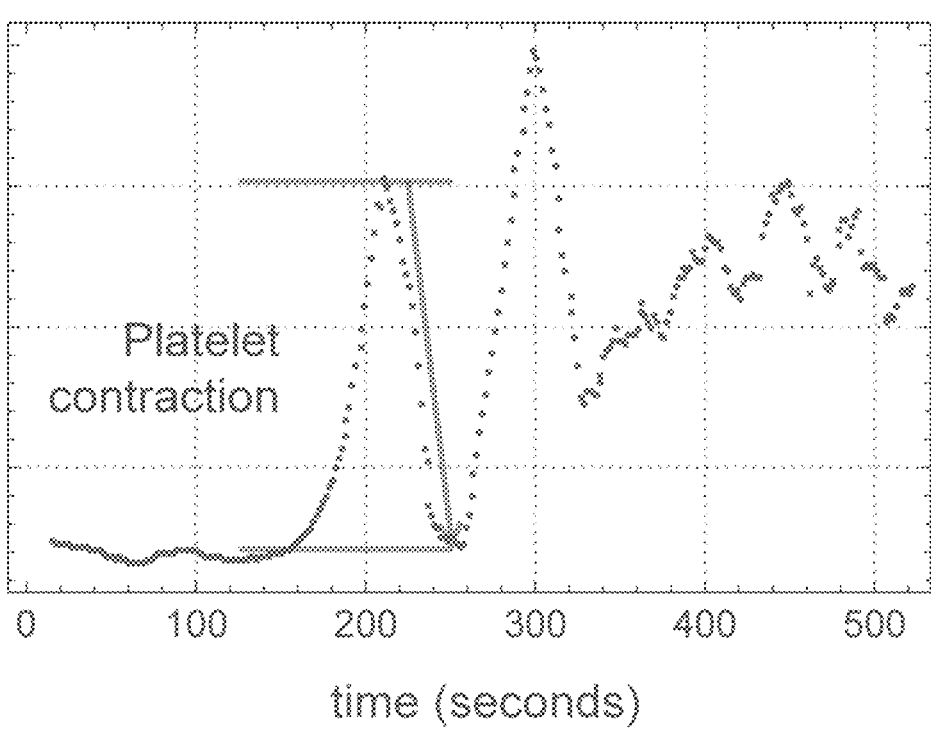
FIG. 18(*a*) and FIG. 18(*b*) shows an example illustration of the hemostatic parameters extracted from the fit being used to monitor the activity of a blood constituent, platelets, during the blood coagulation cascade, as measured using a physical element in a disposable test strip.
Figure 18:
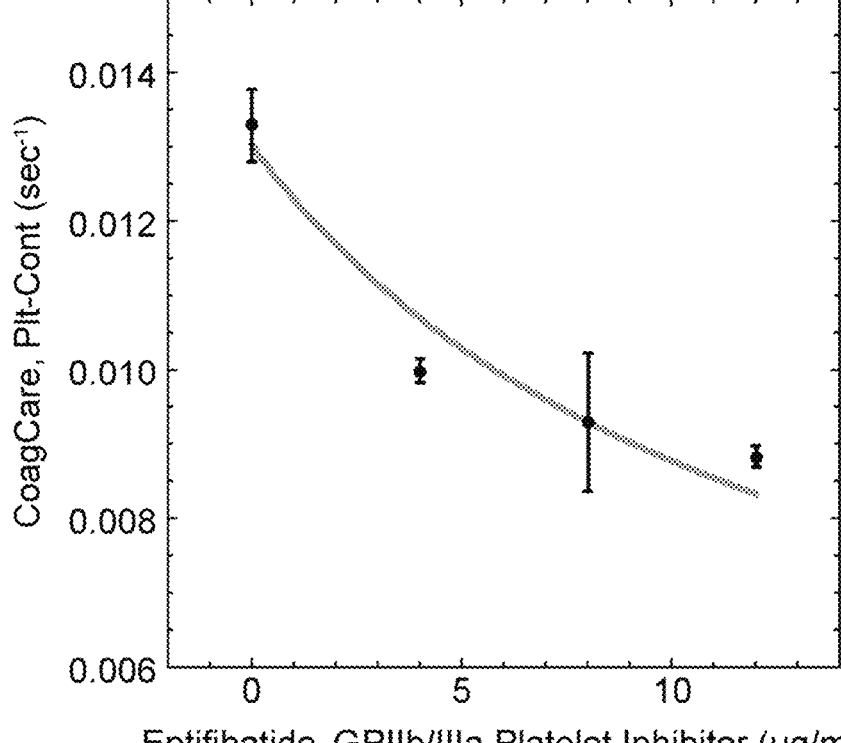

An example illustrating the hemostatic parameters extracted from the fit being used to monitor the activity of a blood constituent, platelets, during the blood coagulation cascade, as measured using a physical element in a disposable test strip is shown in FIGS. 18(*a*) and 18(*b*). In this specific example, FIG. 18(*a*) illustrates a typical oscillation characteristic of the in-plane vibration mode of the suspended beam measured as a function of time, wherein a steep drop observed (following the initial increase) is indicative of the start of contraction of platelets following their adhesion to the cross-linked fibrin network. The rate of this platelet contraction Plt-Cont is computed using the hemostatic parameters extracted from the fit. Further in this specific example, FIG. 18(*b*) illustrates a dose response for the rate of platelet contraction demonstrating a decreasing trend (with a good fit to the mathematical formulation), when exposed to blood samples with increasing concentrations of Eptifibatide GPIIb/IIIa platelet inhibitor. Note that the measured platelet contraction rate can also be used to measure the concentration of platelets and perform specific platelet function assays (PFA) in the presence of agonists (e.g., adenosine diphosphate (ADP), arachidonic acid (AA)) similar to that performed in commercially available systems (e.g., Roche's Multiplate Analyzer).

Figure 19:
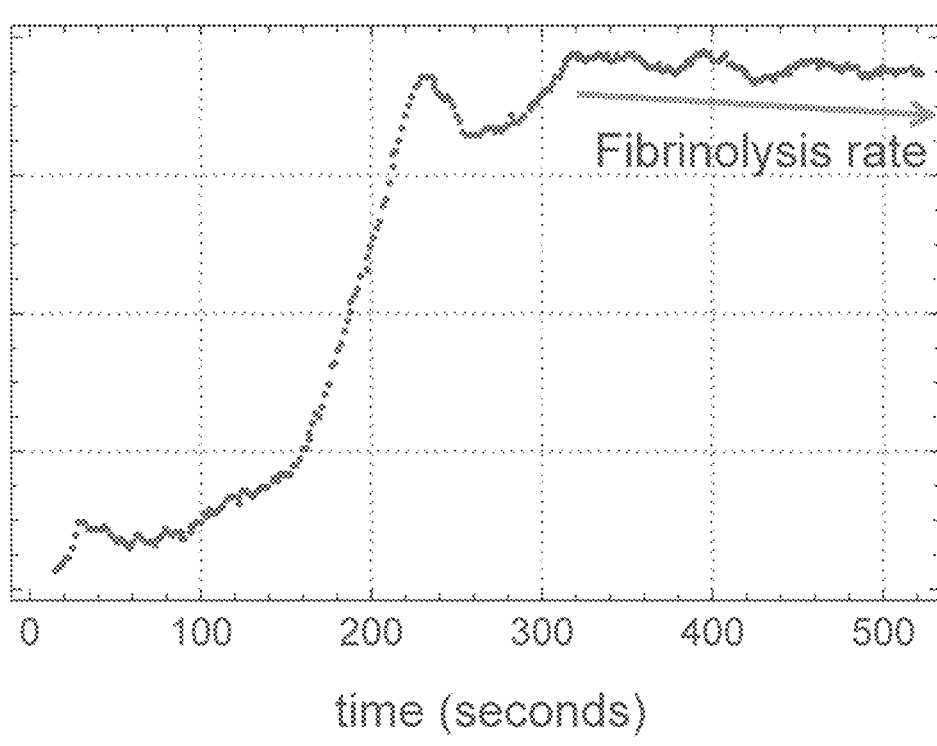
FIG. 19(*a*) and FIG. 19(*b*) shows an example illustration of the hemostatic parameters extracted from the fit being used to monitor a blood clot-specific characteristic, fibrinolysis rate Lys-Rate, during the blood coagulation cascade, as measured using a physical element in a disposable test strip.
Figure 19:
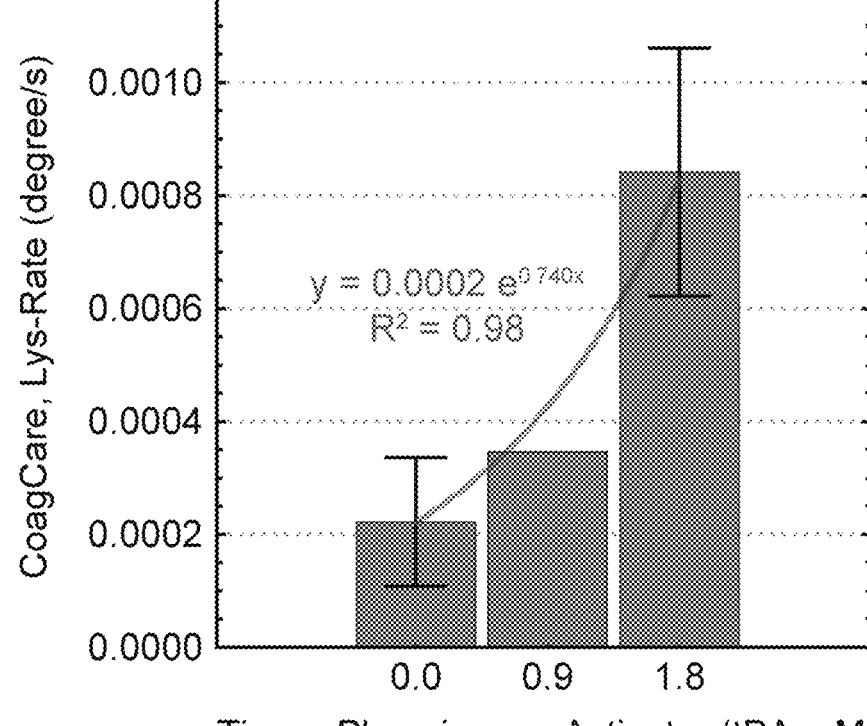

An example illustrating the hemostatic parameters extracted from the fit being used to monitor a blood clot-specific characteristic, fibrinolysis rate Lys-Rate, during the blood coagulation cascade, as measured using a physical element in a disposable test strip is shown in FIGS. 19(*a*) and 19(*b*). In this specific example, FIG. 19(*a*) illustrates a typical oscillation characteristic of the in-plane vibration mode of the suspended beam measured as a function of time, wherein a gradual decrease observed following the initial steep rise is indicative of the fibrinolysis rate Lys-Rate, which tracks the lysing or breakdown of the cross-linked fibrin network. This fibrinolysis rate Lys-Rate is computed using the hemostatic parameters extracted from the fit. Further in this specific example, FIG. 19(*b*) illustrates a dose response for fibrinolysis rate Lys-Rate demonstrating an increasing trend with a good exponential fit to the mathematical formulation, when exposed to blood samples with increasing concentrations of tissue plasminogen activator (tPA), which enhances the external fibrinolysis process of the blood coagulation cascade.

Figure 20:
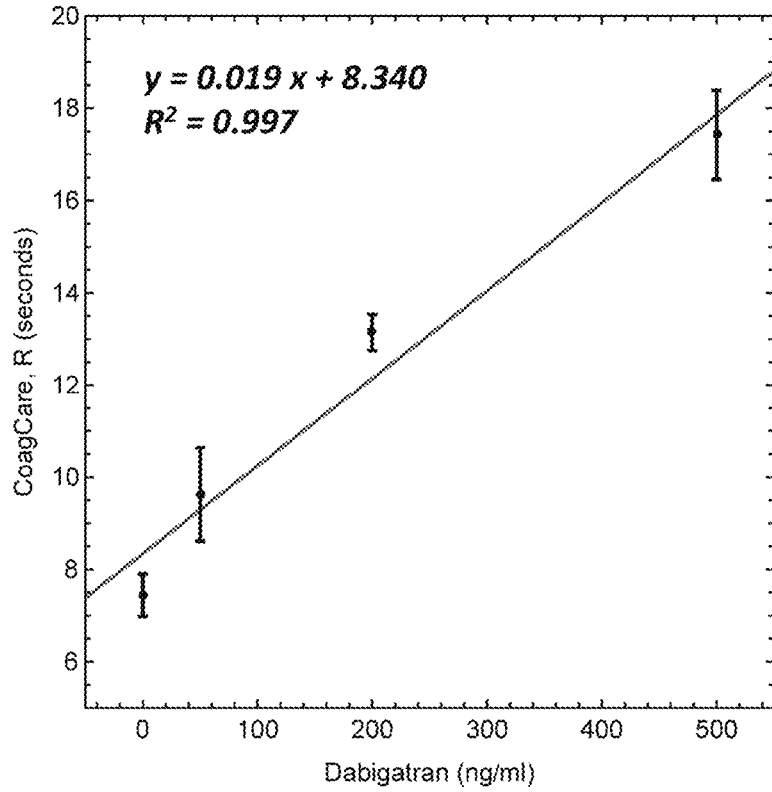
FIG. 20(*a*) and FIG. 20(*b*) shows an example illustration of the TEG-like viscoelastic parameters, extracted using the hemostatic parameters from the fit, being used to determine the concentration of a factor-IIa (Dabigatran or Pradaxa®) inhibitor-based anticoagulant, as measured using a physical element in a disposable test strip.
Figure 20:
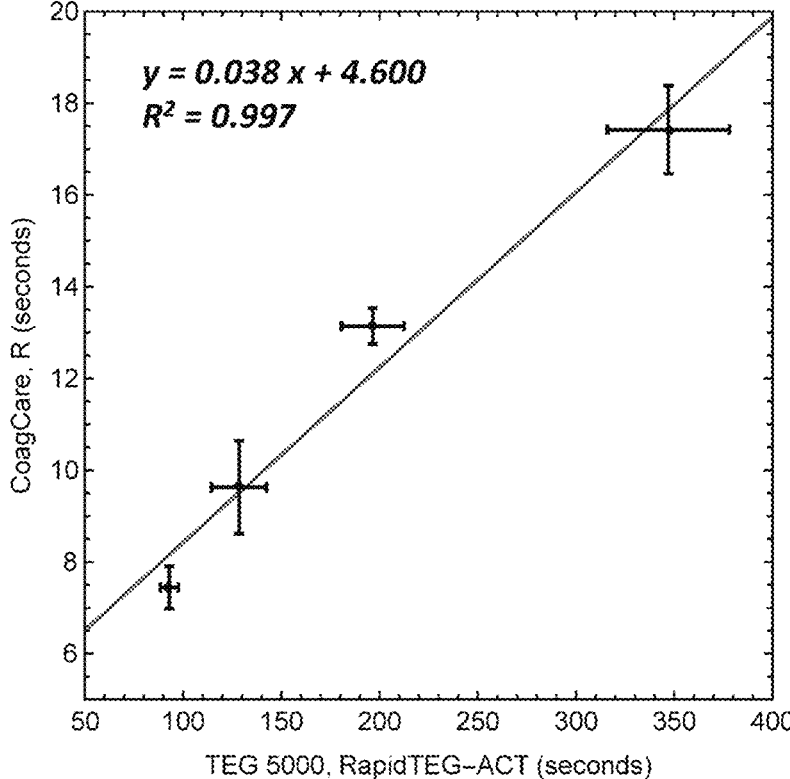
Figure 21:
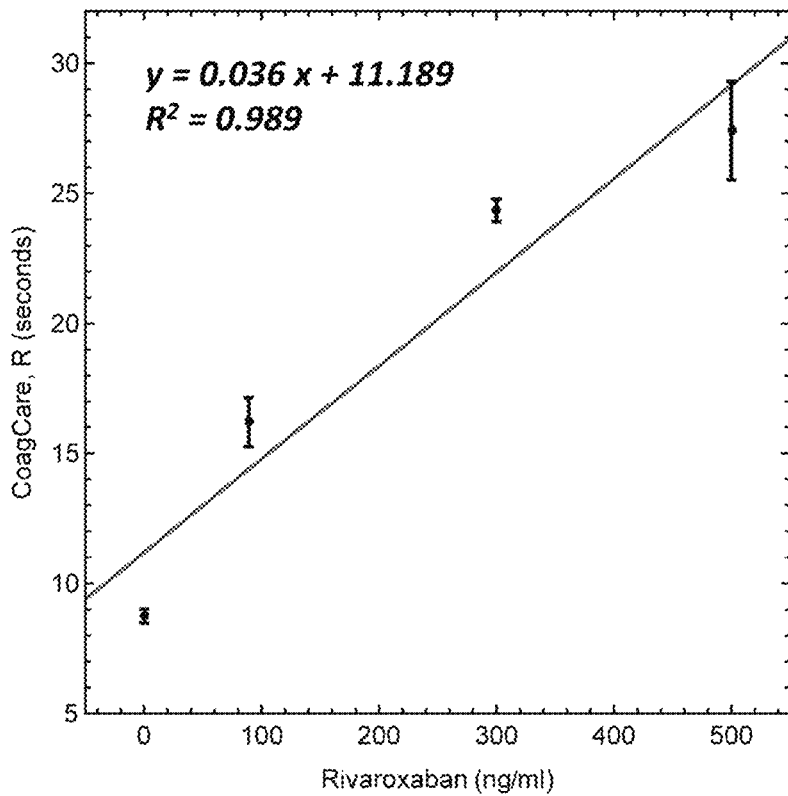
FIGS. 21(*a*) and 21(*b*) shows an example illustration of the TEG-like viscoelastic parameters, extracted using the hemostatic parameters from the fit, being used to determine the concentration of a factor-Xa (Rivaroxaban or Xarelto®) inhibitor-based anticoagulant, as measured using a physical element in a disposable test strip.
Figure 21:
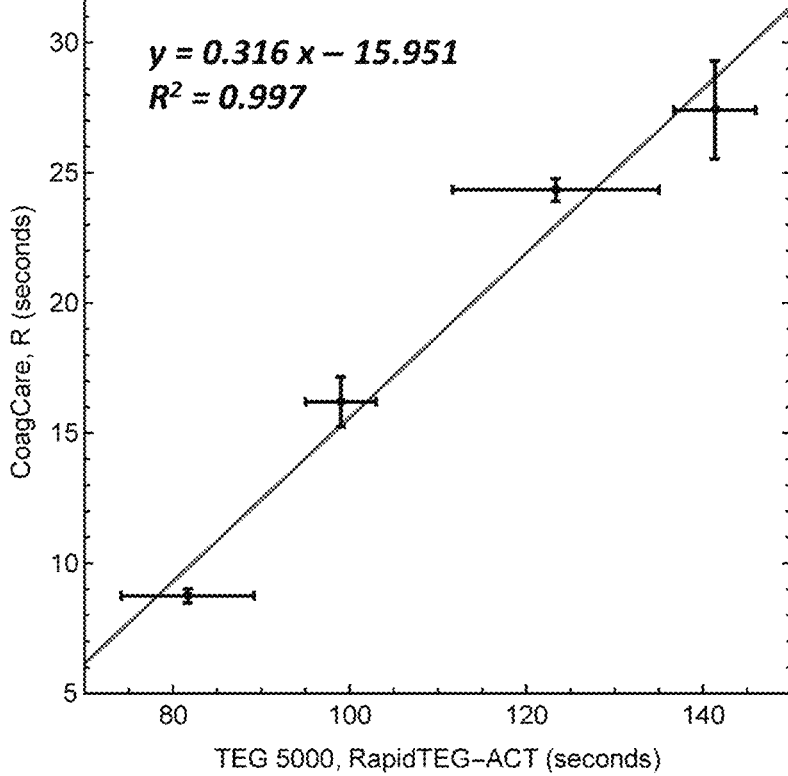
Figure 22:
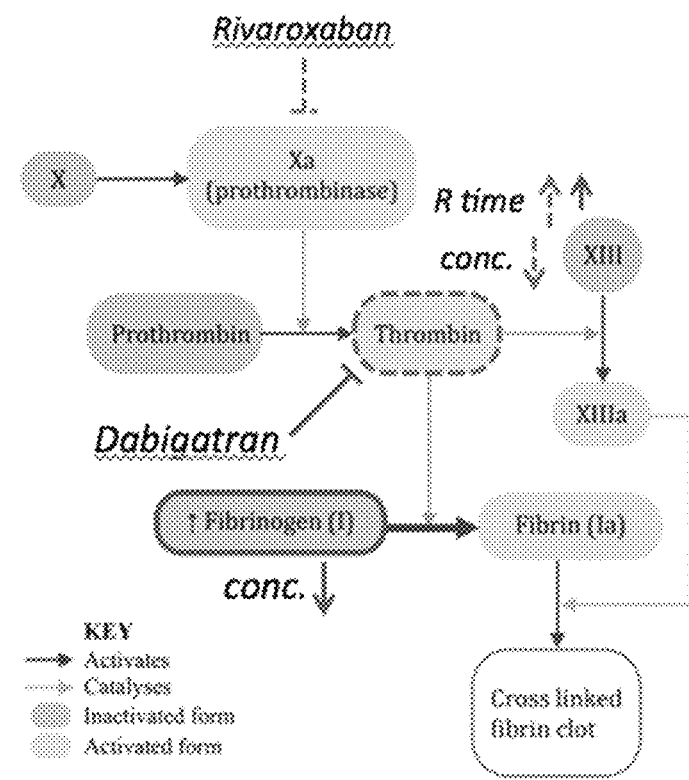
FIG. 22(*a*) portrays the blood coagulation cascade processes and specifically illustrates Dabigatran's inhibition of thrombin activity or the cleaving/conversion of fibrinogen to fibrin and Rivaroxaban's inhibition of thrombin generation through Factor-Xa, and their respective effect on the clot formation time (R).
Figure 22:
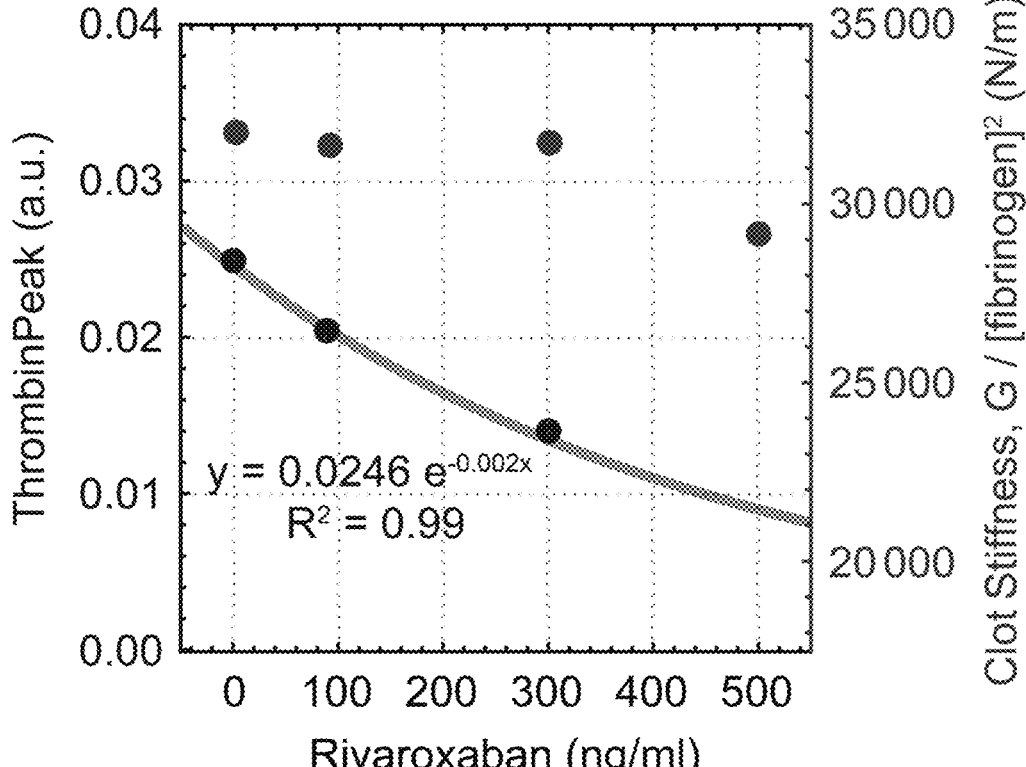
Figure 22:
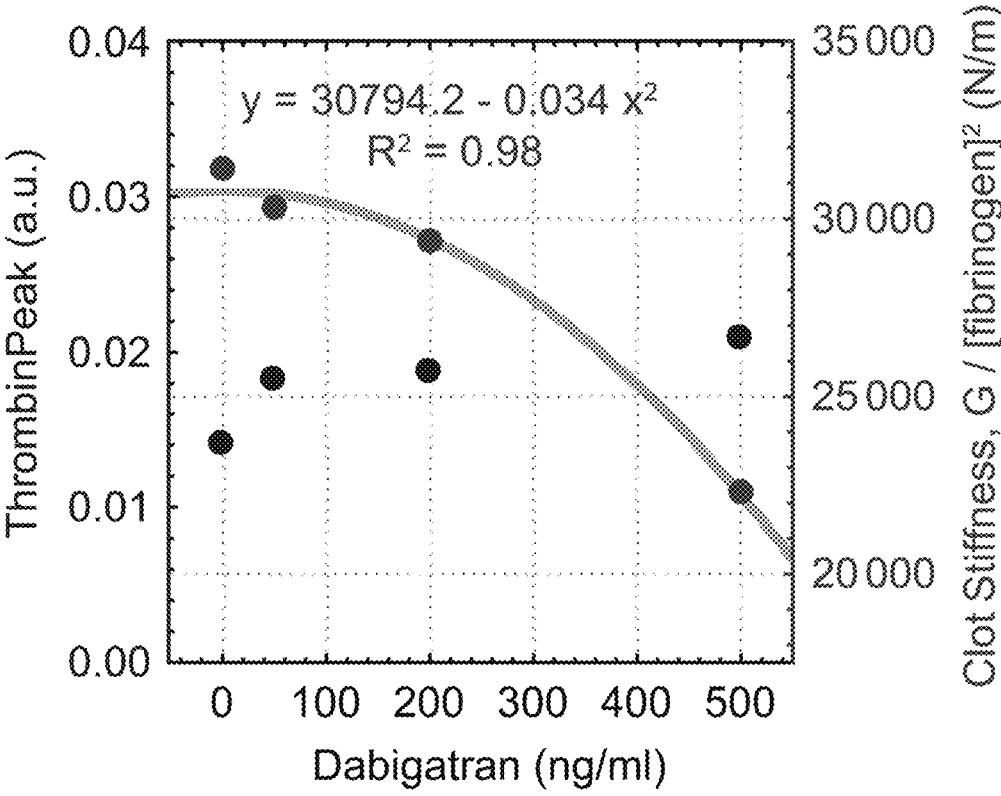
Figure 22:
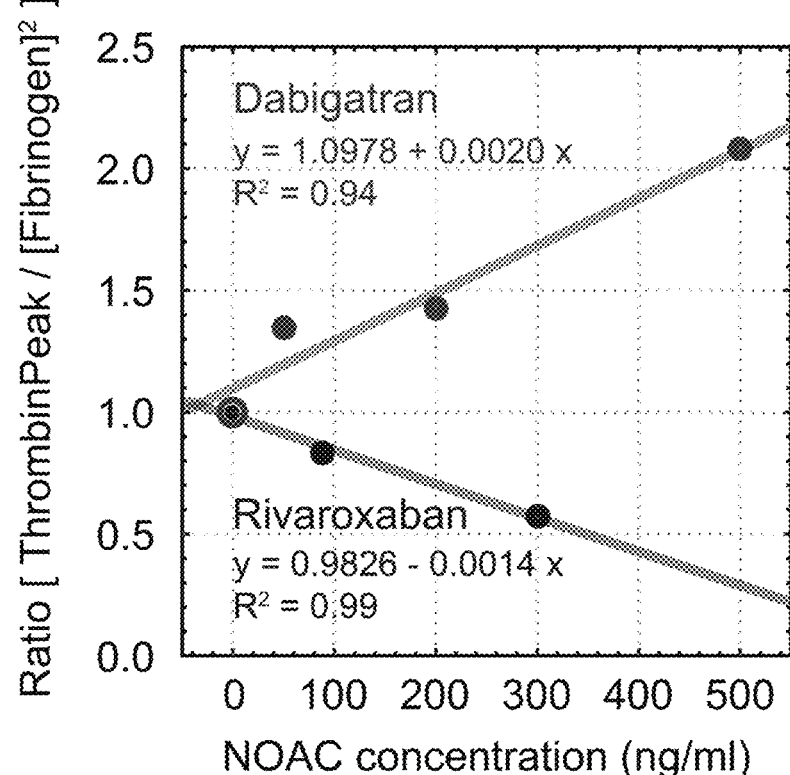

An example illustrating the TEG-like viscoelastic parameters, extracted using the hemostatic parameters from the fit, being used to determine the concentration of and discriminate between a factor-IIa (Dabigatran or Pradaxa®) and factor-Xa (Rivaroxaban or Xarelto®) inhibitor-based anticoagulant, as measured using a physical element in a disposable test strip is shown in FIGS. 20(*a*), 20(*b*), 21(*a*), 21(*b*), 22(*a*), 22(*b*), 22(*c*) and 22(*d*). In this specific example, FIG. 20(*a*) illustrates a dose response for clot formation time (R) demonstrating an increasing linear trend (regression coefficient $R^2=0.997$) when exposed to blood samples with increasing concentrations of Dabigatran, which directly inhibits thrombin or Factor-IIa activity, or in other words the cleaving/conversion of fibrinogen to fibrin. FIG. 20(*b*) further illustrates a correlation plot between the increasing R times in the Dabigatran blood samples as measured using the disposable test strips (CoagCare) and the ACT times measured using the TEG-5000 RapidTEG assay, which demonstrated a linear correlation (regression coefficient $R^2=0.997$). Further in this specific example, FIG. 21(*a*) illustrates a dose response for clot formation time (R) demonstrating an increasing linear trend (regression coefficient $R^2=0.989$) when exposed to blood samples with increasing concentrations of Rivaroxaban, which directly inhibits thrombin or Factor-IIa generation. FIG. 21(*b*) further illustrates a correlation plot between the increasing R times in the Rivaroxaban blood samples as measured using the disposable test strips (CoagCare) and the ACT times measured using the TEG-5000 RapidTEG assay, which demonstrated a linear correlation (regression coefficient $R^2=0.997$). Further in this example, FIG. 22(*a*) portrays the blood coagulation cascade processes and specifically illustrates Dabigatran's inhibition of thrombin activity or the cleaving/conversion of fibrinogen to fibrin and Rivaroxaban's inhibition of thrombin generation through Factor-Xa, and their respective effect on the clot formation time (R) as detailed above. FIG. 22(*b*) specifically illustrates Rivaroxaban's effect of reducing the maximum thrombin generation (ThombinPeak) in an exponential trend (regression coefficient $R^2=0.99$) with increasing Rivaroxaban concentrations in the tested blood samples, but with limited to no effect on clot stiffness G that tracks the cleaved fibrinogen converted to fibrin (as seen in FIG. 17(*b*)). This limited effect is due to the fact that, despite Rivaroxaban's inhibition of thrombin generation through Factor-Xa (as seen in FIG. 22(*a*)), typically only a minimum threshold amount of thrombin needs to be generated before the coagulation process cascades on to the conversion of fibrinogen to fibrin. FIG. 22(*c*) specifically illustrates Dabigatran's effect of reducing the clot stiffness G (that tracks the cleaved fibrinogen converted to fibrin) in a quadratic trend (regression coefficient $R^2=0.98$) with increasing Dabigatran concentrations in the tested blood samples, but with limited to no effect on maximum thrombin generation (ThrombinPeak). This limited effect is due to the fact that Dabigatran only inhibits Thrombin activity but has little to no effect on the coagulation cascade processes upstream to Thrombin that affect its generation (as seen in FIG. 22(*a*)).

This differential response of the Factor-IIa and Factor-Xa inhibitor anticoagulants to thrombin generation and thrombin activity or cleaving/conversion of fibrinogen was used to discriminate between their presence in the blood samples. FIG. 22(d) specifically illustrates this differential response using a metric that is expressed as the ratio of the normalized ThrombinPeak and clot stiffness G (referred to as [Fibrinogen]$^2$ in this figure), which when plotted for the tested samples with increasing Dabigatran and Rivaroxaban concentrations (referred to as new oral anticoagulants or NOAC in this figure) demonstrated an increasing and decreasing linear trend, respectively. Thus, with appropriate calibration of the test results, this differential response can be used to discriminate between the presence of Factor-IIa and Factor-Xa inhibitor anticoagulants. Following the successful identification of the specific anticoagulant in the blood sample, the effect of the anticoagulant on clot formation time R can be used to determine the concentration of the anticoagulant, using a pre-determined calibration or anticoagulant dose-response curve ((as seen in FIGS. 20(a) and 21(a)).

Listing of Features and Embodiments

The following list provides additional features that may be present in devices and/or methods according to the invention.

1. The substrate layer may be composed of a material which is selected from a group of materials including polymers such as polyester (PET), plastics, printed circuit board, etc., and/or may be fabricated using mass manufacturing methods including roll-to-roll continuous flow manufacturing.

2. The physical element (i.e. suspended beam) of the substrate layer may be patterned/formed by a technique selected from etching, laser treatment, printing and mechanical punching/cutting.

3. An electrically conductive path running across the physical element may comprise pure metals (e.g., Silver, Gold, Palladium, Titanium, Tungsten, Platinum, Stainless Steel, etc.), metal alloys, semiconducting materials (e.g., Silicon), conductive polymers, etc., and/or the electrical path may be incorporated on top, bottom, inside or as part of the substrate layer.

4. An electrically conductive path running across the physical element may be formed by a technique selected from metal evaporation, thin metal film extrusion, printing or laser treatment.

5. When actuating the oscillation of and measuring signal from a physical element, an electrical field can be applied, and a detection signal can be measured across independent electrically conductive paths.

6. When actuating the oscillation of and measuring signal from a physical element, oscillation can be induced through a time-varying electrical field and constant magnetic field, or a constant electrical field and time-varying magnetic field. The time-varying field may correspond to at least one of the physical element's fundamental or harmonic frequencies of resonance.

7. The detection signal resulting from oscillation of the physical element can be monitored in a range of frequencies in the vicinity (e.g., within a factor of 1.5, 2, 3, 4 or 5) of the frequency of the time-varying excitation field or fields.

8. Oscillation of a physical element or of two or more independent physical elements may be induced at two or more frequencies, and the oscillations may comprise two in-plane oscillations and/or an in-plane oscillation and an out-of-plane oscillation at different frequencies.

9. The lower layers of a device according to the invention can be positioned at a fixed or adjustable distance below the substrate layer, and/or the substrate layer can be clamped or affixed to the lower layers everywhere except the physical element(s).

10. Methods according to the invention can comprise inducing a standing shear-wave field in the medium between a physical element and the lower layers.

11. Devices according to the invention may comprise additional layers such as those shown in FIG. 2(b).

12. One or more layers of a device according to the invention may comprise at least one channel or opening suitable to permit the entry of a fluid sample into the reaction chamber, which optionally may be of suitable dimensions such that the fluid sample can enter into said reaction chamber by means of capillary action, and/or at least one channel or opening suitable to permit the displacement of air therethrough upon the filling of the reaction chamber with a fluid sample.

13. At least one surface of the chamber of a device may have a low contact angle with fluids (e.g., less than or equal to 45 degrees), which can facilitate capillary action of an aqueous fluid sample into the chamber.

14. Methods may comprise computing static or dynamic viscoelastic properties of a fluid from the measured viscosities and/or density of fluid at different applied shear rates (f); theoretical or empirical models may be used in such computations.

15. A change in one or a combination of oscillation characteristics of at least one physical element may be used in methods to determine the fluid properties before, during and/or after a chemical reaction in the sample.

16. Methods in which a blood sample is analyzed may comprise bringing a blood sample into contact with at least one blood clotting agent before, during or after introduction of the sample into a chamber, wherein the oscillation characteristics of at least one physical element are used to determine blood fluid properties and blood clotting reaction dynamics such as clotting time in PT, PTT, ACT and/or TEG coagulation tests.

17. Methods in which a blood sample is analyzed may comprise determining the concentration of red blood cells or hematocrit in the blood sample. This determination may be performed or may use data acquired prior to bringing the fluid into contact with a clotting reagent. Blood clotting reaction dynamics and/or blood fluid properties may be calibrated or adjusted using the measured hematocrit.

18. When analyzing a blood sample comprising an anticoagulant, methods may comprise discriminating between and determining the concentration of one or more anticoagulants in the blood sample. This may be performed or may use data acquired before or after bringing the blood sample into contact with the clotting reagent.

The following list provides additional non-limiting examples of systems and methods contemplated according to the invention.

1. A system for measuring a fluid, comprising:
   a resonator configured to apply a shear rate and/or stress to the fluid;
   a sensor configured to measure a vibration of the resonator during application of the shear rate and/or stress; and a processor configured to identify a parameter indicative of a viscosity, viscoelasticity and/or density of the fluid based on a damping of the vibration of the resonator caused by the fluid at a fixed applied shear rate and/or stress.

2. The system of embodiment 1, wherein the sensor is configured to measure at least one of (a) a resonance frequency of the vibration, (b) a quality factor of the resonance vibration, (c) an amplitude of the resonance vibration, and (d) a phase of the resonance vibration.

3. The system of embodiment 1, wherein the sensor is configured to measure a combination of (a) a resonance frequency of the vibration, (b) a quality factor of the resonance vibration, (c) an amplitude of the resonance vibration, and (d) a phase of the resonance vibration.

4. The system of embodiment 1, wherein the resonator is a purely in-plane resonator.

5. The system of embodiment 1, wherein the resonator is a purely out-of-plane resonator.

6. The system of embodiment 1, further comprising:
a thermal sensor configured to sense a temperature of the fluid during the measurement of the vibration; and
a thermal actuator configured to control a temperature of the fluid during the measurement of the vibration.

7. A method of measuring a fluid, comprising:
applying a shear rate and/or stress to the fluid via a resonator;
measuring a vibration of the resonator during the application of the shear rate and/or stress; and
identifying a parameter indicative of a viscosity, viscoelasticity and/or density of the fluid based on a damping of the vibration of the resonator caused by the fluid, at a fixed applied shear rate and/or stress.

8. The method of embodiment 7, wherein:
the measured vibration is an in-plane vibration of the resonator at a frequency f at a fixed applied shear rate and/or stress such that the penetration depth of the shear wave $(\delta = \mathrm{Sqrt}(\eta/\rho\pi f)$ is relatively small; and
the identified parameter is indicative of the viscosity of the constant phase $(\eta_{cp})$ of a complex non-Newtonian fluid.

9. The method of embodiment 7, wherein:
the measured vibration is an in-plane vibration of the resonator at a frequency f at a fixed applied shear rate and/or stress such that the penetration depth of the shear wave $(\delta = \mathrm{Sqrt}(\eta/\rho\pi f)$ is relatively large, and
the identified parameter is indicative of the viscosity of the bulk $(\eta_{bulk})$ of a complex non-Newtonian fluid.

10. The method of embodiment 7, wherein the identified parameter is indicative of a concentration of an additive $(c_s)$ in a non-Newtonian fluid, 11. The method of embodiment 10, wherein the non-Newtonian fluid includes particulates or solid-phase objects.

12. The method of embodiment 7, further comprising:
identifying a standardized measure of bulk viscosity of a complex non-Newtonian fluid at a standardized additive concentration as a function of the fluid's properties.

13. The method of embodiment 12, wherein the standardized measure is identified as a function of one or more of viscosity of constant phase of fluid $(\eta_{cp})$, viscosity of bulk of fluid $(\eta_{bulk})$ and concentration of additive $(c_s)$.

14. The method of embodiment 7, further comprising:
computing static or dynamic viscoelastic properties of a complex non-Newtonian fluid as a function of time, from the measured viscosities and/or densities of fluid at different applied shear rates $(\overset{\circ}{\gamma})$ using different theoretical or empirical models.

15. The method of embodiment 14, wherein the viscoelastic properties include yield stress $(\tau_y)$.

16. The method of embodiment 14, wherein the viscoelastic properties are determined according to Casson's model—

$$\eta_{bulk} = \frac{\left(\sqrt{\tau_y} + \sqrt{k\overset{\circ}{\gamma}}\right)^2}{\overset{\circ}{\gamma}}$$

17. The method of embodiment 7, further comprising:
computing static or dynamic viscoelastic properties of a complex non-Newtonian fluid, from the standardized bulk viscosities of fluid computed at different concentrations of additive $(c_s)$ and applied shear rates $(\overset{\circ}{\gamma})$ using different theoretical or empirical models, thereby allowing for identification of an empirical relationship between the fluid property and concentration of additive $(c_s)$.

18. The method of embodiment 17, wherein the viscoelastic properties include yield stress $(\tau_y)$.

19. The method of embodiment 17, wherein the viscoelastic properties are determined according to Casson's model $$\eta_{bulk} = \frac{\left(\sqrt{\tau_y} + \sqrt{k\overset{\circ}{\gamma}}\right)^2}{\overset{\circ}{\gamma}}.$$

LIST OF REFERENCES CITED

1. R. Rosencranz, S. A. Bogen, "Clinical laboratory measurement of serum, plasma, and blood viscosity," *American Journal of Clinical Pathology*, vol. 125, Suppl. 1, pp. S78-S86, 2006.

2. E. Nwanko, C. J. Durning, "Fluid property investigation by impedance characterization of quartz crystal resonators (2 parts)," *Sensors and Actuators A. Physical*, vol. 72, pp. 99-109, 1999.

3. B. Jakoby, M. Scherer, M. Buskies, H. Eisenschmid, "An automotive engine oil viscosity sensor," *IEEE Sensors Journal*, vol. 3, pp. 562-568, 2003.

4. G. D. O. Lowe, "Blood rheology in arterial disease," *Clinical Science*, vol. 71, pp. 137-146, 1986.

5. G. D. O. Lowe, "Blood rheology and vascular disease," *Haemostasis and Thrombosis* (ed. by A. L. Bloom et al), 3rd ed., pp. 1169-1188. Churchill Livingstone, Edinburgh, 1994.

6. L. Dintenfass, "Blood Microrheology: viscosity factors in blood flow ischaemia and thrombosis," Butterworth, London, 1971.

7. G. D. O. Lowe, W. C. S Smith, H. D. Tunstall-Pedoe, I. K. Crombie, S. E. Lennie, J. Anderson, J. C. Barbenel, "Cardiovascular risk and haemorheology: results from the Scottish Heart Health Study and the MONICA project, Glasgow," *Clinical Haemorheology*, vol. 8, pp. 518-524, 1988.

8. G. D. O. Lowe, A. J. Lee, A. Rumley, J. F. Price, F. G. R. Fowkes, "Blood viscosity and risk of cardiovascular events: the Edinburgh Artery Study," *British Journal of Haematology*, vol. 96, pp. 168-73, 1997.

9. G. Ciuffetti, G. Schillaci, R. Lombardini, M. Pirro, G. Vaudo, E. Mannarino, "Prognostic impact of low-shear whole blood viscosity in hypertensive men," *European Journal of Clinical Investigation*, vol. 35 no. 2, pp. 93-98, February 2005.

10. S. Chien, J. Dormandy, E. Ernst, A. Matrai, "Clinical Hemorheology," Martinus Nijhoff Publishers, Dordrecht, 1987.

11. A. Matrai, R. B. Whittington, E. Ernst, "A simple method of estimating whole blood viscosity at standardized hematocrit," *Clinical Haemorheology*, vol. 7, pp. 261-265, 1987.

12. W. I. Rosenblum, "In vitro measurements of the effects of anticoagulants on the flow properties of blood: The relationship of these effects to red cell shrinkage," *Blood*, vol. 31, no. 2, pp. 234-241, 1968.

13. J. Wang, "Electrochemical Glucose Biosensors," *Chemical Reviews*, vol. 108, pp. 814-825, 2008.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for measuring, at one or more time points, one or more properties or changes in properties of a fluid sample, the device comprising:
   a chamber defining a singular internal volume of the device suitable for receiving and retaining the fluid sample;
   a plurality of layers, the plurality comprising at least a bottom layer below the chamber and at least a substrate layer above the chamber, wherein:
      the substrate layer is linked to at least one suspended beam at each end of its length;
      the suspended beam is located above the chamber, the suspended beam having a face capable of physical contact with the fluid sample;
      and the suspended beam is configured to oscillate upon application of an actuating signal to at least one electrically conductive path, which runs across the suspended beam.

2. The device of claim 1, further comprising at least one magnetic field source configured to provide a magnetic field with field lines intersecting the suspended beam, such that the suspended beam will oscillate when the actuating signal in the form of an electrical current or voltage is applied and at least one of the magnetic field and actuating signal is time-varying.

3. The device of claim 1, further comprising at least one magnetic field source configured to provide a magnetic field with field lines intersecting the suspended beam, such that an oscillation of the suspended beam induces a current or voltage across at least one electrically conductive path.

4. The device of claim 1, further comprising an actuator configured to cause the suspended beam to oscillate by application of one or more excitation fields chosen from (i) piezoelectricity-based mechanical, (ii) capacitive, (iii) electromagnetic, and (iv) thermal excitation fields, wherein oscillation of the suspended beam generates one or more signals chosen from (i) piezoelectricity-based electrical, (ii) capacitive, (iii) electromagnetic, (iv) thermal, and (v) optical detection signals.

5. The device of claim 1, wherein the device comprises at least two independent electrically conductive paths which run across the suspended beam, such that one of the electrically conductive paths can be used to cause an oscillation of the suspended beam and another of the electrically conductive paths can be used for detection of a current or voltage induced by the oscillation.

6. The device of claim 1, wherein a top surface of the chamber is comprised of at least a portion of the substrate layer.

7. The device of claim 1, wherein the fluid sample when applied to the chamber occupies at least a volume in the vicinity of the region below at least one of the at least one suspended beam and above the bottom layer.

8. The device of claim 7, wherein the flow of the fluid sample into the chamber is directed along the length of at least one of the at least one suspended beam.

9. The device of claim 7, wherein the fluid sample affects the oscillations in at least one of the at least one suspended beam.

10. The device of claim 1, wherein at least one of the substrate layer or the bottom layer comprise at least one electrically conductive path configured to detect the presence of the fluid in the chamber.

11. The device of claim 1, wherein the device comprises at least one active agent chosen from:
   (i) at least one clotting agent in an amount effective to induce clotting of a blood sample upon placement of the blood sample in the chamber and exposure of the blood sample to the clotting agent;
   (ii) at least one anticoagulant;
   (iii) at least one coagulation factor; or
   (iv) at least one agent that alters fluid viscosity in an amount sufficient to alter viscosity by at least 0.001 centipoise.

12. A method of measuring one or more properties or changes in properties of a fluid sample using a device according to claim 1, the method comprising:
   placing the fluid sample in the chamber of the device;
   oscillating at least one of the at least one suspended beam of the device, wherein the oscillation induces a current or voltage in at least one of the electrically conductive paths of the device;
   measuring the current or voltage at one or more times; and
   using one or more of the measurements of the current or voltage to calculate the one or more properties or changes in properties of the fluid sample.

13. The method of claim 12, wherein at least one oscillation characteristic is chosen from amplitude, phase, a change in oscillation frequency, and quality factor is measured and used in the determination of one or more properties of the fluid sample.

14. The method of claim 12, wherein oscillation characteristics are measured at two or more of:
   (a) a time point prior to a reaction in the fluid sample,
   (b) a time point during the reaction in the fluid sample, and
   (c) a time point after the reaction in the fluid sample,
   wherein the reaction changes one or more of the properties of the fluid sample being measured.

15. The method of claim 12, wherein the method comprises in-plane and out-of-plane oscillating steps and at least two properties of the fluid sample chosen from continuous phase viscosity, bulk viscosity, viscoelasticity, and density.

16. The method of claim 12, wherein the fluid sample is a blood sample and at least one of plasma viscosity, whole blood viscosity, blood viscoelasticity, blood density, hematocrit, platelet count, blood clotting time, blood clot stiffness, platelet contraction activity, fibrinolysis activity, concentration of a blood coagulation factor, activity of a blood coagulation factor, concentration of a blood constituent, activity of a blood constituent, type of an anticoagulant present in the sample, and concentration of an anticoagulant present in the sample is determined.

* * * * *